US011421248B2

(12) United States Patent
Ko

(10) Patent No.: US 11,421,248 B2
(45) Date of Patent: Aug. 23, 2022

(54) TEMPERATURE-BASED TRANSIENT DELIVERY OF NUCLEIC ACIDS AND PROTEINS TO CELLS AND TISSUES

(71) Applicant: Elixirgen Therapeutics, Inc., Baltimore, MD (US)

(72) Inventor: Minoru S. H. Ko, Cockeysville, MD (US)

(73) Assignee: Elixirgen Therapeutics, Inc., Baltimore, MD (US)

( * ) Notice: Subject to any disclaimer, the term of this patent is extended or adjusted under 35 U.S.C. 154(b) by 0 days.

(21) Appl. No.: 17/404,901

(22) Filed: Aug. 17, 2021

(65) Prior Publication Data

US 2021/0381005 A1 Dec. 9, 2021

Related U.S. Application Data

(63) Continuation of application No. PCT/US2020/067506, filed on Dec. 30, 2020.

(60) Provisional application No. 62/992,700, filed on Mar. 20, 2020, provisional application No. 62/955,801, filed on Dec. 31, 2019.

(51) Int. Cl.
| | |
|---|---|
| *C07K 14/02* | (2006.01) |
| *C07K 14/005* | (2006.01) |
| *C12N 15/86* | (2006.01) |
| *A61K 39/00* | (2006.01) |
| *C07K 14/16* | (2006.01) |
| *A61P 31/14* | (2006.01) |
| *A61K 9/00* | (2006.01) |
| *A61K 39/215* | (2006.01) |
| *C12N 7/00* | (2006.01) |
| *C12N 15/113* | (2010.01) |

(52) U.S. Cl.
CPC ............ *C12N 15/86* (2013.01); *A61K 9/0019* (2013.01); *A61K 39/215* (2013.01); *A61P 31/14* (2018.01); *C12N 7/00* (2013.01); *C12N 15/113* (2013.01); *A61K 2039/5256* (2013.01); *A61K 2039/53* (2013.01); *C12N 2310/122* (2013.01); *C12N 2310/14* (2013.01); *C12N 2320/32* (2013.01); *C12N 2760/18643* (2013.01); *C12N 2760/18671* (2013.01); *C12N 2770/36143* (2013.01); *C12N 2770/36171* (2013.01)

(58) Field of Classification Search
CPC ................. C07K 14/005; C12N 15/86; C12N 2770/36122; C12N 2830/42; A61K 48/00
See application file for complete search history.

(56) References Cited

U.S. PATENT DOCUMENTS

| | | | |
|---|---|---|---|
| 5,217,879 A | 6/1993 | Huang et al. | |
| 6,391,632 B1 | 5/2002 | Dubensky, Jr. et al. | |
| 6,426,196 B1 | 7/2002 | Dubensky, Jr. et al. | |
| 6,451,592 B1 | 9/2002 | Dubensky, Jr. et al. | |
| 6,465,634 B1 | 10/2002 | Dubensky, Jr. et al. | |
| 6,592,874 B2 | 7/2003 | Schlesinger et al. | |
| 6,943,015 B2 | 9/2005 | Frolov et al. | |
| 7,005,275 B2 | 2/2006 | Renner et al. | |
| 7,045,335 B2 | 5/2006 | Smith et al. | |
| 7,078,218 B2 | 7/2006 | Smith et al. | |
| 7,332,322 B2 | 2/2008 | Frolov et al. | |
| 7,425,337 B2 | 9/2008 | Smith et al. | |
| 7,442,381 B2 | 10/2008 | Smith et al. | |
| 7,531,180 B2 | 5/2009 | Polo et al. | |
| 7,541,038 B2 | 6/2009 | Kovacs et al. | |
| 7,572,453 B2 | 8/2009 | Polo et al. | |
| 7,771,979 B2 | 8/2010 | Polo et al. | |
| 7,807,792 B2 | 10/2010 | Sugiyama et al. | |
| 7,811,812 B2 | 10/2010 | Dubensky, Jr. et al. | |
| 8,158,418 B2 | 4/2012 | Polo et al. | |
| 8,252,574 B2 | 8/2012 | Mason et al. | |
| 8,278,036 B2 | 10/2012 | Kariko et al. | |

(Continued)

FOREIGN PATENT DOCUMENTS

| | | | |
|---|---|---|---|
| EP | 819250 B1 | 1/1998 | |
| EP | 1066395 B1 | 9/2005 | |

(Continued)

OTHER PUBLICATIONS

Akiyama et al., (2016). "Transient ectopic expression of the histone demethylase JMJD3 accelerates the differentiation of human pluripotent stem cells," Development, 143:3674-3685.

Ban et al., (2011). "Efficient generation of transgene-free human induced pluripotent stem cells (iPSCs) by temperature-sensitive Sendai virus vectors," Proc Natl Acad Sci USA, 108(34):14234-14239, 6 pages plus 6 pages of supporting information.

(Continued)

*Primary Examiner* — Barry A Chestnut
(74) *Attorney, Agent, or Firm* — Morrison & Foerster LLP

(57) ABSTRACT

The present disclosure relates to methods for transiently activating temperature-sensitive agents in one or more cells, for example by contacting one or more cells with a temperature-sensitive agent and transiently incubating the cells at a permissive temperature for inducing an activity of the temperature-sensitive agent in the cells. Additionally, the present disclosure relates to methods of contacting one or more cells in a subject with a temperature-sensitive agent and then lowering the subject's core body temperature to a permissive temperature for inducing an activity of the temperature-sensitive agent in the cells. The disclosure also relates to methods of contacting one or more cells in a subject with a temperature-sensitive agent, maintaining the subject's surface body temperature at a permissive temperature for inducing an activity of the temperature-sensitive agent in the cells. Further disclosed are methods of treating a subject with a temperature-sensitive therapeutic agent.

20 Claims, 28 Drawing Sheets

Specification includes a Sequence Listing.

(56) References Cited

U.S. PATENT DOCUMENTS

| | | |
|---|---|---|
| 8,426,188 B2 | 4/2013 | Weaver et al. |
| 8,557,779 B2 | 10/2013 | Sugiyama |
| 8,647,864 B2 | 2/2014 | Polo et al. |
| 8,691,966 B2 | 4/2014 | Kariko et al. |
| 8,709,441 B2 | 4/2014 | Rayner et al. |
| 8,748,089 B2 | 6/2014 | Kariko et al. |
| 8,748,591 B2 | 6/2014 | Weaver et al. |
| 8,835,108 B2 | 9/2014 | Kariko et al. |
| 8,961,995 B2 | 2/2015 | Frolov et al. |
| 9,187,729 B2 | 11/2015 | DePaz et al. |
| 9,255,126 B2 | 2/2016 | Polo et al. |
| 9,273,288 B2 | 3/2016 | Mason et al. |
| 9,402,890 B2 | 8/2016 | Frolov et al. |
| 9,441,247 B2 | 9/2016 | Rayner et al. |
| 9,447,422 B2 | 9/2016 | DeHoff et al. |
| 9,580,690 B2 | 2/2017 | Weaver et al. |
| 9,670,466 B2 | 6/2017 | Tratschin et al. |
| 9,750,824 B2 | 9/2017 | Kariko et al. |
| 9,770,463 B2 | 9/2017 | Geall et al. |
| 9,862,930 B2 | 1/2018 | Dowdy et al. |
| 9,919,037 B2 | 3/2018 | Scheinberg et al. |
| 10,100,087 B2 | 10/2018 | O'Reilly et al. |
| 10,139,395 B2 | 11/2018 | Sugiyama |
| 10,166,281 B2 | 1/2019 | Akhata et al. |
| 10,174,317 B2 | 1/2019 | Brown et al. |
| 10,221,224 B2 | 3/2019 | Scheinberg et al. |
| 10,232,055 B2 | 3/2019 | Kariko et al. |
| 10,266,834 B2 | 4/2019 | Brown et al. |
| 10,335,456 B2 | 7/2019 | Ko |
| 10,426,822 B2 | 10/2019 | Sugiyama |
| 10,487,105 B2 | 11/2019 | Chivukula et al. |
| 10,508,265 B2 | 12/2019 | Jo |
| 10,533,186 B2 | 1/2020 | Weaver et al. |
| 10,538,786 B2 | 1/2020 | Kamrud et al. |
| 10,695,385 B2 | 6/2020 | Shirakawa et al. |
| 10,744,183 B2 | 8/2020 | Ko |
| 10,801,041 B2 | 10/2020 | Wagner |
| 10,815,273 B2 | 10/2020 | Scheinberg et al. |
| 10,967,057 B2 | 4/2021 | Yu et al. |
| 10,968,248 B2 | 4/2021 | Chivukula et al. |
| 10,973,899 B2 | 4/2021 | Hagen et al. |
| 11,015,204 B2 | 5/2021 | Limphong et al. |
| 11,026,964 B2 | 6/2021 | Geall et al. |
| 11,033,613 B2 | 6/2021 | Scheinberg |
| 11,078,237 B2 | 8/2021 | Franti et al. |
| 11,136,594 B2 | 10/2021 | Fusaki et al. |
| 2005/0208071 A1 | 9/2005 | Beer et al. |
| 2005/0282279 A1 | 12/2005 | Hwu |
| 2006/0024788 A1* | 2/2006 | Renner ............... C12N 15/86 435/456 |
| 2008/0286848 A1* | 11/2008 | Skiadopoulos ...... A61K 39/155 435/235.1 |
| 2010/0203027 A1* | 8/2010 | Tani ................ A61K 38/195 435/320.1 |
| 2011/0207223 A1 | 8/2011 | Tang et al. |
| 2011/0300205 A1 | 12/2011 | Geall et al. |
| 2016/0120947 A1 | 5/2016 | Scadden et al. |
| 2016/0215270 A1* | 7/2016 | Ban ..................... C12N 7/00 |
| 2018/0104359 A1 | 4/2018 | Kamrud |
| 2018/0153975 A1* | 6/2018 | Fritsch ........... A61K 39/001197 |
| 2018/0171340 A1 | 6/2018 | Kamrud |
| 2018/0195085 A1 | 7/2018 | Saeki |
| 2019/0055526 A1 | 2/2019 | Pule et al. |
| 2019/0091329 A1* | 3/2019 | Brito ................... A61K 39/245 |
| 2019/0151432 A1 | 5/2019 | Gallei et al. |
| 2019/0185822 A1 | 6/2019 | Akhata et al. |
| 2019/0216956 A1 | 7/2019 | Taub et al. |
| 2019/0224299 A1 | 7/2019 | Kamrud et al. |
| 2019/0282659 A1 | 9/2019 | Ko |
| 2020/0016274 A1 | 1/2020 | Karve et al. |
| 2020/0030460 A1 | 1/2020 | Kariko et al. |
| 2020/0283797 A1 | 9/2020 | Saeki et al. |
| 2020/0299724 A1 | 9/2020 | Beissert et al. |
| 2020/0299725 A1 | 9/2020 | Beissert et al. |
| 2021/0268013 A1 | 9/2021 | Geall et al. |

FOREIGN PATENT DOCUMENTS

| | | |
|---|---|---|
| EP | 1186667 B1 | 7/2007 |
| JP | 4478788 B2 | 6/2010 |
| WO | WO-2000070070 A1 | 11/2000 |
| WO | WO-2010008054 A1 | 1/2010 |
| WO | WO-2014144932 A2 | 9/2014 |
| WO | WO-2014200910 A2 | 12/2014 |
| WO | WO2018081318 * | 5/2018 |
| WO | WO-2018081318 A1 | 5/2018 |
| WO | WO2018170347 * | 9/2018 |
| WO | WO-2018170347 A1 | 9/2018 |
| WO | WO-2021119545 A1 | 6/2021 |
| WO | WO-2021138447 A1 | 7/2021 |
| WO | WO-2021138448 A1 | 7/2021 |

OTHER PUBLICATIONS

Beitzel et al., (2010). "High-resolution functional mapping of the Venezuelan equine encephalitis virus genome by insertional mutagenesis and massively parallel sequencing" PLoS Pathog., 6(10):e1001146, 13 pages plus 6 pages of supplementary material.

Bozoki et al., (2020). "Specificity studies of the Venezuelan equine encephalitis virus non-structural protein 2 protease using recombinant fluorescent substrates," Int J Mol Sci, 21:7686, 26 pages.

Callaway et al., (2015). "Part 8: post-cardiac arrest care: 2015 American Heart Association Guidelines Update for Cardiopulmonary Resuscitation and Emergency Cardiovascular Care." Circulation, 132(suppl 2):S465-S482.

Du et al., (2009). "The spike protein of SARS-CoV—a target for vaccine and therapeutic development," Nat Rev Microbiol, 7(3):226-236.

Fuchs et al., (2005). "Polyarginine as a multifunctional fusion tag," Protein Science, 14:1538-1544.

GenBank, (2004). "Accession No. L01443.1: Venezuelan equine encephalitis virus strain TC-83, complete genome," 5 pages.

GenBank, (2018). "Accession No. NP_740697.1: Putative nonstructural protein nsP2 [Venezuelan equine encephalitis virus]," 2 pages.

GenBank, (2020). "Accession No. NC_045512.2: Severe acute respiratory syndrome coronavirus 2 isolate Wuhan-Hu-1, complete genome," 15 pages.

GenBank, (2020). "Accession No. YP_009724390.1: surface glycoprotein [Severe acute respiratory syndrome coronavirus 2]," 3 pages.

Golombek et al., (2018). "Intradermal Delivery of Synthetic mRNA Using Hollow Microneedles for Efficient and Rapid Production of Exogenous Proteins in Skin," Molecular Therapy: Nucleic Acids, 11:382-392.

Goparaju et al., (2017). "Rapid differentiation of human pluripotent stem cells into functional neurons by mRNAs encoding transcription factors," Sci Rep., 7:42367, 12 pages.

Grifoni et al., (2020). "A Sequence Homology and Bioinformatic Approach Can Predict Candidate Targets for Immune Responses to SARS-CoV-2," Cell Host Microbe., 27(4):671-680.

Ieda et al., (2010). "Direct Reprogramming of Fibroblasts into Functional Cardiomyocytes by Defined Factors," Cell, 142:375-386.

Inoue et al., (2003). "Nontransmissible virus-like particle formation by F-deficient Sendai virus is temperature sensitive and reduced by mutations in M and HN proteins," J Virol, 77(5):3238-3246.

International Search Report and Written Opinion for International Patent Application No. PCT/US2020/067506 dated Apr. 13, 2021, 21 pages.

International Search Report and Written Opinion for International Patent Application No. PCT/US2020/067507 dated May 27, 2021, 20 pages.

Johansson et al., (2012). "Intradermal electroporation of naked replicon RNA elicits strong immune responses," PLoS One, 7(1):e29732, 7 pages.

John et al., (2013). "Anti-PD-1 antibody therapy potently enhances the eradication of established tumors by gene-modified T cells," Clin Cancer Res, 19(20): 5636-5646.

(56) References Cited

OTHER PUBLICATIONS

Jose et al., (2009). "A structural and functional perspective of alphavirus replication and assembly," Future Microbiol, 4(7):837-856, 30 pages.

Kaczmarek et al., (2017). "Advances in the delivery of RNA therapeutics: from concept to clinical reality," Genome Medicine, 9:60, 16 pages.

Lambert et al., (2020). "Consensus summary report for CEPI/BC Mar. 12-13, 2020 meeting: Assessment of risk of disease enhancement with COVID-19 vaccines," Vaccine, 38(31):4783-4791.

Masui et al., (2005). "An efficient system to establish multiple embryonic stem cell lines carrying an inducible expression unit," Nucleic Acids Res., 33:e43, 8 pages.

McFadden et al., (1985). "Thermal mapping of the airways of humans," J Appl Physiol, 58(2):564-70.

Mortola, (2013). "Thermographic analysis of body surface temperature of mammals," Zoolog Sci, 30(2):118-24.

Niwa et al., (1991). "Efficient selection for high-expression transfectants with a novel eukaryotic vector," Gene, 108(2):193-9.

Park et al., (2016). "Sendai virus, an RNA virus with no risk of genomic integration, delivers CRISPR/Cas9 for efficient gene editing," Mol Ther Methods Clin Dev, 3:16057, 9 pages.

Petrakova et al., (2005). "Noncytopathic replication of Venezuelan equine encephalitis virus and eastern equine encephalitis virus replicons in mammalian cells," J Virol, 79(12):7597-608, 15 pages.

Pittl et al., (2013). "Invasive versus non-invasive cooling after in- and out-of-hospital cardiac arrest: a randomized trial," Clin Res Cardiol, 102:607-14.

Roberts et al., (2017). "Immune checkpoint inhibitors: navigating a new paradigm of treatment toxicities," Asia Pac J Clin Oncol, 13(4):277-288.

Russo et al., (2006). "Purification, crystallization and X-ray diffraction analysis of the C-terminal protease domain of Venezuelan equine encephalitis virus nsP2," Acta Crystallogr Sect F Struct Biol Cryst Commun, 62(Pt 6):514-517.

Shin et al., (2016). "Enhanced Anti-tumor Reactivity of Cytotoxic T Lymphocytes Expressing PD-1 Decoy," Immune Netw, 16:134-9.

Warren et al., (2010). "Highly efficient reprogramming to pluripotency and directed differentiation of human cells with synthetic modified mRNA," Cell Stem Cell, 7(5):618-630.

Weaver et al., (2004). "Venezuelan equine encephalitis," Annu Rev Entomol, 49:141-174.

World Health Organization, (2009). "Intradermal Delivery of Vaccines: A review of the literature and the potential for development for use in low- and middle-income countries," WHO & PATH, 94 pages.

Wu et al., (2020). "A new coronavirus associated with human respiratory disease in China," Nature, 579(7798):265-269.

Yoshioka et al., (2013). "Efficient generation of human iPSCs by a synthetic self-replicative RNA," Cell Stem Cell, 13(2):246-254.

Yoshioka et al., (2017). "Enhanced generation of iPSCs from older adult human cells by a synthetic five-factor self-replicative RNA," PLoS One, 12(7):e0182018, 17 pages.

Zhou et al., (2008). "In vivo reprogramming of adult pancreatic exocrine cells to beta-cells," Nature, 455(7213):627-632.

Zhou et al., (2020). "A pneumonia outbreak associated with a new coronavirus of probable bat origin," Nature, 579(7798):270-273.

\* cited by examiner

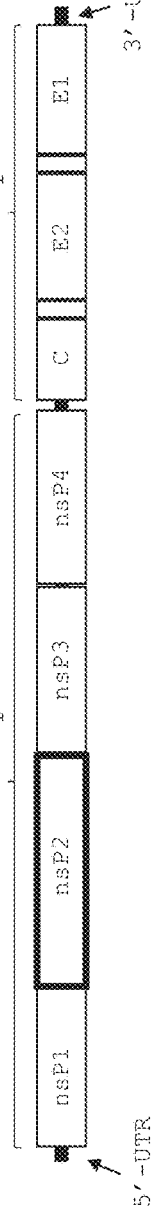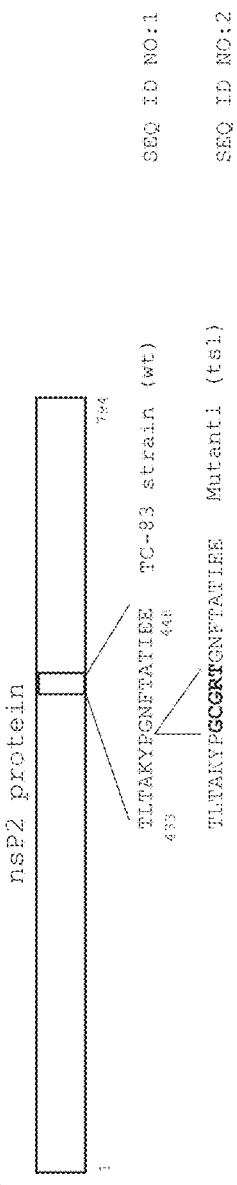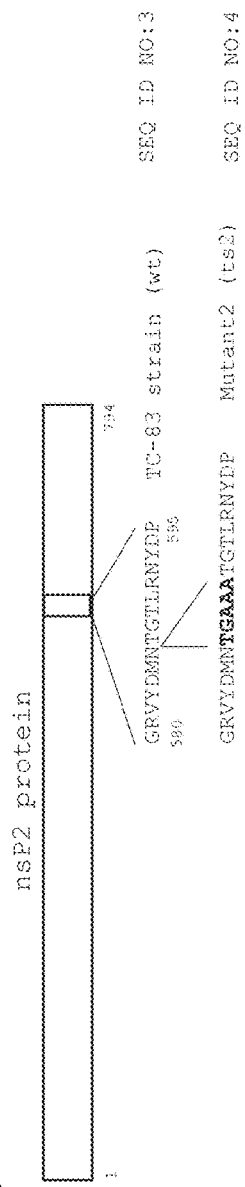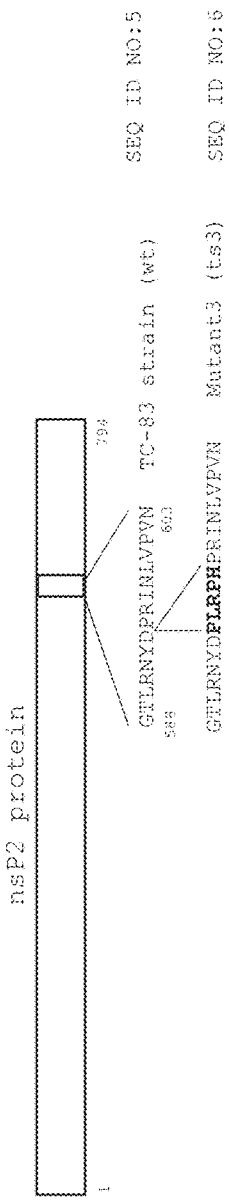

TC-83 (wt)
SEQ ID NO:7        ACACTGACTGCCAAGTACCCTGGGAATTTCACTGCCACG
Mutant 1 (ts1)
SEQ ID NO:8        ACACTGACTGCCAAGTACCCTGGGTGCGGCCGGACTGGGAATTTCACTGCCACG

SEQ ID NO:13       TLTAKYPGNFTAT
SEQ ID NO:14       TLTAKYPGCGRTGNFTAT

FIG. 2A

TC-83 (wt)
SEQ ID NO:9      GGAAGAGTCTATGACATGAACACTGGTACACTGCGCAAT

Mutant 2 (ts2)
SEQ ID NO:10     GGAAGAGTCTATGACATGAACACTGGTGCCGCCGCAACTGGTACACTGCGCAAT

SEQ ID NO:15     GRVYDMNTGTLRN

SEQ ID NO:16     GRVYDMNTGAAATGTLRN

FIG. 2B

TC-83 (wt)
SEQ ID NO:11       GGTACACTGCGCAATTATGATCCGCGCATAAACCTAGTA

Mutant 3 (ts3)
SEQ ID NO:12       GGTACACTGCGCAATTATGATCCGCTGCGCCCCATCCGCGCATAAACCTAGTA

SEQ ID NO:17       GTLRNYDPRINLV
SEQ ID NO:18       GTLRNYDPLRPHPRINLV

FIG. 2C

```
                         5'-UTR
              ┌─────────────────────────────────────────────────────────┐
TC-83      1  ATAGGCGGCGCATGAGAGAAGCCCAGACCAATTACCTACCTCAAAATGAGAAAGTTCACG   60
              ||||||||||||||||||||||||||||||||||||||||||| |||||||||||||||
Mutant4    1  ATGGGCGGCGCATGAGAGAAGCCCAGACCAATTACCTACCTCAAAATGAAAAAGTTCACG   60

TC-83     61  TTGACATCGAGGAAGACAGCCCATTCCTCAGAGCTTTGCAGCGGGAGTTCCGCAGTTTG  120
              ||||||||||||||||||||||||||||||||||||||| ||||||||||||||||||||
Mutant4   61  TTGACATCGAGAAGACAGCCCATTCCTCAGAGCTTTGCAGCGGGAGTTCCGCAGTTTG  120

51-nt CSE
                                    ┌──────────────────────────────────┐
TC-83    121  AGGTAGAAGCCAAGCAGGTCACTGATAATGACCAATGCTAAATGCCAGAGCCGTTTCGCATC  180
              ||||||||||||||||||||||||||||||||||||||||||| ||||||||||||||||
Mutant4  121  AGTAGAAGCCAAGCAGGTCACTGATAATGACCAATGCTAAATGCCAATGCAAGAGCCGTTTCGCATC  180

TC-83    181  TGGCTTCAAAAACTGATCGAAACGGGAGGTGGACCCATCCGACACGATCCTTGACATTGGAA  240
              |||||||||||||||||||||||||||||||||||||||||||||||||||||||||||
Mutant4  181  TTGCTTCAAAAACTGATCGAAACGGGAGGTGGACCCATCCGACACGATCCTTGACATTGGAA  240
```

FIG. 3

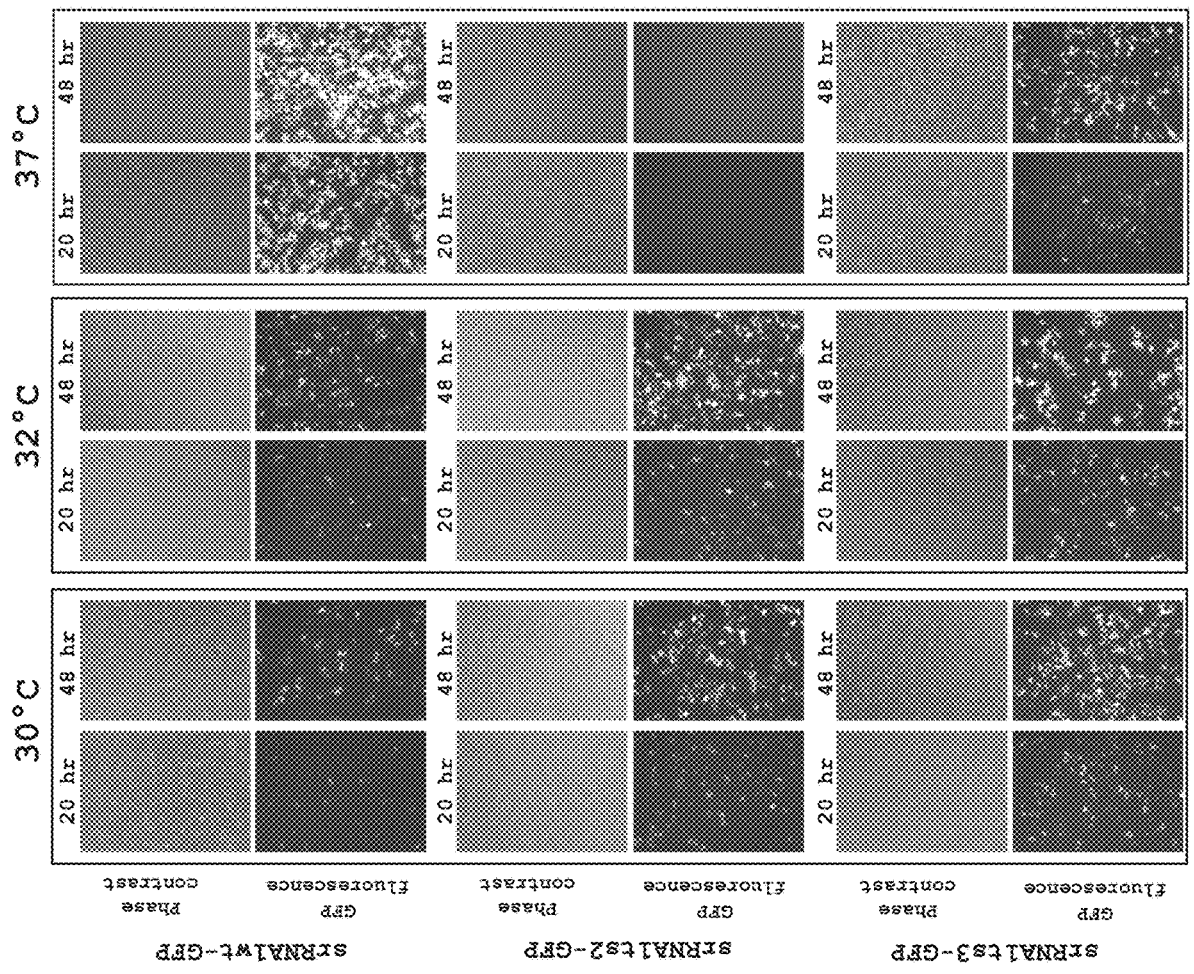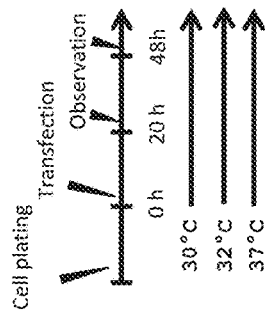
FIG. 4A

|      | 580 β5 | β6 592 | SEQ ID NO: |  | SEQ ID NO: |
|------|--------|--------|------------|--|------------|
| VEEV | GRVYDMNTGTLRN | | 21 | GRVYDMNTGAAATGTLRN | 29 |
| Aura | GDQILPIYGRVSV | | 22 | GDQILPITGAAAYGRVSV | 30 |
| WEEV | GRVADIRNNTIKD | | 23 | GRVADIRTGAAANNTIKD | 31 |
| BFV  | GMQIVVTEMRIQR | | 24 | GMQIVVTTGAAAEMRIQR | 32 |
| ONNV | NKQICITTRKVDE | | 25 | NKQICITTGAAATRKVDE | 33 |
| RRV  | GLQVNVPERKVQP | | 26 | GLQVNVPTGAAAERKVQP | 34 |
| SFV  | GKQAVIAERKIQP | | 27 | GKQAVIATGAAAERKIQP | 35 |
| SINV | GTQLDLQTGRTRV | | 28 | GTQLDLQTGAAATGRTRV | 36 |

SEQUENCE LISTING

<160> NUMBER OF SEQ ID NOS: 44

<210> SEQ ID NO 1
<211> LENGTH: 16
<212> TYPE: PRT
<213> ORGANISM: Venezuelan Equine Encephalitis Virus (VEEV)

```
<400> SEQUENCE: 1

Thr Leu Thr Ala Lys Tyr Pro Gly Asn Phe Thr Ala Thr Ile Glu Glu
1               5                   10                  15

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Thr Leu Thr Ala Lys Tyr Pro Gly Cys Gly Arg Thr Gly Asn Phe Thr
1               5                   10                  15

Ala Thr Ile Glu Glu
            20

<210> SEQ ID NO 3
<211> LENGTH: 16
<212> TYPE: PRT
<213> ORGANISM: Venezuelan Equine Encephalitis Virus (VEEV)

<400> SEQUENCE: 3

Gly Arg Val Tyr Asp Met Asn Thr Gly Thr Leu Arg Asn Tyr Asp Pro
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct

<400> SEQUENCE: 4

Gly Arg Val Tyr Asp Met Asn Thr Gly Ala Ala Ala Thr Gly Thr Leu
1               5                   10                  15

Arg Asn Tyr Asp Pro
            20

<210> SEQ ID NO 5
<211> LENGTH: 16
<212> TYPE: PRT
<213> ORGANISM: Venezuelan Equine Encephalitis Virus (VEEV)

<400> SEQUENCE: 5

Gly Thr Leu Arg Asn Tyr Asp Pro Arg Ile Asn Leu Val Pro Val Asn
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: Synthetic Construct

<400> SEQUENCE: 6

Gly Thr Leu Arg Asn Tyr Asp Pro Leu Arg Pro His Pro Arg Ile Asn
1               5                   10                  15

Leu Val Pro Val Asn
            20

<210> SEQ ID NO 7
<211> LENGTH: 39
```

-continued

```
<212> TYPE: DNA
<213> ORGANISM: Venezuelan Equine Encephalitis Virus (VEEV)

<400> SEQUENCE: 7
acactgactg ccaagtaccc tgggaatttc actgccacg                              39

<210> SEQ ID NO 8
<211> LENGTH: 54
<212> TYPE: DNA
<213> ORGANISM: Artificial Sequence
<220> FEATURE:
<223> OTHER INFORMATION: Synthetic Construct

<400> SEQUENCE: 8
acactgactg ccaagtaccc tgggtgcggc cggactggga atttcactgc cacg            54

<210> SEQ ID NO 9
<211> LENGTH: 39
<212> TYPE: DNA
<213> ORGANISM: Venezuelan Equine Encephalitis Virus (VEEV)

<400> SEQUENCE: 9
ggaagagtct atgacatgaa cactggtaca ctgcgcaat                             39

<210> SEQ ID NO 10
<211> LENGTH: 54
<212> TYPE: DNA
<213> ORGANISM: Artificial Sequence
<220> FEATURE:
<223> OTHER INFORMATION: Synthetic Construct

<400> SEQUENCE: 10
ggaagagtct atgacatgaa cactggtgcc gccgcaactg gtacactgcg caat            54

<210> SEQ ID NO 11
<211> LENGTH: 39
<212> TYPE: DNA
<213> ORGANISM: Venezuelan Equine Encephalitis Virus (VEEV)

<400> SEQUENCE: 11
ggtacactgc gcaattatga tccgcgcata aacctagta                             39

<210> SEQ ID NO 12
<211> LENGTH: 54
<212> TYPE: DNA
<213> ORGANISM: Artificial Sequence
<220> FEATURE:
<223> OTHER INFORMATION: Synthetic Construct

<400> SEQUENCE: 12
ggtacactgc gcaattatga tccgctgcgg ccccatccgc gcataaacct agta            54

<210> SEQ ID NO 13
<211> LENGTH: 13
<212> TYPE: PRT
<213> ORGANISM: Venezuelan Equine Encephalitis Virus (VEEV)

<400> SEQUENCE: 13

Thr Leu Thr Ala Lys Tyr Pro Gly Asn Phe Thr Ala Thr
1               5                   10

<210> SEQ ID NO 14
<211> LENGTH: 18
<212> TYPE: PRT
<213> ORGANISM: Artificial Sequence
```

<220> FEATURE:
<223> OTHER INFORMATION: Synthetic Construct

<400> SEQUENCE: 14

Thr Leu Thr Ala Lys Tyr Pro Gly Cys Gly Arg Thr Gly Asn Phe Thr
1               5                   10                  15

Ala Thr

<210> SEQ ID NO 15
<211> LENGTH: 13
<212> TYPE: PRT
<213> ORGANISM: Venezuelan Equine Encephalitis Virus (VEEV)

<400> SEQUENCE: 15

Gly Arg Val Tyr Asp Met Asn Thr Gly Thr Leu Arg Asn
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Synthetic Construct

<400> SEQUENCE: 16

Gly Arg Val Tyr Asp Met Asn Thr Gly Ala Ala Ala Thr Gly Thr Leu
1               5                   10                  15

Arg Asn

<210> SEQ ID NO 17
<211> LENGTH: 13
<212> TYPE: PRT
<213> ORGANISM: Venezuelan Equine Encephalitis Virus (VEEV)

<400> SEQUENCE: 17

Gly Thr Leu Arg Asn Tyr Asp Pro Arg Ile Asn Leu Val
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Synthetic Construct

<400> SEQUENCE: 18

Gly Thr Leu Arg Asn Tyr Asp Pro Leu Arg Pro His Pro Arg Ile Asn
1               5                   10                  15

Leu Val

<210> SEQ ID NO 19
<211> LENGTH: 240
<212> TYPE: DNA
<213> ORGANISM: Venezuelan Equine Encephalitis Virus (VEEV)

<400> SEQUENCE: 19
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240

```
<210> SEQ ID NO 20
<211> LENGTH: 240
<212> TYPE: DNA
<213> ORGANISM: Artificial Sequence
<220> FEATURE:
<223> OTHER INFORMATION: Synthetic Construct

<400> SEQUENCE: 20
atgggcggcg catgagagaa gcccagacca attacctact caaaatggaa aaagttcacg      60
ttgacatcga agaagacagc ccattcctca gagctttgca gcggagtttt ccgcagtttg     120
aagtagaagc caagcaggtc actgataatg accatgctaa tgcaagagcg ttttcgcatc     180
ttgcttcaaa actgatcgaa acggaggtgg acccatccga cacgatcctt gacattggaa     240

<210> SEQ ID NO 21
<211> LENGTH: 13
<212> TYPE: PRT
<213> ORGANISM: Venezuelan Equine Encephalitis Virus (VEEV)

<400> SEQUENCE: 21

Gly Arg Val Tyr Asp Met Asn Thr Gly Thr Leu Arg Asn
1               5                   10

<210> SEQ ID NO 22
<211> LENGTH: 13
<212> TYPE: PRT
<213> ORGANISM: Aura virus (Aura)

<400> SEQUENCE: 22

Gly Asp Gln Ile Leu Pro Ile Tyr Gly Arg Val Ser Val
1               5                   10

<210> SEQ ID NO 23
<211> LENGTH: 13
<212> TYPE: PRT
<213> ORGANISM: Western equine encephalitis virus (WEEV)

<400> SEQUENCE: 23

Gly Arg Val Ala Asp Ile Arg Asn Asn Thr Ile Lys Asp
1               5                   10

<210> SEQ ID NO 24
<211> LENGTH: 13
<212> TYPE: PRT
<213> ORGANISM: Barmah Forest virus (BFV)

<400> SEQUENCE: 24

Gly Met Gln Ile Val Val Thr Glu Met Arg Ile Gln Arg
1               5                   10

<210> SEQ ID NO 25
<211> LENGTH: 13
<212> TYPE: PRT
<213> ORGANISM: O'nyong-nyong virus (ONNV)

<400> SEQUENCE: 25

Asn Lys Gln Ile Cys Ile Thr Thr Arg Lys Val Asp Glu
1               5                   10

<210> SEQ ID NO 26
<211> LENGTH: 13
<212> TYPE: PRT
<213> ORGANISM: Ross River virus (RRV)

<400> SEQUENCE: 26
```

```
Gly Leu Gln Val Asn Val Pro Glu Arg Lys Val Gln Pro
1               5                   10

<210> SEQ ID NO 27
<211> LENGTH: 13
<212> TYPE: PRT
<213> ORGANISM: Semliki Forest virus (SFV)

<400> SEQUENCE: 27

Gly Lys Gln Ala Val Ile Ala Glu Arg Lys Ile Gln Pro
1               5                   10

<210> SEQ ID NO 28
<211> LENGTH: 13
<212> TYPE: PRT
<213> ORGANISM: Sindbis virus (SINV)

<400> SEQUENCE: 28

Gly Thr Gln Leu Asp Leu Gln Thr Gly Arg Thr Arg Val
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Synthetic Construct

<400> SEQUENCE: 29

Gly Arg Val Tyr Asp Met Asn Thr Gly Ala Ala Ala Thr Gly Thr Leu
1               5                   10                  15

Arg Asn

<210> SEQ ID NO 30
<211> LENGTH: 18
<212> TYPE: PRT
<213> ORGANISM: Artificial Sequence
<220> FEATURE:
<223> OTHER INFORMATION: Synthetic Construct

<400> SEQUENCE: 30

Gly Asp Gln Ile Leu Pro Ile Thr Gly Ala Ala Ala Tyr Gly Arg Val
1               5                   10                  15

Ser Val

<210> SEQ ID NO 31
<211> LENGTH: 18
<212> TYPE: PRT
<213> ORGANISM: Artificial Sequence
<220> FEATURE:
<223> OTHER INFORMATION: Synthetic Construct

<400> SEQUENCE: 31

Gly Arg Val Ala Asp Ile Arg Thr Gly Ala Ala Ala Asn Asn Thr Ile
1               5                   10                  15

Lys Asp

<210> SEQ ID NO 32
<211> LENGTH: 18
<212> TYPE: PRT
<213> ORGANISM: Artificial Sequence
<220> FEATURE:
<223> OTHER INFORMATION: Synthetic Construct
```

<400> SEQUENCE: 32

Gly Met Gln Ile Val Val Thr Thr Gly Ala Ala Ala Glu Met Arg Ile
1               5                   10                  15

Gln Arg

<210> SEQ ID NO 33
<211> LENGTH: 18
<212> TYPE: PRT
<213> ORGANISM: Artificial Sequence
<220> FEATURE:
<223> OTHER INFORMATION: Synthetic Construct

<400> SEQUENCE: 33

Asn Lys Gln Ile Cys Ile Thr Thr Gly Ala Ala Ala Thr Arg Lys Val
1               5                   10                  15

Asp Glu

<210> SEQ ID NO 34
<211> LENGTH: 18
<212> TYPE: PRT
<213> ORGANISM: Artificial Sequence
<220> FEATURE:
<223> OTHER INFORMATION: Synthetic Construct

<400> SEQUENCE: 34

Gly Leu Gln Val Asn Val Pro Thr Gly Ala Ala Ala Glu Arg Lys Val
1               5                   10                  15

Gln Pro

<210> SEQ ID NO 35
<211> LENGTH: 18
<212> TYPE: PRT
<213> ORGANISM: Artificial Sequence
<220> FEATURE:
<223> OTHER INFORMATION: Synthetic Construct

<400> SEQUENCE: 35

Gly Lys Gln Ala Val Ile Ala Thr Gly Ala Ala Ala Glu Arg Lys Ile
1               5                   10                  15

Gln Pro

<210> SEQ ID NO 36
<211> LENGTH: 18
<212> TYPE: PRT
<213> ORGANISM: Artificial Sequence
<220> FEATURE:
<223> OTHER INFORMATION: Synthetic Construct

<400> SEQUENCE: 36

Gly Thr Gln Leu Asp Leu Gln Thr Gly Ala Ala Ala Thr Gly Arg Thr
1               5                   10                  15

Arg Val

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct

<400> SEQUENCE: 37

Glu Ala Ala Ala Lys
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Construct

<400> SEQUENCE: 38

Gly Cys Gly Arg Thr
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Thr Gly Ala Ala Ala
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct

<400> SEQUENCE: 40

Leu Arg Pro His Pro
1               5

<210> SEQ ID NO 41
<211> LENGTH: 1273
<212> TYPE: PRT
<213> ORGANISM: SARS-CoV-2

<400> SEQUENCE: 41

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu

```
            165                 170                 175
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590
```

-continued

```
Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
        995                 1000                1005
```

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
                1060                1065                1070

Lys Asn Phe Thr Thr Ala Pro Ala Ile Cys His Asp Gly Lys Ala His
    1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
                1140                1145                1150

Asp Lys Tyr Phe Lys Asn His Thr Ser Pro Asp Val Asp Leu Gly Asp
    1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
                1220                1225                1230

Met Leu Cys Cys Met Thr Ser Cys Cys Ser Cys Leu Lys Gly Cys Cys
                1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270

<210> SEQ ID NO 42
<211> LENGTH: 216
<212> TYPE: PRT
<213> ORGANISM: SARS-CoV-2

<400> SEQUENCE: 42

Met Pro Met Gly Ser Leu Gln Pro Leu Ala Thr Leu Tyr Leu Leu Gly
1               5                   10                  15

Met Leu Val Ala Ser Cys Leu Gly Pro Asn Ile Thr Asn Leu Cys Pro
                20                  25                  30

Phe Gly Glu Val Phe Asn Ala Thr Arg Phe Ala Ser Val Tyr Ala Trp
            35                  40                  45

Asn Arg Lys Arg Ile Ser Asn Cys Val Ala Asp Tyr Ser Val Leu Tyr
    50                  55                  60

Asn Ser Ala Ser Phe Ser Thr Phe Lys Cys Tyr Gly Val Ser Pro Thr
65                  70                  75                  80

Lys Leu Asn Asp Leu Cys Phe Thr Asn Val Tyr Ala Asp Ser Phe Val
                85                  90                  95

Ile Arg Gly Asp Glu Val Arg Gln Ile Ala Pro Gly Gln Thr Gly Lys
                100                 105                 110

Ile Ala Asp Tyr Asn Tyr Lys Leu Pro Asp Asp Phe Thr Gly Cys Val
            115                 120                 125

Ile Ala Trp Asn Ser Asn Asn Leu Asp Ser Lys Val Gly Gly Asn Tyr
        130                 135                 140

Asn Tyr Leu Tyr Arg Leu Phe Arg Lys Ser Asn Leu Lys Pro Phe Glu
145                 150                 155                 160

Arg Asp Ile Ser Thr Glu Ile Tyr Gln Ala Gly Ser Thr Pro Cys Asn
                165                 170                 175

Gly Val Glu Gly Phe Asn Cys Tyr Phe Pro Leu Gln Ser Tyr Gly Phe
            180                 185                 190

Gln Pro Thr Asn Gly Val Gly Tyr Gln Pro Tyr Arg Val Val Val Leu
        195                 200                 205

Ser Phe Glu Leu Leu His Ala Pro
    210                 215

<210> SEQ ID NO 43
<211> LENGTH: 267
<212> TYPE: PRT
<213> ORGANISM: SARS-CoV-2

<400> SEQUENCE: 43

Met Phe Val Phe Leu Val Leu Leu Pro Leu Val Ser Ser Gln Cys Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Trp
        195                 200                 205

Tyr Ile Trp Leu Gly Phe Ile Ala Gly Leu Ile Ala Ile Val Met Val
    210                 215                 220

Thr Ile Met Leu Cys Cys Met Thr Ser Cys Cys Ser Cys Leu Lys Gly
225                 230                 235                 240

Cys Cys Ser Cys Gly Ser Cys Cys Lys Phe Asp Glu Asp Asp Ser Glu
                245                 250                 255

Pro Val Leu Lys Gly Val Lys Leu His Tyr Thr
            260                 265

```
                    260                 265

<210> SEQ ID NO 44
<211> LENGTH: 192
<212> TYPE: PRT
<213> ORGANISM: SARS-CoV-2

<400> SEQUENCE: 44

Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
    130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
                180                 185                 190
```

|      | * ** * ** |

TEMPERATURE-BASED TRANSIENT DELIVERY OF NUCLEIC ACIDS AND PROTEINS TO CELLS AND TISSUES

CROSS-REFERENCE TO RELATED APPLICATIONS

This application is a continuation of International Application No. PCT/US2020/067506, filed Dec. 30, 2021, which claims the benefit of U.S. Provisional Application No. 62/992,700, filed Mar. 20, 2020, and U.S. Provisional Application No. 62/955,801, filed Dec. 31, 2019, the disclosures of which are hereby incorporated by reference in their entirety.

SUBMISSION OF SEQUENCE AS ASCII TEXT FILE

The content of the following submission on ASCII text file is incorporated herein by reference in its entirety: a computer readable form (CRF) of the Sequence Listing (file name: 699442001201SEQLIST.TXT date recorded: Aug. 12, 2021, size: 25,620 bytes).

FIELD

The present disclosure relates to methods for transiently activating a temperature-sensitive agent (ts-agent) in one or more cells, for example by contacting one or more cells with a ts-agent and transiently incubating the cells at a permissive temperature for inducing an activity of the ts-agent in the cells. For ex vivo therapeutic strategies, one or more cells are treated with a therapeutic ts-agent ex vivo at the permissive temperature and the cells are subsequently transferred to a subject at the non-permissive temperature (e.g., the subject's normal core body temperature). For in vivo therapeutic strategies, a therapeutic ts-agent is delivered to a subject that is maintained at the permissive temperature, permitting the therapeutic ts-agent to function in vivo for a limited time before the ts-agent is turned off permanently when the subject's core body temperature returns to normal, or when the subject's surface body temperature is raised (e.g., the non-permissive temperature). Alternatively, a therapeutic ts-agent is delivered to a subject and the ts-agent is subsequently transiently activated by lowering the subject's core body temperature to a permissive temperature for inducing an activity of the therapeutic ts-agent in cells of the subject.

BACKGROUND

Delivery of a therapeutic gene product to human cells, tissues, and organs poses a great challenge. For traditional gene therapy, which requires the continuous expression of a gene to supplement the defect of the gene in a patient, this has been achieved by using a viral vector such as a retrovirus, an adenovirus, or an adeno-associated virus. However, an equally important strategy gene therapy involves transient, short-term expression of a gene. For such applications, the persistent expression of a gene is not required and may actually be deleterious to the cells.

For example, CAS9 is a bacterial enzyme that cleaves DNA. It is an important component of CRISPR/CAS9-based gene editing complex, which has been considered for gene therapy. Both guide RNA and CAS9 can be encoded by genes on a single Sendai virus vector (Park et al., 2016). In order to use the gene-editing system therapeutically, vectors containing CRISPR-CAS9 must be introduced into human cells or the human body. However, the continuous expression of CAS9 could cause the introduction of DNA breaks and mutations. Thus, it is desirable to have CAS9 expressed for a short period of time, for example, on the order of hours or a few days, rather than a week or more.

Another application for short-term expression of a gene is for cellular reprogramming. Recently, it has been shown that the ectopic expression of a set of transcription factors can convert cells into therapeutically useful cell types. For example, a set of three transcription factors can convert pancreatic duct cells into insulin-secreting pancreatic beta-cells (Zhou et al., 2008). Another set of transcription factors can convert fibroblast cells into cardiomyocytes (Ieda et al., 2010). It is thought that in vivo delivery of these transcription factors into the human body could be used as one type of regenerative medicine. However, it is desirable to have these potent cell identity-changing transcription factors expressed only transiently, as the continuous expression of these potent transcription factors may cause harm.

As the above examples highlight, traditional gene therapy using viral vectors that lead to the continuous expression of a gene can be undesirable. For time-limited expression of a gene product, the delivery of synthetic or in vitro-transcribed mRNA into cells has begun to be used (Warren et al., 2010). However, there are several problems with these methodologies. For example, the amount of mRNA delivered to cells, tissues, and organs is limited, and thus, the amount of protein product may not be sufficient for biologically meaningful effects in vivo.

Also, due to the fast turn-over of RNA, which normally lasts for only up to 12 hours (Warren et al., 2010; Goparaju et al., 2017), synthetic RNA must be transfected into cells multiple times. For the forced differentiation of human pluripotent stem cells such as embryonic stem cells and induced pluripotent stem (iPS) cells, twice-daily transfections over the course of several days are required (Akiyama et al., 2016; Goparaju et al. 2017). To generate iPS cells from human fibroblast cells, daily transfection of a cocktail of synthetic RNAs must continue for more than two weeks (Warren et al., 2010). This is not only cumbersome, but also inefficient.

For the generation of iPS cells, this issue has been addressed by using self-replicating RNA, which enables long-term expression after only one delivery (Yoshioka et al., 2013). Self-replicating RNAs are single-stranded RNAs that are usually produced from alphaviruses (Jose et al., 2009), such as Venezuelan Equine Encephalitis Virus (VEEV), Sindbis Virus (SINV), and Semliki Forest Virus (SFV), by removing DNA encoding structural proteins that are required for virus particle formation (Petrakova et al., 2005). Self-replicating RNAs encode nonstructural proteins (nsPs), which function as an RNA-dependent RNA polymerase to replicate the self-replicating RNA itself and to produce a transcript for translation. Self-replicating RNAs can also include a gene of interest (GOI) encoding a protein of interest, and other genetic elements. Due to its positive feedback production of RNAs, self-replicating RNAs can express the GOI at a high level. Self-replicating RNAs can be delivered to mammalian cells as a naked RNA (i.e., a synthetic RNA) or as a virus particle, which can be generated by supplementing the missing virus structural proteins by packaging helper cells.

The advantage of self-replicating RNA vectors are their self-replicating feature, which results in enhancement of expression levels of a GOI. However, one of the drawbacks of self-replicating RNA vectors to deliver RNA/protein to mammalian cells is their persistent expression. Usually, a positive feedback production of an RNA-dependent RNA polymerase and a GOI continues, which may result in the death of cells transfected with a naked RNA form of the self-replicating RNA or infected with a viral form of the self-replicating RNA.

Thus, what is needed in the art of gene therapy are tools for the transient expression of a GOI encoding a protein of interest, such as a therapeutic agent or a foreign antigen (e.g., antigen of a pathogen). In particular, control of transcription and translation of RNA vectors and self-replicating RNA is desirable.

SUMMARY

Based on the necessity of having time-limited expression of a gene of interest (GOI), a transient gene product delivery system is required, where a nucleic acid or protein can be delivered to or expressed in specific cells, in vitro or in vivo, where the amount of nucleic acid/protein is sufficient to have a biologically meaningful effect, and where transient expression can be turned off permanently after achieving the biologically meaningful effect. In order to meet these and other needs, the present disclosure relates to methods for transiently inducing an activity of a temperature-sensitive agent (ts-agent) such as a therapeutic ts-agent, either in a subject (in vivo) or in cells in culture (ex vivo). In some embodiments, the therapeutic ts-agent is used in combination with mild therapeutic hypothermia. In other embodiments, the therapeutic ts-agent is used in combination with mild therapeutic hyperthermia, or a localized application of heat. In some embodiments, the ts-agent is a ts-RNA molecule or ts-protein molecule. In some embodiments, the ts-agent is encoded by a heterologous nucleic acid inserted in a temperature-sensitive viral vector or a self-replicating RNA. In some embodiments, the viral vector is selected from but not limited to a Sendai virus vector, a retrovirus vector, an adeno virus vector, an adeno-associated virus vector, and an Alpha virus vector. In some embodiments, the self-replicating RNA comprises an Alphavirus replicon lacking a viral structural protein coding region. In some embodiments, the Alphavirus is selected from but not limited to a Venezuelan equine encephalitis virus, a Sindbis virus, and a Semliki Forrest virus. In some embodiments, the gene product of interest is not ZSCAN4.

The foregoing and other objects and features of the disclosure will become more apparent from the following detailed description, which proceeds with reference to the accompanying figures.

BRIEF DESCRIPTION OF THE DRAWINGS

FIGS. 1A-1D depict the structure of the Venezuelan Equine Encephalitis Virus (VEEV) genome and locations of mutated regions. FIG. 1A shows a schematic representation of a wild type VEEV genome (TC-83 strain: complete genome 11,446 bp linear RNA: NCBI Accession: L01443.1 GI: 323714). Genes of nonstructural proteins (nsP1, nsP2, nsP3, nsP4) encode RNA-dependent RNA polymerase and genes of structural proteins encode viral envelope proteins (C, E1, E2). 5'-UTR (5'-untranslated region) and 3'-UTR (3'-untranslated region). The gene of the nsP2 protein, presented as a bold box, was mutated to produce temperature sensitivity. FIG. 1B shows a schematic representation of nsP2 with mutation 1 (temperature-sensitive mutant 1: ts1). Five amino acids were inserted between amino acids 439 and 440. FIG. 1C shows a schematic representation of nsP2 with mutation 2 (ts2). Five amino acids were inserted between amino acids 586 and 587. FIG. 1D shows a schematic representation of nsP2 with mutation 3 (ts3). Five amino acids were inserted between amino acids 594 and 595.

FIGS. 2A-2C depict partial sequences of VEEV nsP2, corresponding to the regions mutated in ts1, ts2, and ts3. FIG. 2A shows the wild type sequence in comparison to mutant 1 (ts1), which includes a 15 nucleotide insertion resulting in a 5 amino acid insertion. FIG. 2B shows the wild type sequence in comparison to mutant 2 (ts2), which includes a 15 nucleotide insertion resulting in a 5 amino acid insertion. FIG. 2C shows the wild type sequence in comparison to mutant 3 (ts3), which includes a 15 nucleotide insertion resulting in a 5 amino acid insertion.

FIG. 3 depicts partial nucleotide sequences for VEEV nsP1 of wild type (TC-83 strain) and mutant 4 (ts4), set forth as SEQ ID NO:19 and SEQ ID NO:20, respectively. The 5'-UTR and the 51-nt CSE (conserved sequence element) are shown in bold. Mutated nucleotides in ts4 are underlined.

FIGS. 4A and 4B depict testing temperature-sensitivity of srRNA1ts2 and srRNA1ts3 at 30° C., 32° C., and 37° C. Wild type (srRNA1 wt-GFP) and mutant (srRNA1ts2-GFP, srRNA1ts3-GFP) self-replicating RNA (srRNA) vectors were generated. RNAs produced by in vitro transcription were transfected into human induced pluripotent stem cells (ADSC-iPSC line). Cells were cultured in CO$_2$ incubators maintained at 30° C., 32° C., and 37° C., respectively. Pictures of cells were obtained at 20 hours and 48 hours, respectively. The upper panels show phase-contrast images and the lower panels show fluorescence images detecting expression of green fluorescence protein (GFP). FIG. 4A shows results from transfection of cells with srRNA1wt-GFP, srRNA1ts2-GFP, and srRNA1ts3-GFP RNA. FIG. 4B shows results from transfection of cells with synthetic mRNA encoding GFP (synRNA-GFP).

FIGS. 11A and 11B depict transfections carried out using JetMessenger (Polyplus). Cells were cultured in standard media alone (FIG. 11A) or standard media supplemented with 200 ng/ml of B18R (FIG. 11B). FIGS. 11C and 11D depict transfections carried out using MessengerMax (ThermoFisher). Cells were cultured in standard media alone (FIG. 11C) or standard media supplemented with 200 ng/ml of B18R (FIG. 11D).

FIG. 12 depicts an alignment of amino acid sequences corresponding to nsP2 mutant 2 (ts2) of various alphavirus family members. The left panel depicts an alignment (reproduced in part from FIG. 1 of Russo et al., 2006) of wild type sequences set forth as SEQ ID NOS:21-28, while the right panel depicts an alignment of mutant sequences set forth as SEQ ID NOS:29-36 including an insertion of 5 amino acids between the "β5" and "β6" ($5^{th}$ and $6^{th}$ "β strands) in the secondary structure of nsP2. VEEV (Venezuelan equine encephalitis virus), Aura (Aura virus), WEEV (Western equine encephalitis virus), BFV (Barmah Forest virus), ONNV (O'nyong-nyong virus), RRV (Ross River virus), SFV (Semliki Forest virus), and SINV (Sindbis virus).

C.) for some time (e.g., 24 hours) the ts-agent is functional. Subsequently, the patient's core body temperature is returned to normal temperature (37° C.), at which time the ts-agent is no longer functional.

Figure 17:
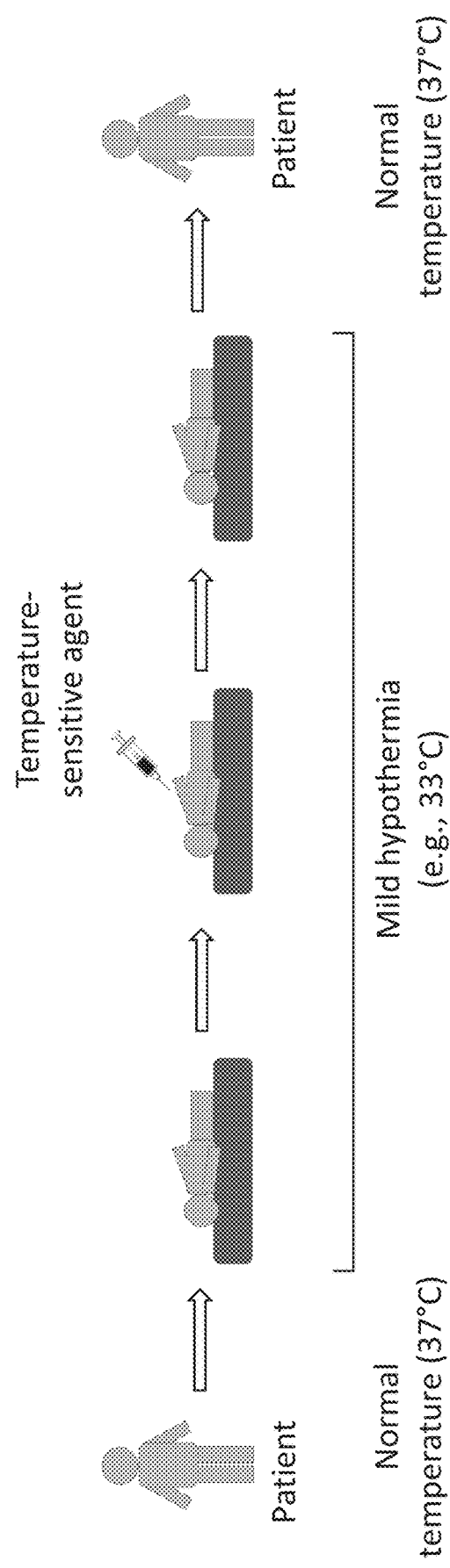

FIG. 17 depicts a schematic diagram showing an exemplary in vivo therapeutic procedure. Temperature-sensitive agents (ts-agents) such as srRNAs or Sendai virus vectors, are functional at a permissive temperature (e.g., 33° C.), but non-functional at a non-permissive temperature (e.g., 37° C.). A patient undergoes a procedure for therapeutic hypothermia and the patient's core body temperature is maintained at a reduced temperature (e.g., 33° C.), which is lower than normal body temperature (e.g., 37° C.). The ts-agent is directly delivered systemically or to specific organs, tissues, or cell types. While the patient is maintained at the reduced temperature (e.g., 33° C.) for some time (e.g., 24 hours), the ts-agent is functional. Subsequently, the patient's core body temperature is returned to normal temperature (37° C.), at which time the ts-agent is no longer functional.

Figure 18:
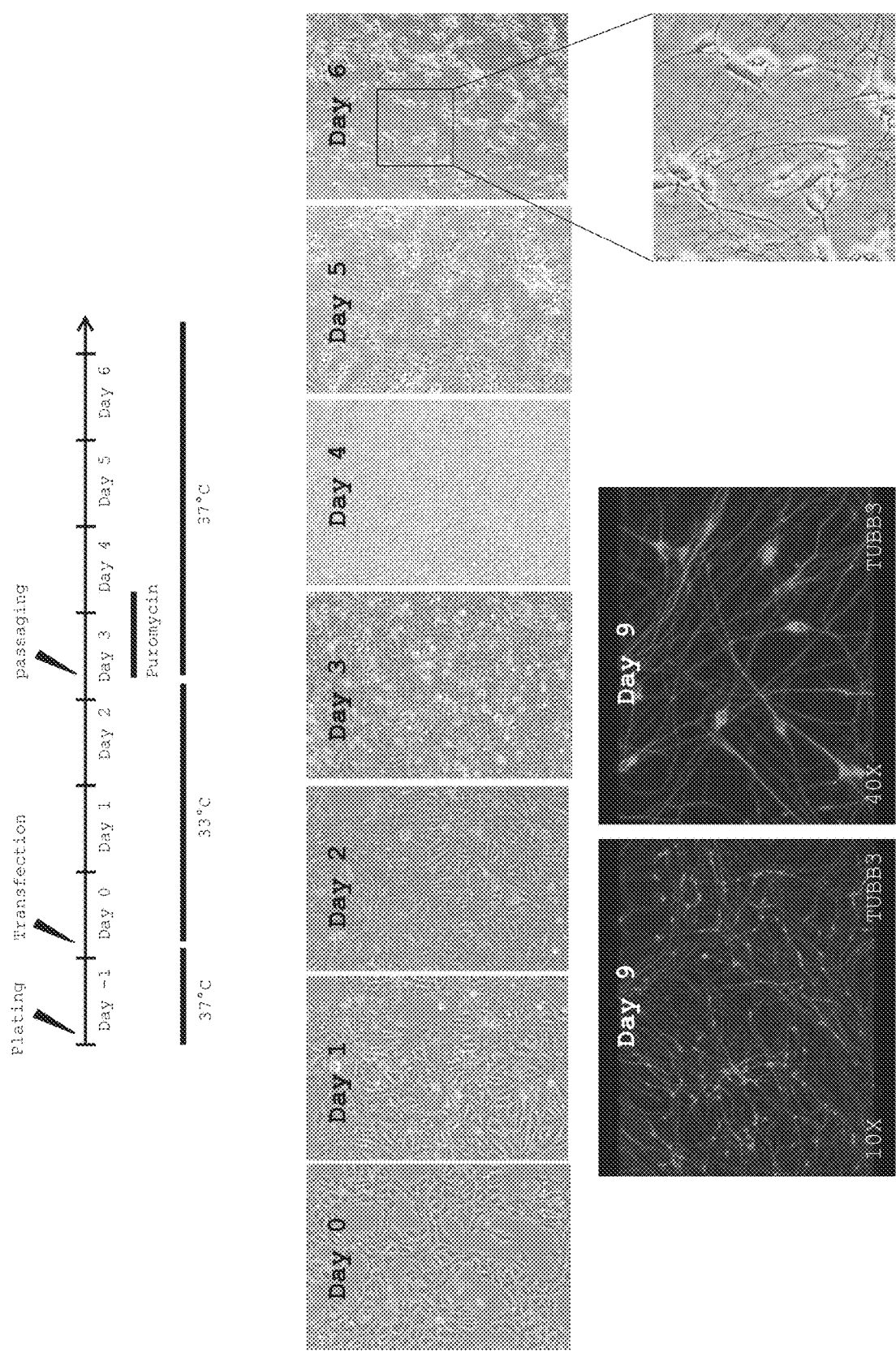

FIG. 18 depicts differentiation of human ES/iPS cells into neurons. A schematic representation of a typical experimental procedure is shown. Human ES/iPS cells were plated onto a cell culture dish on Day −1. On Day 0, cells were transfected with srRNA1ts2-NGN3. Cells were cultured at 33° C. for 72 hours. On Day 3, cells were re-plated onto a new culture dish and then cell cultures were transferred to 37° C. Puromycin was added to the medium on Day 3 for 24 hours. Phase contrast microscopic images were taken on Day 0 (before transfection), 1, 2, 3 (before passaging), 4 (before medium change), 5, and 6. Magnified image of Day 6 picture is also shown. Cells were fixed on Day 9 and used for immunostaining with anti-TUBB3 (beta3-tubulins) (red signals), which is specific to mature neurons (10× and 20× objective lens).

Figure 19:
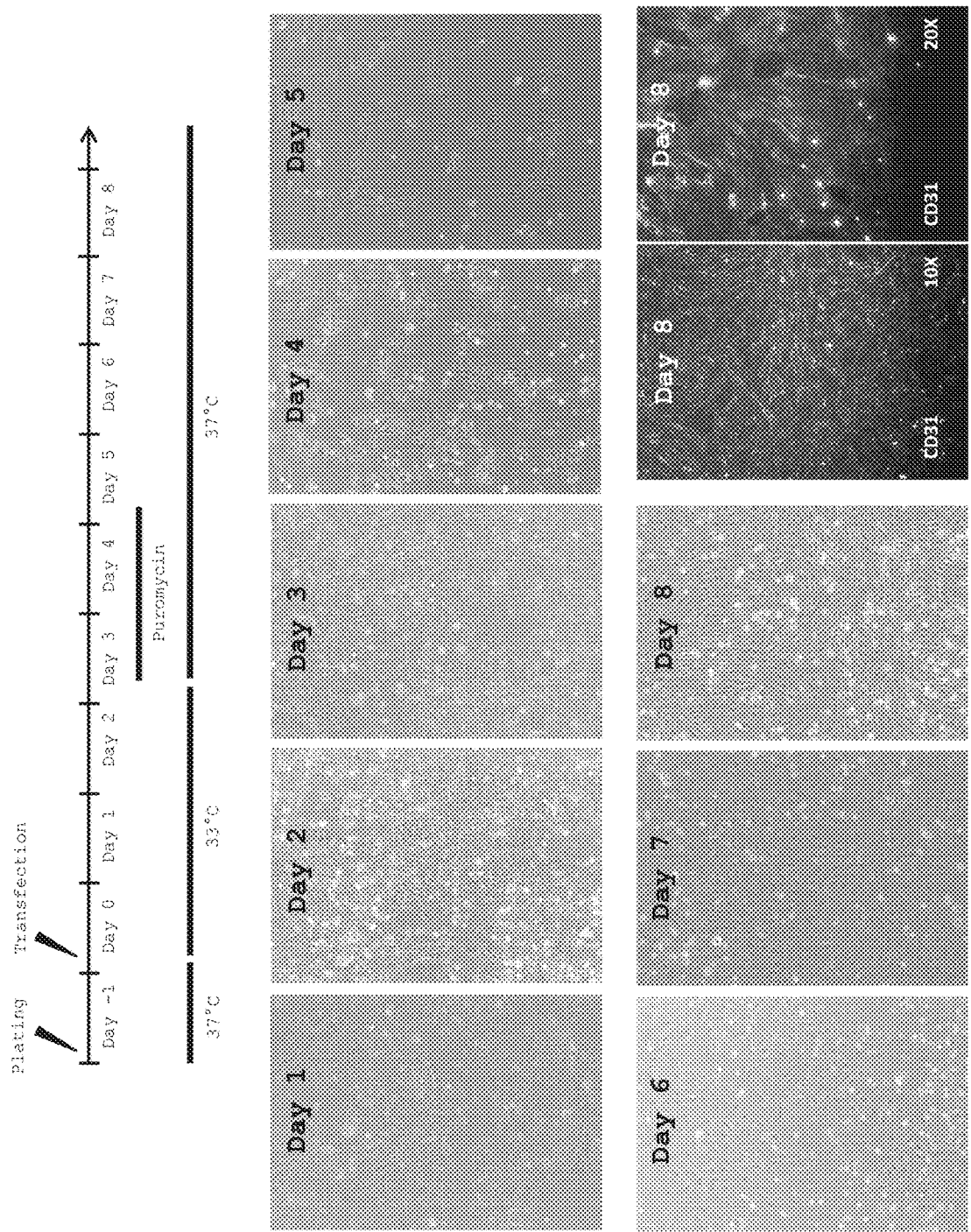

FIG. 19 depicts differentiation of human ES/iPS cells into vascular endothelial cells. A schematic representation of a typical experimental procedure is shown. Human ES/iPS cells were plated onto a cell culture dish on Day −1. On Day 0, cells were transfected with srRNA1ts2-ETV2. Cells were cultured at 33° C. for 72 hours. On Day 3, cell cultures were transferred to 37° C. Puromycin was added to the medium on Day 3 for 48 hours. (Lower Panel) Phase contrast microscopic images were taken on Day 1, 2, 3, 4, 5, 6, 7, and 8. Cells were fixed on Day 8 and used for immunostaining with anti-CD31 (10× and 20× objective lens).

Figure 20:
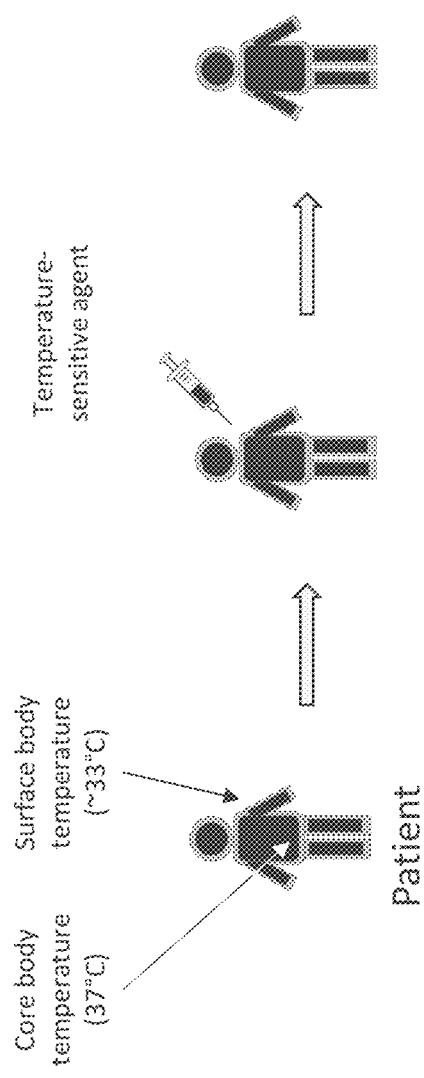

FIG. 20 depicts a schematic diagram showing an exemplary in vivo therapeutic procedure. Temperature-sensitive agents (ts-agents) such as srRNAs or Sendai virus vectors, are functional at a permissive temperature (e.g., 31-34° C.), but non-functional at a non-permissive temperature (e.g., >37° C.). The temperature at or just below the surface of a patient's body (surface body temperature), which is around 31-34° C., is lower than the core body temperature of the patient, which is around 37° C. The ts-agent is directly delivered by intradermal, subcutaneous, or intramuscular administration to a patient, where it is functional at the patient's surface body temperature. No further action is required. Alternatively, when the function of the ts-agent is no longer needed, the ts-agent can be rendered non-functional by transiently increasing the patient's surface body temperature.

Figure 21:
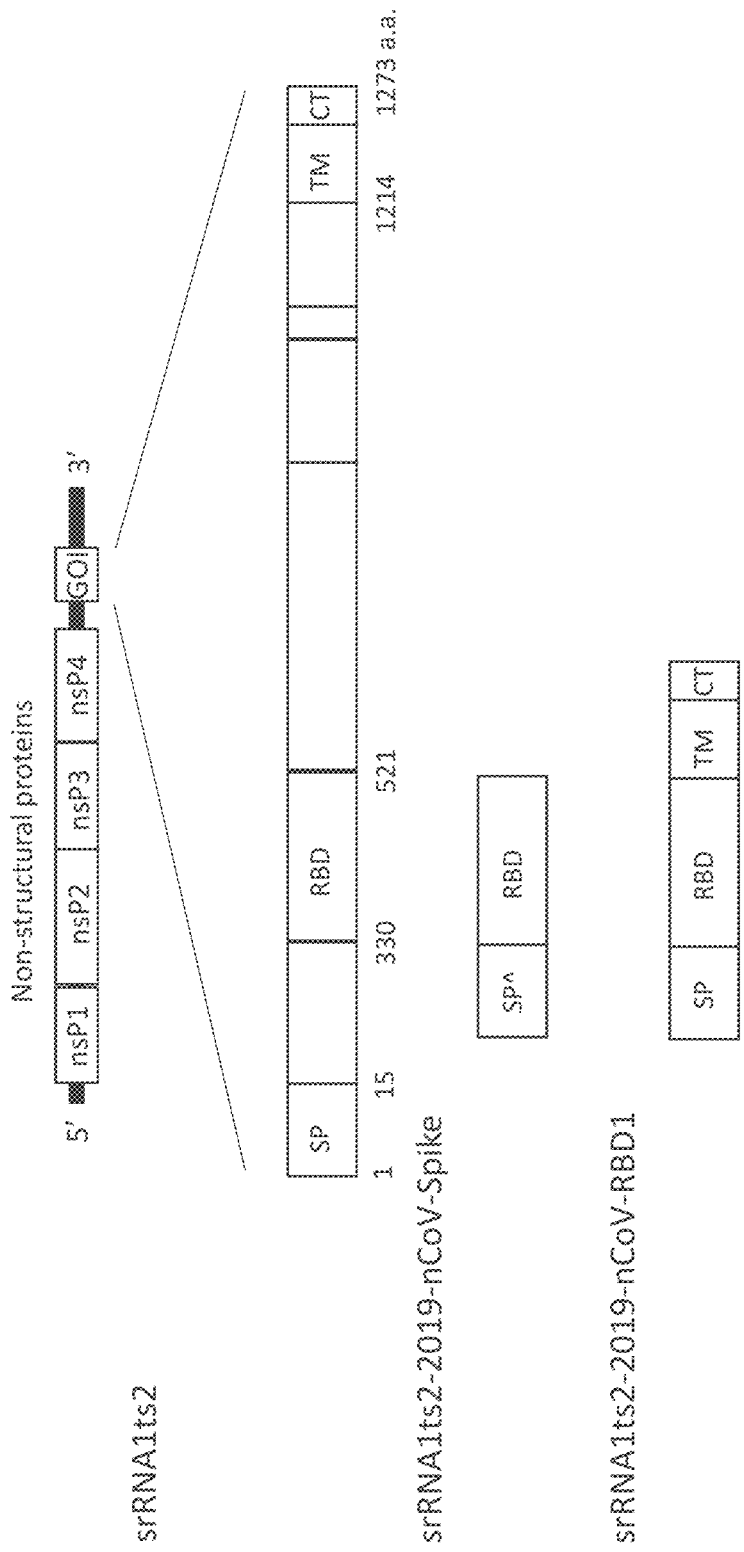

FIG. 21 depicts a schematic diagram showing exemplary srRNA1ts2 vectors encoding the spike protein (or portions thereof) of severe acute respiratory syndrome coronavirus-2 (SARS-CoV-2, also known as 2019-nCoV). SARS-CoV-2 is the causative agent of coronavirus disease 2019 (COVID-2019). Non-structural proteins (nsP1-nsP4) of the srRNA1ts2 vector are required for replication and transcription of the RNA genome, while the gene of interest (GOI) encodes the spike protein or fragment thereof. "srRNA1ts2-2019-nCoV-Spike" encodes the full-length spike protein (SEQ ID NO:41) of 2019-nCoV. "srRNA1ts2-2019-nCoV-RBD1" encodes a fusion protein (SEQ ID NO:42) including the signal peptide of CD5 (residues 1-24) and the RBD of the spike protein of 2019-nCoV. "srRNA1ts2-2019-nCoV-RBD2" encodes a fusion protein (SEQ ID NO:43) including the signal peptide, RBD, transmembrane domain, and cytoplasmic tail of the spike protein of 2019-nCoV. The amino acid sequence of the RBD of 2019-nCoV is set forth as SEQ ID NO:44. Abbreviations: SP (signal peptide); RBD (receptor binding domain); TM (transmembrane domain); and CT (cytoplasmic tail).

Figure 22:
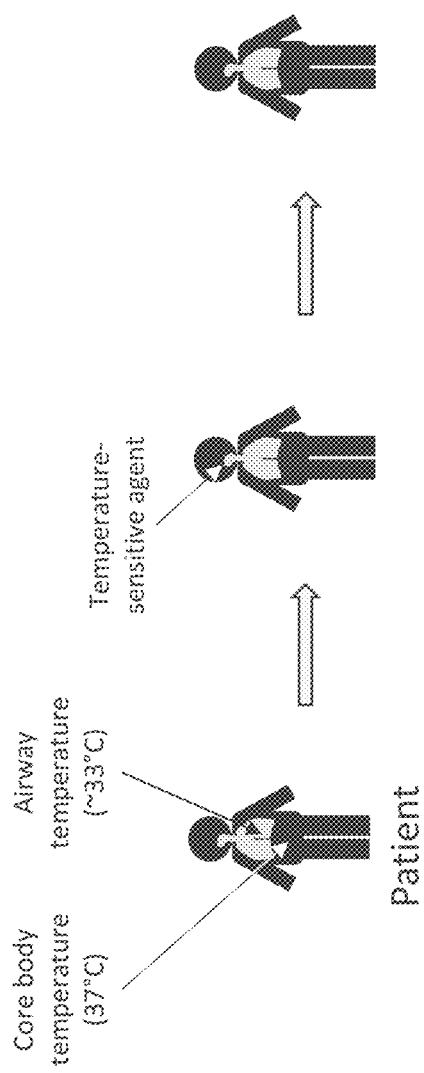

FIG. 22 depicts a schematic diagram showing an exemplary in vivo therapeutic procedure. Temperature-sensitive agents (ts-agents) such as srRNAs or Sendai virus vectors, are functional at a permissive temperature (e.g., 31-35° C.), but non-functional at a non-permissive temperature (e.g., >37° C.). The temperature of airways of a patient's body (airway temperature), which is around 32° C. for nasal cavity and upper trachea, and 35° C. for subsegmental bronchi (McFadden et al., 1985), is lower than the core body temperature of the patient, which is around 37° C. The ts-agent is directly delivered by nasal administration (e.g., insufflation, inhalation or instillation) to a patient, where it is functional at the patient's airway temperature. No further action is required. When the function of the ts-agent is no longer needed, the ts-agent can be rendered non-functional by transiently increasing the patient's airway temperature.

Figure 23:
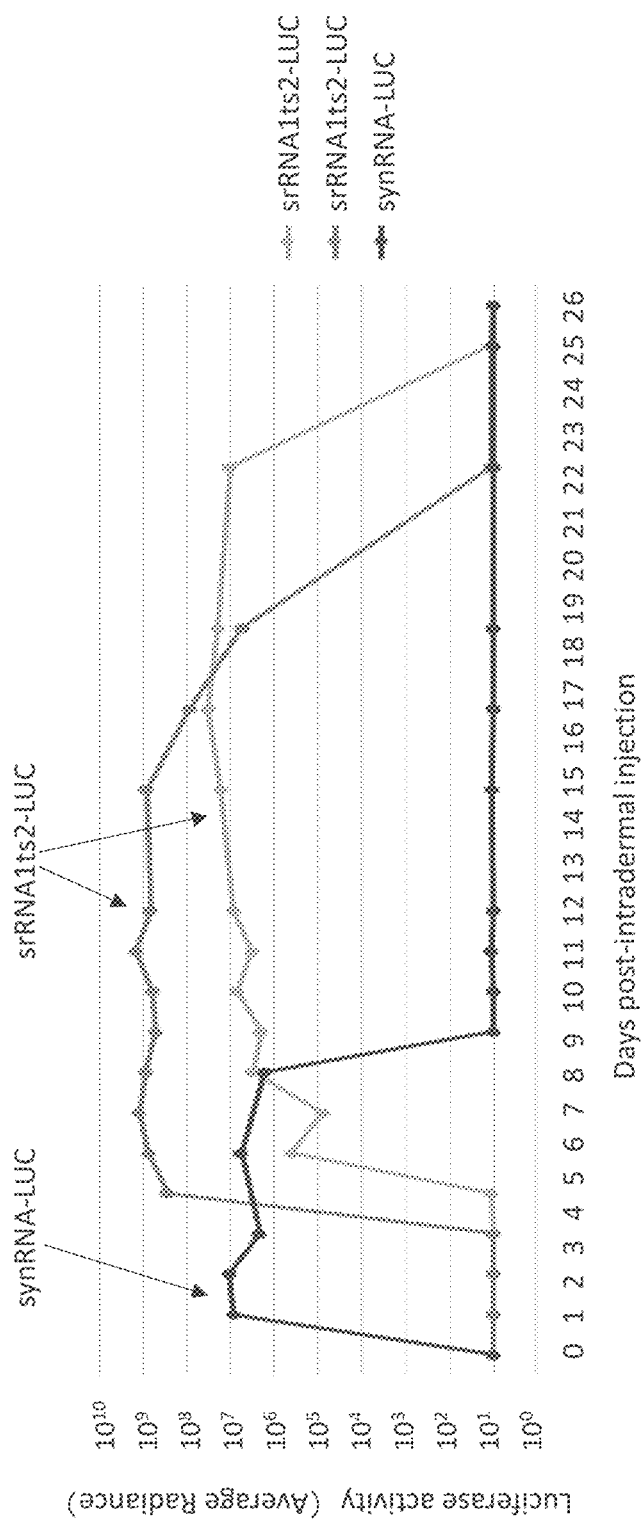

FIG. 23 depicts expression of a gene of interest in vivo as a consequence of intradermal administration of RNA encoding the gene of interest (luciferase) to hind limbs of outbred mice.

Figures 24A, 24B:
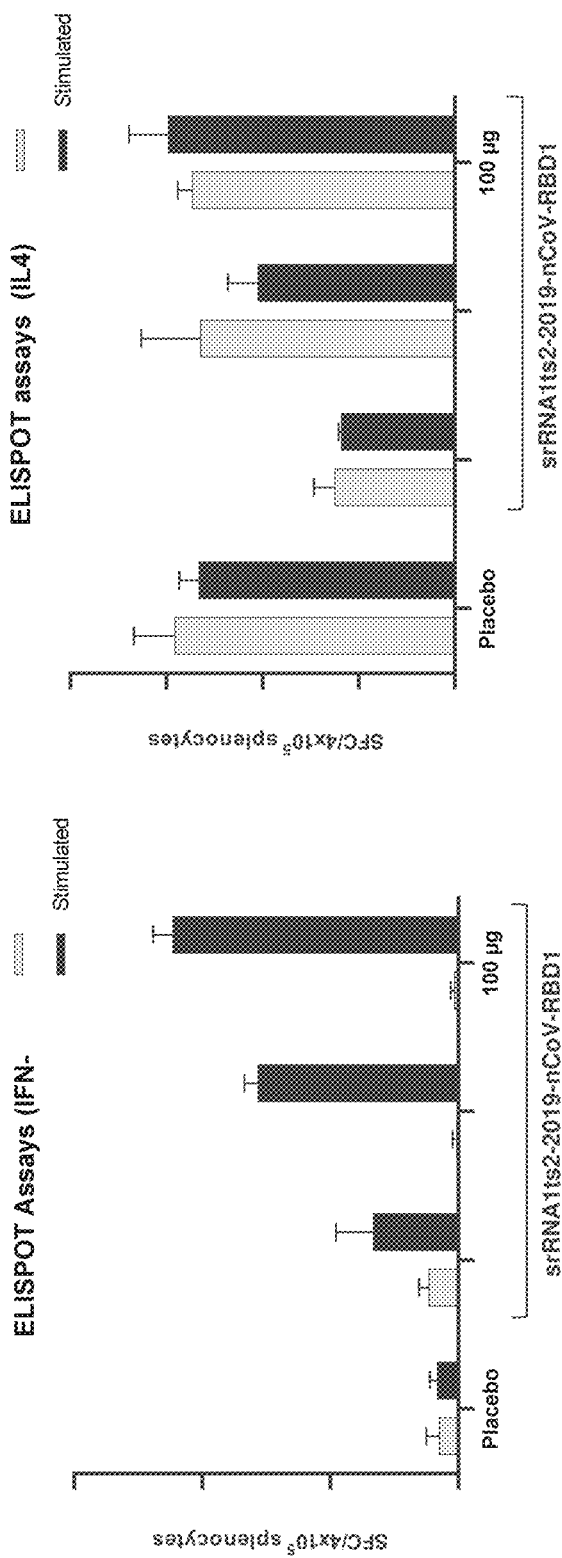

FIGS. 24A-24B show the frequency of cytokine-secreting cells in samples of splenocytes obtained from mice that had been immunized by intradermal injection of a temperature-sensitive srRNA1ts2 RNA encoding a receptor binding domain (RBD) of SARS-CoV-2 (srRNA1ts2-2019-CoV-RBD1) or a placebo (buffer only). FIG. 24A shows the frequency of interferon-gamma (INF-7) spot-forming cells (SFC) and FIG. 24B shows the frequency of interleukin-4 (IL-4) SFC in splenocytes from immunized mice cultured in the presence and absence of SARS-CoV-2 antigen as determined by ELISpot assays. Black bars (Stimulated) represent the splenocytes stimulated by a pool of 53 peptides (15mers with 11 amino acid overlaps) that covers SARS-CoV-2 RBD for 24 hours. Gray bars (Control) represent the splenocytes without the stimulation. The average and standard deviation (error bars) of triplicate samples are shown.

Figures 25A, 25B, 25C:
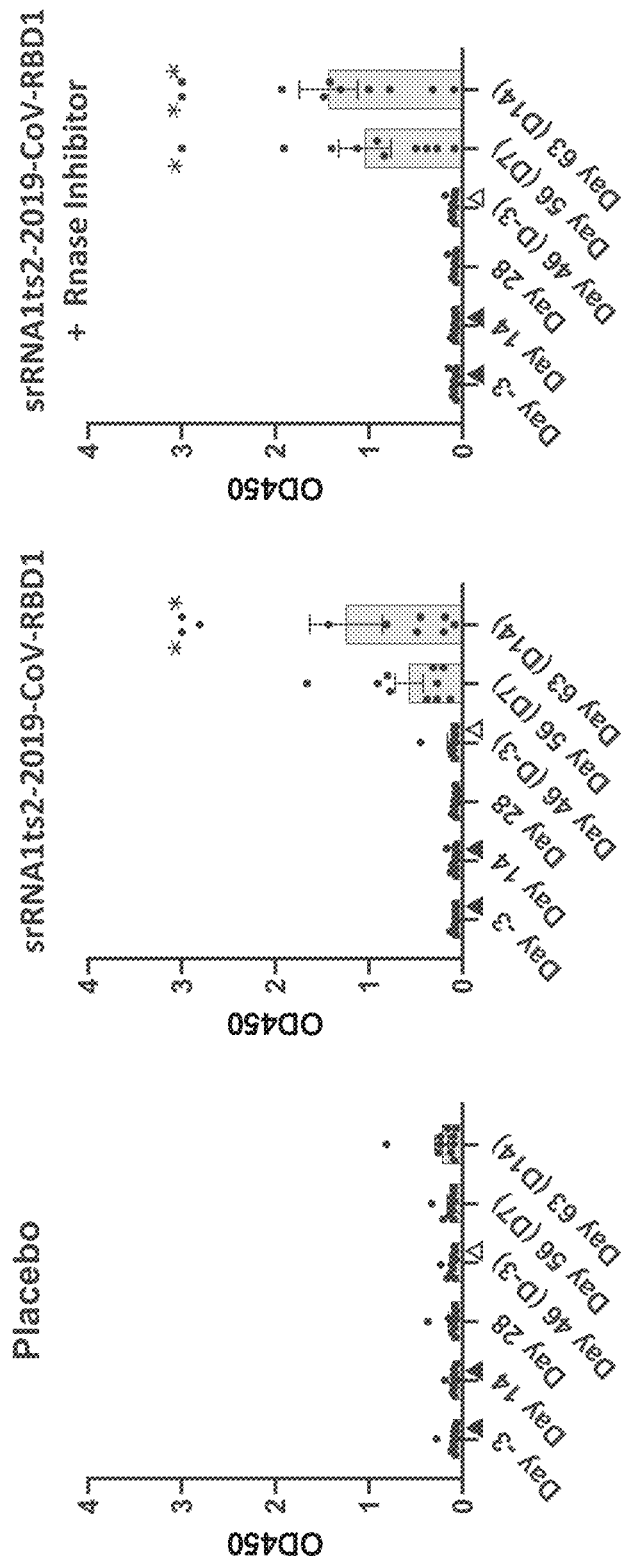

FIGS. 25A-25C show the levels of SARS-CoV-2 antigen-reactive serum immunoglobulin G (IgG) of mice that had been immunized by intradermal injection of a temperature-sensitive srRNA1ts2 RNA encoding a receptor binding domain (RBD) of SARS-CoV-2 (srRNA1ts2-2019-CoV-RBD1) or a placebo (buffer only). In brief, on Day 0 and Day 14, mice received a placebo, or srRNA1ts2-2019-CoV-RBD1 in the presence and absence of an RNase inhibitor (black triangles). On Day 49, all mice received a recombinant RBD protein (open triangles). Asterisk (*) indicates IgG levels higher than 3 (OD450). FIG. 25A shows results of mice that received two doses of a placebo (buffer only). FIG. 25B shows results of mice that received two doses of srRNA1ts2-2019-CoV-RBD1 RNA. FIG. 25C shows results of mice that received two doses of srRNA1ts2-2019-CoV- RBD1 RNA in combination with a RNase inhibitor. Asterisk (*) indicates IgG levels higher than 3 (OD450). N=10 in all groups.

DETAILED DESCRIPTION

Overview

Applicant has demonstrated that cells can be cultured at a permissive temperature for inducing an activity of a temperature-sensitive therapeutic agent, and that the activity can lead to a therapeutic effect in the cells. Moreover, the activity of the temperature-sensitive therapeutic agent can be reduced or inhibited by subsequently incubating the cells at a non-permissive temperature. Applicant has also for the first time provided methods for use of temperature-sensitive agents (ts-agents) in vivo. The same types of ts-agents used in vitro can be used in vivo. For instance, after administration of a ts-agent to the core of a subject, the subject's core body temperature can be lowered to a permissive temperature for inducing an activity of the ts-agent. Alternatively, after administration of a ts-agent to the surface (epidermis, dermis, hypodermis, or skeletal muscle) of a subject, the subject's surface body temperature is maintained at a permissive temperature for inducing an activity of the ts-agent. The subject's surface body temperature may be maintained naturally or artificially. These methods provide new ways to deliver and transiently activate therapeutic agents such as nucleic acids and polypeptides. In particular, the present disclosure provides tools for temperature-sensitive delivery of nucleic acids and proteins to cells, with the proviso that the nucleic acids and proteins are not ZSCAN4 nucleic acids and proteins.

Accordingly, the present disclosure generally relates to methods of transiently inducing an activity of a temperature-sensitive agent (e.g., a temperature-sensitive therapeutic agent) in vitro. In some embodiments, one or more cells comprising a temperature-sensitive therapeutic agent are cultured at a permissive temperature for inducing an activity of the temperature-sensitive therapeutic agent. The cells are cultured at the permissive temperature for a period of time sufficient for the temperature-sensitive therapeutic agent to induce a therapeutic effect in the cells. The cells are then returned to a non-permissive temperature, wherein the non-permissive temperature reduces or inhibits an activity of the temperature-sensitive therapeutic agent. In another embodiment, the one or more cells do not already comprise a temperature-sensitive therapeutic agent, and are first contacted with a temperature-sensitive therapeutic agent. In some embodiments, after inducing a therapeutic effect in the one or more cells, the cells are administered to a subject in need thereof. In some embodiments, the one or more cells are isolated from a subject in need of treatment and after treating with a temperature-sensitive therapeutic agent, the cells are returned to said subject.

In another aspect, the present disclosure relates to methods of transiently inducing an activity of a temperature-sensitive agent (e.g., a temperature-sensitive therapeutic agent) in vivo. In some embodiments, one or more cells in a subject comprise a temperature-sensitive therapeutic agent, and the subject's body temperature is lowered to a permissive temperature for a period of time sufficient for the temperature-sensitive therapeutic agent to induce a therapeutic effect in the cells, and the subject's body temperature is then returned to normal body temperature. In another embodiment, the temperature-sensitive therapeutic agent is administered to the subject, either before or after the subject's body temperature is lowered to a permissive temperature.

Other aspects of the present disclosure relate to treating a disease or condition by mobilizing bone marrow cells in a subject suffering from a disease or condition, the method comprises: isolating the mobilized bone marrow cells from the subject, culturing the isolated bone marrow cells at a temperature of about 33° C.±0.5° C., contacting said cells with a temperature-sensitive viral vector, such as Sendai viral vector, or a temperature-sensitive self-replicating RNA (srRNA), wherein the viral vector or the srRNA comprises a heterologous nucleic acid molecule, maintaining the contacted cells at about 33° C.±0.5° C. for a sufficient period of time, wherein the viral vector or the srRNA is capable of replicating at 33° C.±0.5° C. and replication of the viral vector or the srRNA leads to increased expression of the heterologous nucleic acid molecule, and engrafting the contacted cells into the subject to treat the disease or condition. Alternatively, after isolating the mobilized bone marrow cells from the subject, the isolated bone marrow cells are contacted with a temperature-sensitive viral vector, such as Sendai viral vector, or a temperature-sensitive srRNA before culturing the cells at a temperature of about 33° C.±0.5° C.

In another aspect, the present disclosure relates to treating a disease or condition by administering to a subject in need thereof a temperature-sensitive viral vector, such as Sendai viral vector, or a temperature-sensitive self-replicating RNA (srRNA), wherein the viral vector or the srRNA comprises a heterologous nucleic acid, lowering the subject's core body temperature to about 33° C.±0.5° C., maintaining the subject's core body temperature at about 33° C.±0.5° C. for a sufficient period of time, wherein the viral vector or the srRNA is capable of replicating at 33° C.±0.5° C. and replication of the viral vector or the srRNA leads to increased expression of the heterologous nucleic acid molecule, and allowing the subject's core body temperature to return to normal. Alternatively, lowering the subject's core body temperature to about 33° C.±0.5° C. is done prior administering a temperature-sensitive viral vector, such as Sendai viral vector, or a temperature-sensitive srRNA.

References and claims to methods for treating a disease or condition by administering a ts-agent or cells comprising the ts-agent to a subject, in their general and specific forms likewise related to:

a) the use of a ts-agent or cells comprising the ts-agent for the manufacture of a medicament for the treatment of a disease or condition; and b) pharmaceutical compositions comprising a ts-agent or cells comprising the ts-agent for the treatment of a disease or condition.

In some embodiments of the methods of the proceeding paragraphs, the heterologous nucleic acid comprises a gene of interest (GOI) or encodes a protein of interest. In preferred embodiments, the protein of interest is a therapeutic agent. In some embodiments, the GOI is a dominant-negative form of the GOI, or an artificial gene encoding an artificial protein (e.g., hybrid protein made by fusing different protein domains). In some embodiments, the heterologous nucleic acid comprises a non-coding RNA, an siRNA, or an shRNA. In other embodiments, the heterologous nucleic acid comprises an endonuclease editing system. In some embodiments, the endonuclease editing system is selected from but not limited to a ZFN system, a TALENs system, and a CRISPR/CAS9 system. In some embodiments, the protein of interest is selected from but not limited to human neurogenin-3 (NGN3), human ETS translocation variant 2 (ETV2), brain-derived neurotrophic factor (BDNF) and nerve growth factor (NGF). In some embodiments, the protein of interest is erythropoietin (EPO) or granulocyte colony stimulating factor (G-CSF). In other embodiments, the protein of interest is an enzyme, such as adenosine deaminase (ADA), for enzyme replacement therapy. In some embodiments, the protein of interest is an antigen encoded by a pathogenic organism, such as a virus, a protozoan, or a bacteria, for the purpose of vaccination against an infectious disease.

Definitions

As used herein and in the appended claims, the singular forms "a," "an" and "the" include plural forms unless otherwise indicated. For example, "a polynucleotide" includes one or more polynucleotides.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting of" and "consisting essentially of" embodiments.

The term "about" as used herein in reference to a value other than temperature, encompasses from 90% to 110% of that value (e.g., about 30 minutes refers to 27 min to 33 min), unless otherwise indicated. When use in reference to temperature in Celsius, about encompasses −1° C. to +1° C. of that value (e.g., about 37° C. refers to 36° C. to 38° C.), unless otherwise indicated. In contrast, the use of plus or minus without more, delineates the indicated range (e.g., 33° C.±0.5° C. refers to 32.5° C. to 33.5° C.).

As used herein, numerical ranges are inclusive of the numbers defined the range (e.g., 12-18 nucleotides encompasses 12, 13, 14, 15, 16, 17 and 18 nucleotides).

The terms "isolated" and "purified" as used herein refers to an object (e.g., a cell) that is removed (e.g., separated) from its environment (e.g., cell culture, biological sample, etc.). "Isolated" objects are at least 50% free, preferably 75% free, more preferably at least 90% free, and most preferably at least 95% (e.g., 95%, 96%, 97%, 98%, or 99%) free from other components with which they are associated.

The terms "individual" and "subject" refer to mammals. "Mammals" include, but are not limited to, humans, non-human primates (e.g., monkeys), farm animals, sport animals, rodents (e.g., mice and rats) and pets (e.g., dogs and cats).

The term "dose" as used herein in reference to a pharmaceutical composition refers to a measured portion of the composition taken by (administered to or received by) a subject at any one time.

The term "treating" a disease or a condition refer to executing a protocol, which may include administering one or more pharmaceutical compositions to an individual (human or other mammal), in an effort to alleviate signs or symptoms of the disease. Thus, "treating" or "treatment" does not require complete alleviation of signs or symptoms, does not require a cure, and specifically includes protocols that have only a palliative effect on the individual. As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total).

"Stimulating" an immune response, means increasing the immune response, which can arise from eliciting a de novo immune response (e.g., as a consequence of an initial vaccination regimen) or enhancing an existing immune response (e.g., as a consequence of a booster vaccination regimen). In some embodiments, stimulating an immune response includes but is not limited to one or more of the group consisting of: stimulating CD4+T helper cell proliferation; stimulating cytokine production; stimulating B lymphocyte proliferation; stimulating antibody production; stimulating CD8+ cytotoxic T cell proliferation; and stimulating cytolysis of infected cells. In some preferred embodiments, stimulating an immune response comprises increasing an antigen-specific antibody response in the subject. Preferably, increasing the antigen-specific antibody response comprises increasing the concentration of antigen-specific antibodies at least 2, 3 or 4 fold higher than a pre-administration level. In some embodiments, increasing the antigen-specific antibody response comprises increasing the concentration of antigen-specific antibodies above a minimum level, preferably above a seroprotective level.

Temperature-Sensitive Agents

Certain aspects of the present disclosure relate to transiently inducing an activity of a temperature-sensitive agent (e.g., a temperature-sensitive therapeutic agent) in one or more cells. An activity of the temperature-sensitive agent refers to any desired activation, replication, or increased expression of the agent. As used herein, the term "temperature-sensitive agent" refers to any nucleic acid or polypeptide that has different levels of functionality at different temperatures. Exemplary temperature-sensitive agents include, without limitation, temperature-sensitive viral vectors, temperature-sensitive self-replicating RNAs, and temperature-sensitive polypeptides.

As used herein, the term "permissive temperature" refers to any temperature at which the activity of a temperature-sensitive agent of the present disclosure is induced. Typically, a permissive temperature is not the normal body temperature of a subject. The normal body temperature of a human subject is about 37° C.±0.5° C. Depending on the temperature-sensitive agent, a permissive temperature may be a temperature that is higher or lower than the normal body temperature of a subject. In some aspects, the permissive temperature for the temperature-sensitive agent ranges from 30° C. to 36° C. In some embodiments, the permissive temperature is from about 31PC to about 35° C., or 32° C. to 34° C. (33° C.±1.0° C.). In some preferred embodiments, the permissive temperature is 33° C.±0.5° C. It follows that in some embodiments, the non-permissive temperature for the temperature-sensitive self-replicating RNAs of the present disclosure is above 36° C. In some preferred embodiments, the non-permissive temperature is 37° C.±0.5° C.

In some embodiments, the activity of the temperature-sensitive agent induced at a permissive temperature is reduced or inhibited at a non-permissive temperature. The term "non-permissive temperature", as used herein, refers to any temperature at which an activity of a temperature-sensitive agent of the present disclosure is not induced. A temperature-sensitive agent is not induced when an activity of the temperature-sensitive agent is at least 95% less, at least 90% less, at least 85% less, at least 80% less, at least 75% less, or at least 50% less than the level of activity at the optimal permissive temperature. Typically, a non-permissive temperature is the normal body temperature of a subject. Depending on the temperature-sensitive agent, a non-permissive temperature may also be a temperature that is higher or lower than the normal body temperature of a subject.

Temperature-Sensitive Viral Vectors

In certain embodiments, a temperature-sensitive therapeutic agent of the present disclosure may comprise a temperature-sensitive viral vector. In some embodiments, an activity of the temperature-sensitive viral vector induced at a permissive temperature may include replication of the vector. As used herein, the term "temperature-sensitive viral vector" refers to any viral vector that has different levels of functionality at different temperatures. Exemplary temperature-sensitive viral vectors include, without limitation, Sendai virus vectors, Adeno associated virus vectors, retrovirus vectors, or alphavirus vectors. Exemplary temperature-sensitive alphavirus vectors include, without limitation, Venezuelan Equine Encephalitis virus vectors, Sindbis virus vectors, and Semliki Forrest virus vectors.

In some embodiments of the present disclosure, a temperature-sensitive viral vector comprises a heterologous nucleic acid (e.g., foreign nucleic acid in relation to the viral vector). A nucleic acid may comprise a genetic element. As used herein, the term "genetic element" refers to any nucleic acid that encodes an RNA or polypeptide of interest. Exemplary genetic elements include, without limitation, a gene of interest (GOI), a dominant-negative form of a gene of interest, an artificial gene that encodes an artificial protein such as a hybrid protein made by fusing different protein domains, a non-coding RNA, an siRNA, an shRNA, and an endonuclease editing system. In some embodiments, the endonuclease editing system is selected from a ZFN system, a TALENs system, and a CRISPR/CAS9 system. In some embodiments, the GOI encodes a protein selected from but not limited to human neurogenin-3 (NGN3), human ETS translocation variant 2 (ETV2), brain-derived neurotrophic factor (BDNF) and nerve growth factor (NGF). In some embodiments, the protein of interest is erythropoietin (EPO) or granulocyte colony stimulating factor (G-CSF). In other embodiments, the protein of interest is an enzyme, such as adenosine deaminase (ADA), for enzyme replacement therapy. In some embodiments, the protein of interest is an antigen encoded by a pathogenic organism, such as a virus, a protozoan, or a bacteria, for the purpose of vaccination against an infectious disease.

The permissive temperature for the temperature-sensitive viral vectors of the present disclosure typically ranges from 30° C. to 36° C. or from 38° C. to 50° C. In some embodiments, the permissive temperature is from about 31° C. to about 35° C., or 32° C. to 34° C. (33° C.±1.0° C.). In some preferred embodiments, the permissive temperature is 33° C.±0.5° C. It follows that in some embodiments, the non-permissive temperature for the temperature-sensitive viral vectors of the present disclosure is above 36° C. and below 38° C. In some preferred embodiments, the non-permissive temperature is 37° C.±0.5° C.

As disclosed herein, cells may be maintained at a permissive temperature for a period of time sufficient for the temperature-sensitive agent to induce an effect. In some embodiments, a temperature-sensitive viral vector comprises a genetic element, and an effect includes increased expression of the genetic element, wherein expression of the genetic element results in production of an RNA or polypeptide that creates a biological effect in the cells. In some preferred embodiments, the effect is a therapeutic effect.

Temperature-Sensitive Self-Replicating RNAs

In certain embodiments, a temperature-sensitive therapeutic agent of the present disclosure may comprise a temperature-sensitive self-replicating RNA. As used herein, the term "temperature-sensitive self-replicating RNA" refers to any self-replicating RNA that has different levels of functionality at different temperatures.

In some embodiments, temperature-sensitive self-replicating RNAs are created by engineering self-replicating RNAs, which are single-stranded RNAs that are usually made from the Alphavirus such as Venezuelan Equine Encephalitis Virus (VEEV), Sindbis Virus (SINV), and Semliki Forest Virus (SFV), by removing DNAs encoding structural proteins that are required for virus particle formation (Petrakova et al., 2005). In some embodiments, self-replicating RNAs encode nonstructural proteins (nsPs), which function as an RNA-dependent RNA polymerase to replicate the self-replicating RNA itself and to produce a transcript for translation. In some embodiments, self-replicating RNAs can also comprise a gene of interest (GOI) encoding a protein of interest, and other genetic elements. Without wishing to be bound by theory, in some embodiments, due to its positive feedback production of RNAs, self-replicating RNAs can express the GOI at a high level. In some embodiments, a temperature-sensitive self-replicating RNA may be created by mutating genes encoding nsPs.

In some embodiments, temperature-sensitive self-replicating RNAs can be delivered to mammalian cells as a naked RNA (i.e., a synthetic RNA). In some embodiments, temperature-sensitive self-replicating RNAs can be delivered to mammalian cells as a naked RNA (i.e., a synthetic RNA) encapsulated by nanoparticles. In some embodiments, nanoparticles are engineered to target specific cell types, tissues, organs, cancers, tumors, or abnormal cells. In some embodiments, temperature-sensitive self-replicating RNAs can be delivered to mammalian cells as a virus particle, which can be generated by supplementing the missing virus structural proteins by packaging helper cells. In some embodiments, virus particles are engineered to target specific cell types, tissues, organs, cancers, tumors, or abnormal cells.

When the temperature-sensitive agent is a temperature-sensitive self-replicating RNA, an activity of the temperature-sensitive self-replicating RNA induced at a permissive temperature may include replication of the RNA.

In some aspects, the permissive temperature for temperature-sensitive self-replicating RNAs of the present disclosure typically ranges from 30° C. to 36° C. In some embodiments, the permissive temperature is from about 31° C. to about 35° C., or 32° C. to 34° C. (33° C.±1.0° C.). In some preferred embodiments, the permissive temperature is 33° C.±0.5° C. It follows that in some embodiments, the non-permissive temperature for the temperature-sensitive self-replicating RNAs of the present disclosure is above 36° C. In some preferred embodiments, the non-permissive temperature is 37° C.±0.5° C.

In other aspects, the permissive temperature for temperature-sensitive self-replicating RNAs of the present disclosure typically ranges from 38° C. to 50° C. It follows that in some embodiments, the non-permissive temperature for the temperature-sensitive self-replicating RNAs of the present disclosure is above 36° C. and below 38° C. In some preferred embodiments, the non-permissive temperature is 37° C.±0.5° C.

Temperature-Sensitive Polypeptides

In certain embodiments, a temperature-sensitive therapeutic agent of the present disclosure may comprise a temperature-sensitive polypeptide. As used herein, the term "temperature-sensitive polypeptide" refers to any temperature-sensitive polypeptide that has different levels of functionality at different temperatures. In some embodiments, the temperature-sensitive polypeptide may be a temperature-sensitive antibody. In other embodiments, the temperature-sensitive polypeptide is selected from but not limited to a transcription factor, a growth factors, a cell surface marker, a cell fusion protein, an epigenetic modifier, an enzyme, and a structural protein.

When the temperature-sensitive agent is a temperature-sensitive polypeptide, an activity of the temperature-sensitive protein induced at a permissive temperature may include a conformational change (e.g., change to the structure or shape) of the protein.

The permissive temperature for the temperature-sensitive polypeptides of the present disclosure typically ranges from 30° C. to 36° C. or from 38° C. to 50° C. In some embodiments, the permissive temperature is from about 31° C. to about 35° C., or from 32° C. to 34° C. (33° C.±1.0° C.). In some preferred embodiments, the permissive temperature is 33° C.±0.5° C. It follows that in some embodiments, the non-permissive temperature for the temperature-sensitive self-replicating polypeptides of the present disclosure is above 36° C. and below 38° C. In some preferred embodiments, the non-permissive temperature is 37° C.±0.5° C.

Various aspects of the present disclosure relate to substantially purified polypeptides. A substantially purified polypeptide may refer to a polypeptide which is substantially free of other polypeptides, lipids, carbohydrates or other materials with which it is naturally associated. In one embodiment, the polypeptide is at least 50%, for example at least 80% free of other polypeptides, lipids, carbohydrates or other materials with which it is naturally associated. In another embodiment, the polypeptide is at least 90% free of other polypeptides, lipids, carbohydrates or other materials with which it is naturally associated. In yet another embodiment, the polypeptide is at least 95% free of other polypeptides, lipids, carbohydrates or other materials with which it is naturally associated.

Nucleic Acids and Polypeptides

Certain aspects of the present disclosure relate to transiently inducing an activity of a temperature-sensitive therapeutic agent in one or more cells, wherein the activity leads to increased expression of a nucleic acid molecule. In some embodiments, the nucleic acid is a polynucleotide. A polynucleotide may refer to a nucleic acid sequence (such as a linear sequence) of any length. Therefore, a polynucleotide includes oligonucleotides, and also gene sequences found in chromosomes. An oligonucleotide is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

In certain embodiments, the nucleic acid molecules or polynucleotides encode a genetic element. These polynucleotides include DNA, cDNA and RNA sequences, such as mRNA sequences, which encode a gene of interest. A coding sequence may be operably linked to a heterologous promoter to direct transcription of the genetic element. A promoter may refer to nucleic acid control sequences which direct transcription of a nucleic acid. A promoter includes necessary nucleic acid sequences near the start site of transcription. A promoter also optionally includes distal enhancer or repressor elements. A constitutive promoter is a promoter that is continuously active and is not subject to regulation by external signals or molecules. In contrast, the activity of an inducible promoter is regulated by an external signal or molecule (for example, a transcription factor). A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and where necessary to join two protein coding regions, in the same reading frame. A heterologous polypeptide or polynucleotide refers to a polypeptide or polynucleotide derived from a different source or species. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In one example, the promoter is a constitutive promoter, such as the CAG-promoter (Niwa et al., Gene 108 (2):193-9, 1991), or the phosphoglycerate kinase (PGK)-promoter. In some embodiments, the promoter is an inducible promoter such as a tetracycline-inducible promoter (Masui et al., Nucleic Acids Res. 33:e43, 2005). Other exemplary promoters that can be used to drive expression of a genetic element include but are not limited to: lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, and the promoter of the yeast alpha-mating factors. Genetic elements of the present disclosure may be under the control of a constitutive promoter, an inducible promoter, or any other suitable promoter described herein or other suitable promoter that will be readily recognized by one skilled in the art.

In some embodiments, inducing an activity of a temperature-sensitive agent leads to increased expression of a nucleic acid or a polypeptide, which may include increased expression by at least 1.5 fold, at least 1.6 fold, at least 1.7 fold, at least 1.8 fold, at least 1.9 fold, at least 2.0 fold, at least 2.1 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, at least 10 fold, at least 50 fold, at least 100 fold, at least 200 fold, at least 300 fold, at least 400 fold, at least 500 fold, at least 600 fold, at least 700 fold, at least 800 fold, at least 900 fold, at least 1,000 fold, at least 2,000 fold, at least 3,000 fold, at least 4,000 fold, at least 5,000 fold, at least 6,000 fold, at least 7,000 fold, at least 8,000 fold, at least 9,000 fold, at least 10,000 fold, at least 25,000 fold, at least 50,000 fold, at least 75,000 fold, at least 100,000 fold, at least 125,000 fold, at least 150,000 fold, at least 175,000 fold, at least 200,000 fold, at least 225,000 fold, at least 250,000 fold, at least 275,000 fold, at least 300,000 fold, at least 325,000 fold, at least 350,000 fold, at least 375,000 fold, at least 400,000 fold, at least 425,000 fold, at least 450,000 fold, at least 475,000 fold, at least 500,000 fold, at least 750,000 fold, or at least 1,000,000 fold, for example, relative to the polynucleotide or polypeptide expression in a human cell that has not been contacted with the agent.

Various aspects of the present disclosure relate to isolated entities, such as isolated nucleic acids or synthetic mRNA molecules. An isolated nucleic acid has been substantially separated or purified away from other nucleic acid sequences and from the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. Similarly, isolated polypeptides have been substantially separated or purified from other polypeptides of the cells of an organism in which the protein naturally occurs, and encompasses polypeptides prepared by recombination expression in a host cell as well as chemically synthesized polypeptides. Similarly, isolated cells have been substantially separated away from other cell types.

Methods of Introducing Temperature-Sensitive Agents into Cells

In some embodiments the one or more cells are contacted with a temperature-sensitive agent. Contacting may refer to placement in direct physical association, including both in solid and liquid form. "Contacting" may be used interchangeably with "exposed." In some cases, "contacting" includes transfecting, such as transfecting a nucleic acid molecule into a cell. In some cases "contacting" includes introducing the temperature-sensitive agent into one or more cells.

In some embodiments, temperature-sensitive agents are polynucleotides (e.g. self-replicating RNAs), and polynucleotides are introduced into cells. Introducing a nucleic acid molecule or a protein into a cell encompasses any means of delivering the nucleic acid molecule or protein into the cell. For example, nucleic acid molecules can be transfected, transduced or electroporated into a cell. In some embodiments temperature-sensitive agents are polypeptides (e.g. temperature-sensitive polypeptides), and polypeptides are introduced into cells. Delivery of polypeptides into cells can be achieved, for example, by fusing the protein to a cell-penetrating peptide, such as a peptide with a protein transduction domain (e.g., HIV-1 Tat), or a poly-arginine peptide tag (Fuchs and Raines, *Protein Science* 14:1538-1544, 2005). Protein transduction domains may refer to small cationic peptides that facilitate entry of larger molecules (proteins, nucleic acid molecules etc.) into a cell by a mechanism that is independent of classical endocytosis. A poly-arginine peptide tag may refer to a short peptide (generally 7 to 11 residues) comprised of arginine residues that facilitates delivery of larger molecules (such as proteins and nucleic acid molecules) into cells (see, for example, Fuchs and Raines, *Protein Science* 14:1538-1544, 2005).

Introduction of nucleic acids into cells with a temperature-sensitive agent may involve using a temperature-sensitive viral vector (such as integrating or non-integrating viral vectors) or a temperature-sensitive plasmid vector. Each of these methods has been described in the art and is therefore within the capabilities of one of skill in the art. A brief summary of each method that can be used to nucleic acid to a human cell is provided herein. A vector may refer to a nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). For example, an expression vector contains the necessary regulatory sequences to allow transcription and translation of inserted gene or genes. A vector may also include one or more selectable marker genes and other genetic elements known in the art. Vectors may include, for example, virus vectors and plasmid vectors.

Permissive Temperatures

Incubating One or More Cells at a Permissive Temperature

Certain aspects of the present disclosure relate to transiently inducing an activity of a temperature-sensitive agent in one or more cells by incubating the cells at a permissive temperature for inducing an activity of the temperature-sensitive agent. In some embodiments, the permissive temperature may be higher or lower than the standard cell culture temperature. For example, human and rodent cells are typically cultured at a temperature of about 37° C. Accordingly, in some embodiments the permissive temperature may be lower than about 36.5° C. For example, in some embodiments the cells are cultured at a permissive temperature of 36° C., 35.5° C., 35° C., 34.5° C., 34° C., 33.5° C., 33° C., 32.5° C., 32° C., 31.5° C., 31° C., 30.5° C., or 30° C. In some preferred embodiments, the permissive temperature is from 30° C. to 36° C., or from 31° C. to 35° C., or from 32° C. to 34° C., or from 32.5° C. to 33.5° C. In some embodiments, the permissive temperature is greater than or equal to (lower limit) 30° C., 31° C., 32° C., 33° C., 34° C., or 35° C., and is less than or equal to (upper limit) 36° C., 35° C., 34° C., 33° C., 32° C. or 31° C.

In other embodiments, the permissive temperature maybe higher than about 37.5° C. For example, in some embodiments the cells are cultured at a permissive temperature of 38° C., 38.5° C., 39° C., 39.5° C., 40° C., 40.5° C., 41° C., 41.5° C., 42° C., 42.5° C., 43° C., 43.5° C., 44° C., 44.5° C., 45° C., 45.5° C., 46° C., 46.5° C., 47° C., 47.5° C., 48° C., 48.5° C., 49° C., 49.5° C., or 50° C.

In some embodiments, after incubating at a permissive temperature, the one or more cells are cultured at a non-permissive temperature wherein the activity of the temperature-sensitive agent is reduced or inhibited. For example, replication of temperature-sensitive viral vectors can be inhibited, replication of temperature-sensitive self-replicating RNAs can be inhibited, and conformational changes to temperature-sensitive polypeptides can be inhibited. This temperature shifting allows the activity of the temperature-sensitive agent to be transiently induced and then inhibited. In other embodiments, the one or more cells are administered to a subject after being cultured at a permissive temperature. The one or more cells may be administered to a subject directly from culture at a permissive temperature, or may first be transferred from a permissive temperature to a non-permissive temperature in culture and then administered to a subject. In certain embodiments, the temperature-sensitive agent is subsequently degraded. For example, non-integrating temperature-sensitive viral vectors, RNAs, and polypeptides will be degraded.

Lowering the Core Body Temperature of a Subject to a Permissive Temperature

Certain aspects of the present disclosure relate to transiently inducing an activity of a temperature-sensitive therapeutic agent in cells in a subject by lowering the subject's core body temperature to a permissive temperature for inducing the activity of the temperature-sensitive agent. In some embodiments the subject's core body temperature is lowered using a target-temperature management (TTM) procedure. A TTM procedure is designed to achieve and maintain a specific body temperature in a subject for a duration of time. Such procedures have previously been used therapeutically to reduce the negative effects resulting from various acute health issues such as heart attacks and strokes. Equipment and general methods of using them are known in the art and can be used in the methods described herein. The procedure can be carried out using a number of methods, including cooling catheters, cooling blankets, and application of ice around the body.

After lowering the subject's core body temperature to a permissive temperature, the subject's core body temperature is maintained at the permissive temperature for a time sufficient to induce an activity of the temperature-sensitive agent. The subject's core body temperature is subsequently returned to normal core body temperature, which is a non-permissive temperature wherein the activity of the temperature-sensitive agent is reduced or inhibited. In certain embodiments the temperature-sensitive agent is subsequently degraded. For example, non-integrating temperature-sensitive viral vectors, RNAs, and polypeptides will be degraded at the non-permissive temperature. As used herein, the term "body temperature" refers to "core body temperature", unless context clearly indicates otherwise.

Maintaining the Surface Body Temperature of a Subject at a Permissive Temperature Certain aspects of the present disclosure relate to exploiting the natural temperature differences in regions of a subject's body. For example, the temperature at or near the surface of a human subject's body (surface body temperature) is around 31-34° C., which is lower than the core body temperature of the human subject, which is around 37° C. As used herein, the "surface" of a subject's body refers to one or more of the epidermis, dermis, hypodermis, or muscle. The "skin" of a subject's body refers to one or both of the epidermis and dermis. Thus, suitable routes of administration to the epidermis, dermis, or hypodermis of a subject's body include intradermal and subcutaneous administration. A suitable route of administration to muscle near the surface of a subject's body is intramuscular administration.

For instance, the ts-agent is directly delivered to a specific area of the skin of a subject (in the case of vaccination) or to a broader area of the skin of a subject (in the case of treatment of a skin disease). The skin temperature (about 31-34° C.) is a permissive temperature for the ts-agent, permitting the ts-agent to function. No further action is required for the long-term expression of GOI. If termination of the function of the ts-agent is need or desired, the temperature of the treated skin is increased and transiently maintained at non-permissive temperature (>37° C.) by local application of heat (e.g., heat patch or heating blanket) or by mild therapeutic hyperthermia (e.g., warm bath or hot sauna). This therapeutic procedure is safe in that the ts-agent functions only in the intended area of the body, because the core body temperature is a non-permissive temperature (about 37° C.). In some embodiments, should the surface body temperature of the subject be higher than normal, the surface body temperature is lowered to match the permissive temperature of the ts-agent.

Maintaining the Upper Respiratory Tract Temperature of a Subject at a Permissive Temperature Like the surface body temperature of a human subject, the temperature of the upper respiratory tract and upper trachea of a human subject is a permissive temperature for the ts-agent, permitting the ts-agent to function. That is, the temperature of the nasal cavity and upper trachea of a human subject is about 32° C., and the temperature of the subsegmental bronchi of a human subject is about 35° C. (McFadden et al., 1985). As such, ts-agents administered intranasally to cells of the upper respiratory tract (nasal cavity, pharnyx, and/or larnyx) and/or upper trachea of a human patient are functional without lowering the core body temperature of the human patient. Intranasal administration may be done by insufflation, inhalation or instillation.

Non-Permissive Temperatures
Incubating One or More Cells at a Non-Permissive Temperature In vitro culture of cells is usually carried out at the normal body temperature of the subject from which the cells are derived. For example, mammalian cells, such as human cells and mouse cells, are usually cultured at about 37° C. Certain aspects of the present disclosure relate to a temperature-sensitive agent that does not function (e.g., does not replicate or express genes) at the normal body temperature of the subject. Thus, the normal body temperature of the subject is a non-permissive temperature for the temperature-sensitive agent. In some preferred embodiments, the non-permissive temperature is 37° C.±0.5° C.

Normal Core Body Temperature of a Subject

In some embodiments, a temperature-sensitive agent, cells contacted with a temperature-sensitive agent, or cells carrying a temperature-sensitive agent, are introduced into a subject body that is maintained at the normal body temperature. Certain aspects of the present disclosure relate to a temperature-sensitive agent that does not function, e.g., replicate or express genes, at this normal body temperature (non-permissive temperature) of the organism. This feature provides a safety mechanism that prevent the undesirable action or reactivation of the temperature-sensitive agent during the life-course of the subject.

Human Cells

Certain aspects of the present disclosure relate to transiently inducing an activity of a temperature-sensitive therapeutic agent in one or more human cells, including without limitation, human adult cells. In certain embodiments, the one or more human cells are in a subject in need of treatment with the therapeutic agent.

Various human cells find use in the methods described herein. As disclosed herein, the term "human cell(s)" refers to any cell(s) found throughout the human body during and after embryonic development, such as human embryonic cells, stem cells, pluripotent cells, differentiated cells, mature cells, somatic cells, and adult cells. In some embodiments, human cells of the present disclosure are human adult cells. As disclosed herein, the term "human adult cell(s)" refers to any cell(s) found throughout the human body after embryonic development (i.e., non-embryonic cells). Human cells of the present disclosure include, without limitation, sperm cells, oocyte cells, fertilized oocytes (i.e., zygotes), embryonic cells, mature cells, differentiated cells, somatic cells, progenitor cells, embryonic stem (ES) cells, induced pluripotent stem (iPS) cells, adult stem cells, somatic stem cells, and tissue stem cells. Adult stem cells, which are also known as somatic stem cells or tissue stem cells, may refer to undifferentiated cells, found throughout the body after embryonic development, which multiply by cell division to replenish dying cells and regenerate damaged tissues. Progenitor cells may refer to oligopotent or unipotent cells that differentiate into a specific type of cell or cell lineage. Progenitor cells are similar to stem cells but are more differentiated and exhibit limited self-renewal. Exemplary adult stem cells, tissue stem cells, and/or progenitor cells may include, without limitation, hematopoietic stem cells, mesenchymal stem cells, adipose stem cells, neuronal stem cells, intestinal stem cells, skin stem cells, and germ cells (such as, sperm cells and oocytes).

Human cells may also include, without limitation, somatic cells, mature cells, and differentiated cells. Somatic cells may refer to any cell of the body, including, without limitation, germ cells, tissue stem cells, progenitor cells, induced pluripotent stem (iPS) cells, and differentiated cells. Exemplary somatic cells, mature cells, and/or differentiated cells may include, without limitation, epidermal cells, fibroblasts, lymphocytes, hepatocytes, epithelial cells, myocytes, chondrocytes, osteocytes, adipocytes, cardiomyocytes, pancreatic p cells, keratinocytes, erythrocytes, peripheral blood cells, bone marrow cells, neurocytes, astrocytes, and germ cells. Germ cells may refer to the cells that give rise to the gametes (i.e., eggs and sperm) of organisms that reproduce sexually. In certain embodiments, germ cells include, without limitation, oocytes, and sperm cells. In some embodiment, somatic cells, mature cells, and/or differentiated cells of the present disclosure also include, without limitation, preimplantation embryos.

Human cells may also include, without limitation, cells derived from cord blood, hematopoietic stem cells, CD34+ cells, mesenchymal stem cells, vascular endothelial stem cells, tissue stem cells, granulocytes, lymphocytes, T-cells, B-cells, monocytes, macrophages, dendritic cells, red blood cells, reticulocytes, and megakaryocytes. Human cells may also include, without limitation, abnormal cells of human origins, such as cancer cells, tumor cells, malignant cells, benign cells, hyperplastic cells, hypoplastic cells, and atypical cells. Human cells may also include, without limitation, diploid cells, haploid cells, tetraploid cells, polyploid cells, cells with karyotype abnormalities, cells with chromosome abnormalities, cells with mutated genes, cells with abnormal telomere lengths, cells with short telomeres, and cells with long telomeres. Human cells may also include, without limitation, cells with epigenetic abnormalities, such as cells with hypomethylated genomic regions, cells with hypermethylated genomics regions, cells with the abnormal histone modifications such as acetylation and methylation.

In some embodiments, the subjects of the present disclosure are non-human animals. Non-human animals may refer to all animals other than humans. A non-human animal includes, but is not limited to, a non-human primate, a farm animal such as swine, cattle, and poultry, a sport animal or pet such as dogs, cats, horses, hamsters, rodents, such as mice, or a zoo animal such as lions, tigers or bears. In one embodiment, the non-human animal is a mouse.

Therapeutic Uses of Temperature-Sensitive Agents

Temperature-sensitive agents of the present disclosure may be administered by any suitable method known in the art, including, without limitation, by oral administration, sublingual administration, buccal administration, topical administration, rectal administration, via inhalation, transdermal administration, subcutaneous injection, intravenous (IV) injection, intra-arterial injection, intramuscular injection, intracardiac injection, intraosseous injection, intradermal injection, intraperitoneal injection, transmucosal administration, vaginal administration, intravitreal administration, intra-articular administration, peri-articular administration, local administration, epicutaneous administration, or any combinations thereof. In some embodiments, the composition is administered by subcutaneous injection and/or intravenous injection. In some embodiments, the composition is administered by injection into the spleen of the subject.

In some aspects, the methods of the present disclosure involve the use of a therapeutically effective amount of a temperature-sensitive agent. A therapeutically effective amount of an agent may refer to the amount of a therapeutic agent sufficient to achieve the intended purpose. For example, a therapeutically effective amount of a temperature-sensitive agent in a human cell to treat a disease or condition is an amount sufficient to reduce the disease or condition, or one or more symptoms of the disease or condition. A therapeutically effective amount may in some examples not treat the disease or condition, or symptoms of the disease or condition 100%. However, a decrease in any known feature or symptom of the disease or condition, such as a decrease of at least 25%, at least 50%, at least 60%, at least 70%, at least 80%, at least 90%, at least 95% can be therapeutic.

The therapeutically effective amount of a given therapeutic agent will vary with factors such as the nature of the agent, the route of administration, the size and/or age of the subject to receive the therapeutic agent, and the purpose of the administration. The therapeutically effective amount in each individual case can be determined empirically without undue experimentation by a skilled artisan according to established methods in the art.

A subject may refer to living multi-cellular vertebrate organisms, a category that includes human and non-human mammals. In some embodiments, the subject is a human. Subjects that can be treated using the methods provided herein may include mammalian subjects, such as a veterinary or human subject. Subjects may include fertilized eggs, zygotes, preimplantation embryos, embryos, fetus, newborns, infants, children, and/or adults. In some embodiments, the subject to be treated is selected, such as selecting a subject that would benefit from a therapy, particularly therapy that includes administration of a temperature-sensitive agent of the present disclosure.

Pharmaceutical compositions of the present disclosure comprise a ts-agent, such as a therapeutic ts-agent, and one or more additional compounds. As used herein, the terms "pharmaceutically acceptable carrier" and "pharmaceutically acceptable vehicle" refer to the one or more additional compound(s) (i.e., compounds other than the ts-agent). Pharmaceutically acceptable carriers suitable for use in the present disclosure are conventional. In particular, compositions and formulations suitable for pharmaceutical delivery of compositions comprising a temperature-sensitive agent are as previously described (see, e.g., Gennaro, A. R. (editor) *Remington's Pharmaceutical Sciences*, Mack Publishing Co., Easton, Pa., 18th edition (1990); and Felton, L. A. (editor) *Remington Essentials of Pharmaceutics*, Pharmaceutical Press, London, United Kingdom, 1' edition, (2013)).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In some embodiments, pharmaceutical compositions of the present disclosure comprise a ts-agent, such as a therapeutic ts-agent, and one or more additional compounds, which facilitate the incorporation of ts-agent into cells. In the case of RNA-based ts-agent, ts-agent is encapsulated in nanoparticles. In some instances, nanoparticles is lipid-based (e.g., lipofectamine).

The therapeutic dose and regimen most appropriate for patient treatment will vary with diseases or conditions to be treated, and according to the patient's weight and other parameters. An effective dosage and treatment protocol can be determined by conventional means, starting with a low dose in laboratory animals and then increasing the dosage while monitoring the effects, and systematically varying the dosage regimen. Numerous factors can be taken into consideration by a clinician when determining an optimal dosage for a given subject. Factors include the size of the patient, the age of the patient, the general condition of the patient, the particular disease being treated, the severity of the disease, the presence of other drugs in the patient, and the like. The trial dosages would be chosen after consideration of the results of animal studies and the clinical literature.

Mobilizing Bone Marrow Cells

In some embodiments, the methods include mobilizing bone marrow cells (including, without limitation, CD34+ cells, hematopoietic stem cells, mesenchymal stem cells, endothelial stem cells) to the spleen and peripheral blood of the subject. In some embodiments, the methods include administering a therapeutically effective amount of a temperature-sensitive agent (e.g., a temperature-sensitive therapeutic agent) of the present disclosure under conditions suitable for the temperature-sensitive agent to deliver a nucleic acid to one or more bone marrow cells (including, without limitation, CD34+ cells, hematopoietic stem cells, mesenchymal stem cells, endothelial stem cells) in the spleen.

In some embodiments of the methods disclosed herein, mobilizing bone marrow cells (including, without limitation, CD34+ cells, hematopoietic stem cells, mesenchymal stem cells, endothelial stem cells) to the spleen and peripheral blood comprises administering to the subject a therapeutically effective amount of a cytokine and/or a chemotherapeutic. In some embodiments, mobilizing bone marrow cells (including, without limitation, CD34+ cells, hematopoietic stem cells, mesenchymal stem cells, endothelial stem cells) to the spleen and peripheral blood comprises administering to the subject a therapeutically effective amount of a cytokine. In some embodiments, mobilizing bone marrow cells (including, without limitation, CD34+ cells, hematopoietic stem cells, mesenchymal stem cells, endothelial stem cells) to the spleen and peripheral blood comprises administering to the subject a therapeutically effective amount of a chemotherapeutic. In some embodiments, mobilizing bone marrow cells (including, without limitation, CD34+ cells, hematopoietic stem cells, mesenchymal stem cells, endothelial stem cells) to the spleen and peripheral blood comprises administering to the subject a therapeutically effective amount of a cytokine and a chemotherapeutic. Cytokines and/or chemotherapeutics may be administered by any suitable method known in the art, including, without limitation, by oral administration, sublingual administration, buccal administration, topical administration, rectal administration, via inhalation, transdermal administration, subcutaneous injection, intravenous (IV) injection, intra-arterial injection, intramuscular injection, intracardiac injection, intraosseous injection, intradermal injection, intraperitoneal injection, transmucosal administration, vaginal administration, intravitreal administration, intra-articular administration, peri-articular administration, local administration, epicutaneous administration, or any combinations thereof. In some embodiments, the cytokine and/or chemokine is administered by subcutaneous injection and/or intravenous injection.

In some embodiments, the bone marrow cells (including, without limitation, CD34+ cells, hematopoietic stem cells, mesenchymal stem cells, endothelial stem cells) of the subject are mobilized at least 4 weeks before, at least 3 weeks before, at least 2 weeks before, at least 1 week before, at least 6 days before, at least 5 days before, at least 4 days before, at least 3 days before, at least 2 days before, at least 1 day before, less than 1 day before, at least 18 hours before, at least 16 hours before, at least 12 hours before, at least 8 hours before, at least 6 hour before, or at least 1 hour before administration of the composition (e.g., any nanoparticle composition as described herein). In some embodiments, the bone marrow cells (including, without limitation, CD34+ cells, hematopoietic stem cells, mesenchymal stem cells, endothelial stem cells) of the subject are mobilized for seven consecutive days, five consecutive days, four consecutive days, three consecutive days, two consecutive days, or for one day before administration of the composition. In some embodiments, the bone marrow cells (including, without limitation, CD34+ cells, hematopoietic stem cells, mesenchymal stem cells, endothelial stem cells) of the subject are mobilized concurrently with administration of the composition.

Any cytokine capable of mobilizing bone marrow cells (including, without limitation, CD34+ cells, hematopoietic stem cells, mesenchymal stem cells, endothelial stem cells) known in the art may be used, including, without limitation, granulocyte-colony stimulating factor (G-CSF), granulocyte-macrophage colony stimulating factor (GM-CSF), erythropoietin (EPO), thrombopoietin (TPO), stem cell factor (SCF), parathyroid hormone (PTH), and any combinations thereof. In some embodiments, the cytokine is G-CSF.

In some embodiments, the G-CSF is administered to the subject at a concentration of about 0.1 µg/kg to about 100 µg/kg, or about 1.0 µg/kg to about 10 µg/kg. In some embodiments, the G-CSF is administered to the subject at a concentration of about 2.5 µg/kg. In some embodiments, the G-CSF is administered to the subject at a concentration of about 10 µg/kg.

Any chemotherapeutic capable of mobilizing bone marrow cells (including, without limitation, CD34+ cells, hematopoietic stem cells, mesenchymal stem cells, endothelial stem cells) known in the art may be used, including, without limitation, plerixafor, cyclophosphamide (CY), paclitaxel, etoposide, POL6326, BKT-140, TG-0054, NOX-A12, SEW2871, BIO 5192, bortezomib, SB-251353, FG-4497, and any combinations thereof. In some embodiments, the chemotherapeutic is plerixafor.

In some embodiments, the plerixafor is administered to the subject at a concentration of about 1 µg/kg to about 1000 µg/kg, or about 75 µg/kg to about 500 µg/kg. In some embodiments, the plerixafor is administered to the subject at a concentration of about 150 µg/kg. In some embodiments, the plerixafor is administered to the subject at a concentration of about 240 µg/kg.

In some embodiments, mobilizing bone marrow cells (including, without limitation, CD34+ cells, hematopoietic stem cells, mesenchymal stem cells, endothelial stem cells) to the spleen and peripheral blood comprises administering a therapeutically effective amount of G-CSF and a therapeutically effective amount of plerixafor. In some embodiments, the G-CSF and plerixafor are co-administered to the subject. In some embodiments, the G-CSF and plerixafor are co-administered to the subject for one day, two days, three days, four days, or more. In some embodiments, the G-CSF is administered to the subject prior to the plerixafor. In some embodiments, the G-CSF is administered to the subject one day, two days, three days, four days or more prior to the plerixafor. In some embodiments, the G-CSF is administered to the subject one day, two days, three days, four days or more prior to the plerixafor, and G-CSF and plerixafor are then co-administered to the subject for one day, two days, three days, four days or more. In some embodiments, the plerixafor is administered to the subject prior to the G-CSF. In some embodiments, the plerixafor is administered to the subject one day, two days, three days, four days or more prior to the G-CSF. In some embodiments, the plerixafor is administered to the subject one day, two days, three days, four days or more prior to the G-CSF, and G-CSF and plerixafor are then co-administered to the subject for one day, two days, three days, four days or more.

In some embodiments, one or more human cells are contacted with a temperature-sensitive agent (e.g., a temperature-sensitive therapeutic agent) that delivers a nucleic acid to the one or more human cells. In some embodiments, the nucleic acid comprises a gene of interest or encodes a protein of interest.

In some aspects, the methods of the present disclosure involve the use of a therapeutically amount of a temperature-sensitive agent (e.g., a temperature-sensitive therapeutic agent) that delivers a nucleic acid to cells of a subject in vitro or in vivo. A therapeutically effective amount of an agent may refer to the amount of a therapeutic agent sufficient to achieve the intended purpose. For example, a therapeutically effective amount of a temperature-sensitive agent (e.g., a temperature-sensitive therapeutic agent) that delivers a nucleic acid to a human cell to treat a disease or condition is an amount sufficient to reduce the disease or condition, or one or more symptoms of the disease or condition. A therapeutically effective amount may in some examples not treat the disease or condition, or symptoms of the disease or condition 100%. However, a decrease in any known feature or symptom of the disease or condition, such as a decrease of at least 25%, at least 50%, at least 60%, at least 70%, at least 80%, at least 90%, or at least 95% can be therapeutic.

In another example, a therapeutically effective amount of a cytokine and/or chemokine capable of mobilizing bone marrow cells (including, without limitation, CD34+ cells, hematopoietic stem cells, mesenchymal stem cells, endothelial stem cells) in a subject is an amount sufficient to induce mobilization of one or more bone marrow cells (including, without limitation, CD34+ cells, hematopoietic stem cells, mesenchymal stem cells, endothelial stem cells) from the bone marrow into the peripheral blood.

The therapeutically effective amount of a given temperature-sensitive agent (e.g., a temperature-sensitive therapeutic agent) will vary with factors such as the nature of the agent, the route of administration, the size and/or age of the subject to receive the therapeutic agent, and the purpose of the administration. The therapeutically effective amount in each individual case can be determined empirically without undue experimentation by a skilled artisan according to established methods in the art.

A subject may refer to living multi-cellular vertebrate organisms, a category that includes human and non-human mammals. In some embodiments, the subject is a human. Subjects that can be treated using the methods provided herein may include mammalian subjects, such as a veterinary or human subject. Subjects may include a fetus, newborns, infants, children, and/or adults. In some embodiments, the subject to be treated is selected, such as selecting a subject that would benefit from a therapy.

Treating Diseases and Disorders

Examples of disorders or diseases that can benefit from administration of a temperature-sensitive agent (e.g., a temperature-sensitive therapeutic agent) include those disorders or diseases that are associated with gene mutation(s), abnormal telomere length, or abnormal epigenetic modification(s). Further examples of disorders or diseases that can benefit from administration of a temperature-sensitive agent (e.g., a temperature-sensitive therapeutic agent) include cancer, autoimmune diseases, and diseases in which cell regeneration is beneficial, such as neurologic injuries or a neurodegenerative disorders, as well as blindness and deafness.

Cancers include malignant tumors that are characterized by abnormal or uncontrolled cell growth. Cancers are frequently associated with gene mutations and aberrant telomere regulation. Exemplary cancers that can benefit from treatment with a ts-agent include but are not limited to cancers of the heart (e.g., sarcoma (angiosarcoma, fibrosarcoma, rhabdomyosarcoma, liposarcoma), myxoma, rhabdomyoma, fibroma, lipoma and teratoma), lung (e.g., bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma); gastrointestinal tract (e.g., esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), genitourinary tract (e.g., kidney (adenocarcinoma, Wilms' tumor, nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma), liver (e.g., hepatoma (hepatocellular carcinoma), cholangiocarcinoma, hepatoblastoma, angiosarcoma, hepatocellular adenoma, hemangioma), bone (e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxofibroma, osteoid osteoma and giant cell tumors), nervous system (e.g., skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma, pinealoma, glioblastoma multiforme, oligodendroglioma, schwannoma, retinoblastoma, congenital tumors), spinal cord (neurofibroma, meningioma, glioma, sarcoma), gynecological cancers (e.g., uterus (endometrial carcinoma), cervix (cervical carcinoma, pre-tumor cervical dysplasia), ovaries (ovarian carcinoma, serous cystadenocarcinoma, mucinous cystadenocarcinoma, endometrioid tumors, Brenner tumor, clear cell carcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma, embryonal rhabdomyosarcoma, fallopian tubes (carcinoma)), hematologic cancers (e.g., blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma)), skin (e.g., malignant melanoma, basal cell carcinoma, squamous cell carcinoma, Kaposi's sarcoma, moles, dysplastic nevi, lipoma, angioma, dermatofibroma, keloids, psoriasis), and adrenal glands (e.g., neuroblastoma).

An autoimmune diseases result from an aberrant immune response, such as the production of antibodies or cytotoxic T cells specific for a self-antigen or a subject's own cells or tissues. In some instances, the autoimmune disease is restricted to certain organs (e.g., in thyroiditis) or can involve a particular tissue in different places (e.g., Goodpasture's disease). Exemplary autoimmune diseases that can benefit from treatment with a ts-agent include but are not limited to rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, and pernicious anemia.

In some embodiments, the subject is one who has suffered a neurologic injury or suffers from a neurodegenerative disorder. A neurological injury may refer to a trauma to the nervous system (such as to the brain or spinal cord or particular neurons), which adversely affects the movement and/or memory of the injured patient. For example, such patients may suffer from dysarthria (a motor speech disorder), hemiparesis or hemiplegia. Neurologic injuries can result from a trauma to the nervous system (such as to the brain or spinal cord or particular neurons), which adversely affects the movement and/or memory of the injured patient. Such traumas may be caused by an infectious agent (e.g., a bacterium or virus), a toxin, an injury due to a fall or other type of accident, or genetic disorder, or for other unknown reasons. Accordingly, in some embodiments, a temperature-sensitive agent (e.g., a temperature-sensitive therapeutic agent) of the present disclosure that temperature-sensitive may be used to treat a neurologic injury in a subject, by modulating tissue stem cells in the nervous system of a patient that has suffered a neurologic injury, where modulating tissue stem cells in the nervous system produces neurons and glial cells, thereby repairing defects in nervous system. In some embodiments, a temperature-sensitive agent encoding various neurotrophic factors such as brain-derived neurotrophic factor (BDNF), nerve growth factor (NGF), neurotrophin-3, neurotrophin-4, ciliary neurotrophic factor, glial cell line-derived neurotrophic factor (GDNF) may be used to treat such patients. In some embodiments, the patient may have suffered a neurologic injury, such as a brain or spinal cord injury resulting from an accident, or from a stroke.

A neurodegenerative disease is a condition in which cells of the brain and/or spinal cord are lost. Neurodegenerative diseases result from deterioration of neurons or their myelin sheath which over time leads to dysfunction and disabilities. Conditions that result can cause problems with movement (such as ataxia) and with memory (such as dementia). Accordingly, in some embodiments, a temperature-sensitive agent (e.g., a temperature-sensitive therapeutic agent) of the present disclosure may be used to treat a neurodegenerative disease in a subject, by modulating tissue stem cells in the nervous system of a patient suffering from a neurodegenerative disease, where modulating tissue stem cells in the nervous system produces neurons and glial cells, thereby repairing defects in nervous system. In some embodiments, the agent modulates the nervous system of the subject and revert the degenerative conditions of the disease. Exemplary neurodegenerative diseases include but are not limited to: adrenoleukodystrophy (ALD), alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, cerebral palsy, Cockayne syndrome, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), Multiple System Atrophy, multiple sclerosis, narcolepsy, Niemann Pick disease, Parkinson's disease, Pelizaeus-Merzbacher Disease, Pick's disease, primary lateral sclerosis, prion diseases, progressive supranuclear palsy, Refsum's disease, Sandhoff disease, Schilder's disease, subacute combined degeneration of spinal cord secondary to Pernicious Anaemia, Spielmeyer-Vogt-Sjogren-Batten disease (also known as Batten disease), spinocerebellar ataxia, spinal muscular atrophy, Steele-Richardson-Olszewski disease, Tabes dorsalis, toxic encephalopathy.

Accordingly, a temperature-sensitive agent (e.g., a temperature-sensitive therapeutic agent) is administered to a subject so as to reduce or ameliorate symptoms associated with a particular disorder. Therapeutic endpoints for the treatment of cancer can include a reduction in the size or volume of a tumor, reduction in angiogenesis to the tumor, or reduction in metastasis of the tumor. If the tumor has been removed, another therapeutic endpoint can be regeneration of the tissue or organ removed. Effectiveness of cancer treatment can be measured using methods in the art, for example imaging of the tumor or detecting tumor markers or other indicators of the presence of the cancer. Therapeutic endpoints for the treatment of autoimmune diseases can include a reduction in the autoimmune response. Effectiveness of autoimmune disease treatment can be measured using methods in the art, for example measuring of autoimmune antibodies, wherein a reduction in such antibodies in the treated subject indicates that the therapy is successful. Therapeutic endpoints for the treatment of neurodegenerative disorders can include a reduction in neurodegenerative-related deficits, e.g., an increase in motor, memory or behavioral deficits. Effectiveness of treating neurodegenerative disorders can be measured using methods in the art, for example by measuring cognitive impairment, wherein a reduction in such impairment in the treated subject indicates that the therapy is successful. Therapeutic endpoints for the treatment of neurologic injuries can include a reduction in injury-related deficits, e.g., an increase in motor, memory or behavioral deficits. Effectiveness of treating neurologic injuries can be measured using methods in the art, for example by measuring mobility and flexibility, wherein an increase in such in the treated subject indicates that the therapy is successful. Treatment does not require 100% effectiveness. A reduction in the disease (or symptoms thereof) of at least about 10%, about 15%, about 25%, about 40%, about 50%, or greater, for example relative to the absence of treatment with the agent in human cells, is considered effective.

Temperature-sensitive agents (e.g., a temperature-sensitive therapeutic agents) of the present disclosure may also be used to treat atherosclerosis and/or a coronary heart disease in a subject in need thereof, by, for example, administering a temperature-sensitive agent (e.g., a temperature-sensitive therapeutic agent) of the present disclosure to the bloodstream of the subject such that the agent introduces/contacts and increases quality of vascular endothelial cells, thereby treating atherosclerosis and/or a coronary heart disease in the subject.

Temperature-sensitive agents (e.g., a temperature-sensitive therapeutic agents) of the present disclosure may also be used to provide resistance to one or more genotoxic agents in one or more human cells and/or a subject in need thereof.

Examples of disorders or diseases that can benefit from administration of a temperature-sensitive agent (e.g., a temperature-sensitive therapeutic agent) include those disorders or diseases that are associated with gene mutation(s), abnormal telomere length, or abnormal epigenetic modification(s). Further examples of disorders or diseases that can benefit from administration of a temperature-sensitive agent (e.g., a temperature-sensitive therapeutic agent) include cancer, autoimmune diseases, and diseases in which cell regeneration is beneficial, such as neurologic injuries or a neurodegenerative disorders, as well as blindness and deafness.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control.

Exemplary Embodiments

1. A method for transiently inducing a temperature-sensitive activity of a temperature-sensitive agent, comprising:
   i) incubating one or more cells comprising the temperature-sensitive agent at a permissive temperature to induce the temperature-sensitive activity for a period of time sufficient for the temperature-sensitive activity to produce an effect in the one or more cells; and
   ii) incubating the one or more cells at a non-permissive temperature, wherein the non-permissive temperature reduces the temperature-sensitive activity of the temperature-sensitive agent,
wherein the temperature-sensitive agent comprises a therapeutic agent and the effect comprises a therapeutic effect.

2. The method of embodiment 1, further comprising before step i): contacting the one or more cells with the temperature-sensitive agent.

3. The method of embodiment 2, wherein the one or more cells are at the permissive temperature when contacted with the temperature-sensitive agent.

4. The method of any one of embodiments 1-3, further comprising administering the one or more cells to a subject in need of the therapeutic effect.

5. The method of any one of embodiments 1-3, wherein incubating the one or more cells at a non-permissive temperature comprises administering the one or more cells to a subject in need of the therapeutic effect, wherein the subject's body temperature is the non-permissive temperature.

6. The method of embodiment 4 or 5, wherein the one or more cells are further incubated at the non-permissive temperature prior to administering the one or more cells to the subject 7. The method of any one of embodiments 1-6, wherein the one or more cells are embryonic stem cells or induced pluripotent stem cells.

8. The method of embodiment 7, wherein the therapeutic effect comprises the differentiation of said cells into a desired cell type.

9. The method of embodiment 8, wherein the desired cell type is selected from the group consisting of a neuron, a glia cell, and an endothelial cell.

10. The method of any one of embodiments 2-9, wherein the one or more cells were isolated from the subject before contacting the one or more cells with the temperature-sensitive agent.

11. A method for transiently inducing a temperature-sensitive activity of a temperature-sensitive agent in a subject, wherein one or more cells of the subject comprise the temperature-sensitive agent, wherein the temperature-sensitive activity of the temperature-sensitive agent is induced at a permissive temperature, and wherein the permissive temperature is lower than the body temperature of the subject, comprising:
   i) lowering the body temperature of the subject to the permissive temperature;
   ii) maintaining said lowered body temperature for a period of time sufficient for the temperature-sensitive activity to induce an effect in the subject; and
   iii) increasing the body temperature of the subject back to normal body temperature.

12. A method for transiently inducing a temperature-sensitive activity of a temperature-sensitive agent in a subject, wherein the temperature-sensitive activity of the temperature-sensitive agent is induced at a permissive temperature, and wherein the permissive temperature is lower than the body temperature of the subject, comprising:
   i) lowering the body temperature of the subject to the permissive temperature;
   ii) administering the temperature-sensitive agent to one or more cells of the subject;
   iii) maintaining said lowered body temperature for a period of time sufficient for the temperature-sensitive activity to induce an effect in the subject; and
   iv) increasing the body temperature of the subject back to normal body temperature, wherein step (i) is performed before, after, or simultaneously with step (ii).

13. The method of embodiment 12, wherein the temperature-sensitive agent is administered systemically.

14. The method of embodiment 13, wherein the temperature-sensitive agent is administered intravenously.

15. The method of embodiment 12, wherein the temperature-sensitive agent is administered to a specific tissue or organ of the subject.

16. The method of embodiment 15, wherein the temperature-sensitive agent is administered to the brain and spinal cord by epidural injection.

17. The method of embodiment 15, wherein the temperature-sensitive agent is administered by percutaneous injection into a target organ.

18. The method of embodiment 15, wherein the temperature-sensitive agent is administered by endoscopy with an injection needle catheter into a target organ.

19. The method of embodiment 15, wherein the temperature-sensitive agent is administered by angiocatheter into a target organ.

20. The method of any one of embodiments 17-19, wherein the target organ is selected from the group consisting of the liver, kidneys, skeletal muscles, cardiac muscles, pancreas, spleen, heart, brain, spinal cord, skin, eye, lung, intestine, thymus, bone marrow, bone, and cartilage.

21. The method of embodiment 12, wherein the temperature-sensitive agent is administered by inhalation.

22. The method of any one of embodiments 11-21, wherein altering the body temperature of a subject comprises using a targeted temperature management (TTM) procedure, wherein the TTM procedure comprises application to the subject of one of the group consisting of a cooling catheter, a cooling blanket, and ice.

23. The method of any one of embodiments 11-22, wherein the subject is a mammalian subject, optionally wherein the subject is a human.

24. The method of any one of embodiments 11-23, wherein the temperature-sensitive agent comprises a therapeutic agent, and the effect comprises a therapeutic effect.

25. The method embodiment 24, or any one of embodiments 1-10, wherein the therapeutic agent is encoded by a coding region of a heterologous nucleic acid of a temperature-sensitive viral vector.

26. The method of embodiment 25, wherein said temperature-sensitive viral vector is selected from the group consisting of a Sendai virus, an Adeno virus, an Adeno-associated virus, a Retrovirus, and an Alphavirus.

27. The method of embodiment 26, wherein said temperature-sensitive viral vector is an Alphavirus.

28. The method of embodiment 27, wherein said Alphavirus is selected from the group consisting of a Venezuelan equine encephalitis virus, a Sindbis virus, and a Semliki Forrest virus.

29. The method of embodiment 26, wherein the temperature-sensitive viral vector is a Sendai virus.

30. The method of any one of embodiments 25-29, wherein the therapeutic agent is selected from the group consisting of a non-coding RNA, a siRNA, a shRNA, and an endonuclease editing system.

31. The method of any one of embodiments 25-29, wherein the therapeutic agent is a protein.

32. The method of embodiment 31, wherein the protein is a transcription factor, optionally wherein the transcription factor is selected from the group consisting of human neurogenin-3 (NGN3), and human ETS translocation variant 2 (ETV2).

33. The method of embodiment 31, wherein the protein is a growth factor, optionally wherein the growth factor is selected from the group consisting of brain-derived neurotrophic factor (BDNF) and nerve growth factor (NGF).

34. The method of any one of embodiments 25-33, wherein the temperature sensitive activity comprises replication and transcription of the temperature-sensitive viral vector.

35. The method of embodiment 24, or any one of embodiments 1-10, wherein the therapeutic agent is encoded by a coding region of a temperature-sensitive self-replicating RNA.

36. The method of embodiment 35, wherein said self-replicating RNA comprises an Alphavirus replicon lacking a viral structural protein coding region.

37. The method of embodiment 36, wherein said Alphavirus is selected from the group consisting of a Venezuelan equine encephalitis virus, a Sindbis virus, and a Semliki Forrest virus.

38. The method of any one of embodiments 35-37, wherein the therapeutic agent is selected from the group consisting of a non-coding RNA, a siRNA, a shRNA, and an endonuclease editing system.

39. The method of any one of embodiments 35-37, wherein the therapeutic agent is a protein.

40. The method of embodiment 39, wherein the protein is a transcription factor, optionally wherein the transcription factor is selected from the group consisting of human neurogenin-3 (NGN3), and human ETS translocation variant 2 (ETV2).

41. The method of embodiment 39, wherein the protein is a growth factor, optionally wherein the growth factor is selected from the group consisting of brain-derived neurotrophic factor (BDNF) and nerve growth factor (NGF).

42. The method of any one of embodiments 35-41, wherein the temperature-sensitive activity comprises one or both of replication and transcription of the temperature-sensitive self-replicating RNA.

43. The method of any one of embodiments 25-42, wherein the coding region is operably linked to a promoter.

44. The method of any one of embodiments 1-10, wherein the period of time sufficient for the temperature-sensitive activity to produce a therapeutic effect ranges from about 12 hours to about 12 weeks, optionally wherein the period of time is from 1 to 7 days.

45. The method of any one of embodiments 11-43, wherein the period of time sufficient to induce an effect in the subject is from about 12 hours to about 7 days, optionally wherein the period of time is from about 12 hours to about 72 hours.

46. The method of any one of embodiments 1-45, wherein the permissive temperature ranges from 30° C. to 36° C. or from 38° C. to 50° C.

47. The method of embodiment 46, wherein the permissive temperature is 33° C.±0.5° C.

48. The method of embodiment 46 or embodiment 47, wherein the non-permissive temperature is 37° C.±0.5° C.

49. The method of any one of embodiments 1-48, wherein the one or more cells are human cells.

50. The method of embodiment 49, wherein the one or more human cells are adult stem cells, tissue stem cells, progenitor cells, embryonic stem cells, or induced pluripotent stem cells.

51. The method of embodiment 50, wherein the one or more human cells are selected from the group consisting of hematopoietic stem cells, mesenchymal stem cells, adipose stem cells, neuronal stem cells, and germ stem cells.

52. The method of embodiment 49, wherein the one or more human cells are somatic cells, mature cells, or differentiated cells.

53. The method of embodiment 52, wherein the one or more human cells are selected from the group consisting of epidermal cells, fibroblasts, lymphocytes, hepatocytes, epithelial cells, myocytes, chondrocytes, osteocytes, adipocytes, cardiomyocytes, pancreatic cells, pancreatic p cells, keratinocytes, erythrocytes, peripheral blood mononuclear cells (PBMC), neurons, glia cells, neurocytes, astrocytes, germ cells, sperm cells, and oocytes.

54. The method of embodiment 49, wherein the one or more human cells are human bone marrow cells.

55. The method of embodiment 54, wherein the human bone marrow cells are selected from the group consisting of hematopoietic stem cells, mesenchymal stem cells, and endothelial stem cells.

56. The method of embodiment 55, wherein the hematopoietic stem cells are CD34+.

57. The method of any one of embodiments 25-56, wherein the temperature-sensitive viral vector or the temperature-sensitive self-replicating RNA comprises a nonstructural protein coding region with an insertion of 12-18 nucleotides, wherein the insertion results in expression of a nonstructural Protein 2 (nsP2=helicase proteinase) comprising from 4 to 6 additional amino acids between beta sheet 5 and beta sheet 6 of the nsP2, optionally wherein the additional amino acids result in temperature-sensitivity of the viral vector or the self-replicating RNA.

58. The method of embodiment 57, wherein the additional amino acids comprise one sequence selected from the group consisting of SEQ ID NO:38 (GCGRT), SEQ ID NO:39 (TGAAA), and SEQ ID NO:40 (LRPHP).

59. The method of embodiment 57, wherein the additional amino acids comprise the sequence of SEQ ID NO:39 (TGAAA).

60. The method of embodiment 59, wherein the amino acid sequence of the NsP2 comprises one sequence selected from the group consisting of SEQ ID NOs:29-36.

61. A temperature-sensitive agent, wherein the agent is a temperature-sensitive viral vector or a temperature-sensitive self-replicating RNA comprising a nonstructural protein coding region with an insertion of 12-18 nucleotides, wherein the insertion results in expression of a nonstructural Protein 2 (nsP2=helicase proteinase) comprising from 4 to 6 additional amino acids between beta sheet 5 and beta sheet 6 of the nsP2, optionally wherein the additional amino acids result in temperature-sensitivity of the viral vector or the self-replicating RNA.

62. The temperature-sensitive agent of embodiment 61, wherein the additional amino acids comprise one sequence selected from the group consisting of SEQ ID NO:38 (GCGRT), SEQ ID NO:39 (TGAAA), and SEQ ID NO:40 (LRPHP).

63. The temperature-sensitive agent of embodiment 61, wherein the additional amino acids comprise the sequence of SEQ ID NO:39 (TGAAA).

64. The temperature-sensitive agent of embodiment 63, wherein the amino acid sequence of the NsP2 comprises one sequence selected from the group consisting of SEQ ID NOs:29-36.

65. The temperature-sensitive agent of any one of embodiments 61-64, wherein the agent is a temperature-sensitive Alphavirus vector.

66. The temperature-sensitive agent of any one of embodiments 61-64, wherein the agent is a temperature-sensitive self-replicating RNA comprising an Alphavirus replicon lacking a viral structural protein coding region.

67. The temperature-sensitive agent of embodiment 65 or embodiment 66, wherein the Alphavirus is selected from the group consisting of a Venezuelan equine encephalitis virus, a Sindbis virus, and a Semliki Forrest virus.

68. The temperature-sensitive agent of embodiment 65 or embodiment 66, wherein the Alphavirus is a Venezuelan equine encephalitis virus.

69. A method for transiently inducing a temperature-sensitive activity of a temperature-sensitive agent (ts-agent) in a subject, wherein one or more cells at or near the surface of the subject's body comprise the ts-agent, wherein the temperature-sensitive activity of the ts-agent is induced at a permissive temperature, and wherein the permissive temperature is the surface body temperature of the subject, comprising:
    i) maintaining the surface body temperature of the subject at the permissive temperature for a period of time sufficient for the temperature-sensitive activity to induce an effect in the subject; and
    ii) increasing the surface body temperature of the subject to a non-permissive temperature for a period of time sufficient for the temperature-sensitive activity to cease in the subject.

79. A method for transiently inducing a temperature-sensitive activity of a temperature-sensitive agent (ts-agent) in a subject, wherein the temperature-sensitive activity of the ts-agent is induced at a permissive temperature, and wherein the permissive temperature is the surface body temperature of the subject, comprising:
    i) administering the ts-agent to one or more cells at or near the surface of the subject's body; and
    ii) maintaining the surface body temperature of the subject at the permissive temperature for a period of time sufficient for the temperature-sensitive activity to induce an effect in the subject.

71. The method of embodiment 70, further comprising iii) increasing the surface body temperature of the subject to a non-permissible temperature for a period of time sufficient for the temperature-sensitive activity to cease in the subject.

72. The method of embodiment 70 or embodiment 71, wherein the temperature-sensitive agent is administered intradermally or subcutaneously.

73. The method of embodiment 70 or embodiment 71, wherein the temperature-sensitive agent is administered intramuscularly.

74. The method of any one of embodiments 69-73, wherein the non-permissive temperature is above 36° C., and the permissive temperature is below 36° C., optionally wherein the permissive temperature is from about 31° C. to about 34° C., or about 33° C.±0.5° C., and the non-permissive temperature is 37° C.±0.5° C.

75. The method of any one of embodiments 69-74, wherein a pharmaceutical agent is encoded by a coding region of the ts-agent or the ts-agent comprises a pharmaceutical agent, and the effect comprises a pharmaceutical effect, optionally wherein the pharmaceutical agent is a therapeutic agent and the pharmaceutical effect is a therapeutic effect, or wherein the pharmaceutical agent is a prophylactic agent and the pharmaceutical effect is a prophylactic effect.

76. The method of any one of embodiments 69-75, wherein the ts-agent is a temperature-sensitive viral vector and the temperature-sensitive activity comprises replication and transcription of the temperature-sensitive viral vector.

77. The method of embodiment 76, wherein the temperature-sensitive viral vector is selected from the group consisting of a Sendai virus, an Adeno virus, an Adeno-associated virus, a Retrovirus, and an Alphavirus.

78. The method of embodiment 76, wherein the temperature-sensitive viral vector is an Alphavirus, optionally wherein the Alphavirus is selected from the group consisting of a Venezuelan equine encephalitis virus, a Sindbis virus, and a Semliki Forrest virus.

79. The method of embodiment 76, wherein the temperature-sensitive viral vector is a Sendai virus.

80. The method of any one of embodiments 69-75, wherein the ts-agent is a temperature-sensitive self-replicating RNA and the temperature-sensitive activity comprises one or both of replication and transcription of the temperature-sensitive self-replicating RNA.

81. The method of embodiment 80, wherein the self-replicating RNA comprises an Alphavirus replicon lacking an Alphavirus viral structural protein coding region.

82. The method of embodiment 81, wherein the Alphavirus is selected from the group consisting of a Venezuelan equine encephalitis virus, a Sindbis virus, and a Semliki Forrest virus.

83. The method of embodiment 81, wherein the Alphavirus is a Venezuelan equine encephalitis virus.

84. The method of any one of embodiments 69-83, wherein the pharmaceutical agent is selected from the group consisting of a non-coding RNA, a siRNA, a shRNA, and an endonuclease editing system.

85. The method of any one of embodiments 69-83, wherein the pharmaceutical agent comprises a protein.

86. The method of embodiment 85, wherein the protein comprises an antigen of a pathogen.

87. The method of embodiment 86, wherein the pathogen comprises one or more of a virus, a bacterium, a protozoan, and a fungus.

88. The method of embodiment 86 or embodiment 87, wherein the antigen comprises a surface protein or fragment thereof of the pathogen.

89. The method of any one of embodiments 69-88, wherein the period of time sufficient for the temperature-sensitive activity to produce an effect ranges from about 12 hours to about 12 weeks, optionally wherein the period of time is from 1 to 7 days.

90. The method of any one of embodiments 69-88, wherein the period of time sufficient to induce an effect in the subject is from about 12 hours to about 7 days, optionally wherein the period of time is from about 12 hours to about 72 hours.

91. An immunogenic composition for stimulating an immune response against a pathogen in a subject, comprising an excipient and a temperature-sensitive agent (ts-agent), wherein the ts-agent is a temperature-sensitive viral vector or a temperature-sensitive self-replicating RNA encoding an antigen of the pathogen, and wherein the ts-agent is capable of expressing the antigen at a permissive temperature but not at a non-permissive temperature.

92. The composition of embodiment 91, wherein the pathogen comprises one or more of a virus, a bacterium, a protozoan, and a fungus.

93. The composition of embodiment 91 or embodiment 92, wherein the antigen comprises a surface protein or fragment thereof of the pathogen.

94. The composition of embodiment 93, wherein the pathogen is a virus, and the virus is different than the viral vector.

95. The composition of embodiment 94, wherein the virus is a coronavirus and the antigen comprises a spike protein or fragment thereof of the coronavirus.

96. The composition of embodiment 95, wherein the coronavirus is 2019-nCoV and the antigen comprises a receptor-binding domain (RBD) of the 2019-nCoV.

97. The composition of embodiment 96, wherein the amino acid sequence of the RBD comprises SEQ ID NO:44, or the amino acid sequence at least 75%, 85%, 90%, 95%, 96%, 97%, 98% or 99% identical to SEQ ID NO:44.

98. The composition of embodiment 95, wherein the coronavirus is 2019-nCoV and the antigen comprises an extracellular region of the spike protein comprising the amino acid sequence of residues 16-1213 of SEQ ID NO:41, or the amino acid sequence at least 75%, 85%, 90%, 95%, 96%, 97%, 98% or 99% identical to SEQ ID NO:41.

99. The composition of any one of embodiments 91-98, wherein the non-permissive temperature is above 36° C., and the permissive temperature is below 36° C., optionally wherein the permissive temperature is from about 31° C. to about 34° C., or about 33° C.±0.5° C., and the non-permissive temperature is 37° C.±0.5° C.

100. The composition of any one of embodiments 91-99, wherein the ts-agent is a temperature-sensitive self-replicating RNA.

101. The composition of embodiment 100, wherein the self-replicating RNA comprises an Alphavirus replicon lacking a viral structural protein coding region.

102. The composition of embodiment 101, wherein the Alphavirus is selected from the group consisting of a Venezuelan equine encephalitis virus, a Sindbis virus, and a Semliki Forrest virus.

103. The composition of embodiment 101, wherein the Alphavirus is a Venezuelan equine encephalitis virus.

104. The composition of any one of embodiments 91-99, wherein the ts-agent is a temperature-sensitive viral vector.

105. The composition of embodiment 104, wherein the viral vector is selected from the group consisting of a Sendai virus, an Adeno virus, an Adeno-associated virus, a Retrovirus, and an Alphavirus.

106. The composition of embodiment 105, wherein the Alphavirus is selected from the group consisting of a Venezuelan equine encephalitis virus, a Sindbis virus, and a Semliki Forrest virus.

107. The composition of embodiment 105, wherein the viral vector is a Sendai virus.

108. The method of any one of embodiments 69-90 or the composition of any one of embodiments 91-107, wherein the subject is a mammalian subject, optionally wherein the subject is a human.

109. The composition of any one of embodiments 91-108, wherein the pathogen is a mammalian pathogen, optionally wherein the pathogen is a human pathogen.

110. A method for stimulating an immune response against a pathogen in a mammalian subject, comprising administering the immunogenic composition of embodiment 109 to a mammalian subject so as to stimulate an immune response against the antigen in the mammalian subject, optionally wherein the mammalian subject is a human subject.

111. The method of embodiment 110, wherein the immunogenic composition is administered:
  i) intradermally or subcutaneously; or
  ii) intramuscularly.

112. The method of embodiment 110, wherein the immunogenic composition is administered intranasally.

EXAMPLES

Abbreviations: Aura (Aura virus); BFV (Barmah Forest virus); GFP (green fluorescent protein); GOI (gene of interest); IRES (internal ribosome entry site); LUC (luciferase); OD (optical density); ONNV (O'nyong-nyong virus); RBD (receptor binding domain); RRV (Ross River virus); SeV (Sendai virus); SeVts (temperature-sensitive Sendai virus); SFV (Semliki Forest virus); shRNA (short hairpin RNA);

SINV (Sindbis virus); srRNA (self-replicating RNA); ts (temperature-sensitive); ts-agent (temperature-sensitive-agent); VEEV (Venezuelan equine encephalitis virus); and WEEV (Western equine encephalitis virus).

The following examples are provided to illustrate certain particular features and/or embodiments. The examples are not intended to limit the disclosure as claimed.

Example 1: Temperature-Sensitive Agents

This example describes a temperature-sensitive agent (ts-agent) that functions at a lower or higher temperature than normal body temperature, but does not function, or shows reduced functionality, at normal body temperature. The ts-agents are suitable for use in ex vivo, semi in vivo, and in vivo therapies. Temperature-sensitive viral vectors and self-replicating RNAs are engineered to express a gene of interest (GOI), a short hairpin RNA (shRNA), a long non-coding RNA, and/or other genetic element(s). For instance, proteins with temperature-sensitive mutations, are functional at a lower temperature (e.g., at 30° C.), but are not functional at a normal body temperature (e.g., at 37° C.). Unless otherwise specified, normal body temperature is normal human body temperature of 37° C.±0.5° C.

Example 2: Temperature-Sensitive Sendai Virus Vectors (SeVts)

This example describes temperature-sensitive Sendai virus vectors (SeVts), which can be used for temperature-specific gene expression. Sendai virus vectors are based on the Sendai virus, a single-stranded RNA virus of the Paramyxovirus subfamily. SeV18/TS15ΔF is a temperature-sensitive Sendai virus vector, which allows for viral replication and gene expression when held at 32-35° C. However, viral replication ceases at non-permissive temperatures of 37° C. and above (Ban et al., PNAS 2011).

Example 3: Temperature-Sensitive Self-Replicating RNAs (srRNAs)

This example describes the finding that a mutation in nsP2 protein encoded in a Venezuelan Equine Encephalitis Virus (VEEV) Vector exhibits temperature sensitivity. The temperature-sensitive system permits expression of a gene of interest (GOI) at 30° C.-33° C., but not at 37° C. and above. The srRNA vector permits higher expression of the GOI than a synthetic RNA encoding the GOI. The expression of the GOI is turned off, when the temperature is shifted to 37° C. (e.g., a non-permissive temperature). A specific temperature-sensitive mutation (mutation 2) described below is in a well-conserved region of among Alphaviruses. Compared to Sendai Virus Vectors (SeVts), srRNAts may be more attractive for some applications, as srRNAts can be utilized in non-viral RNA expression systems.

Materials and Methods
Cell Culture
A human Adipose Stem Cell-derived iPS cell line (ADSC-iPS cells) was purchased from System Biosciences (Palo Alto, Calif.). Cells were routinely maintained as undifferentiated human pluripotent stem cells (hPSCs) according to the standard hPSC culture method. Briefly, cells were cultured in StemFit basic02 (Ajinomoto, Japan) supplemented with 100 ng/ml FGF2. Further, cells were cultured on cell culture dishes coated with a laminin-511 substrate (iMatrix-511, Nippi, Japan).

VEEV Vector
A VEEV vector plasmid was assembled using synthesized DNA fragments based on the publicly available sequence information (T7-VEE-IRES-Puro, herein after "srRNA1 wt"). Per Yoshioka et al., 2013, the VEEV vector backbone was originally derived as in Petrakova et al., 2005. 7480 candidate sequences identified by insertional mutagenesis and massively parallel sequencing (Beitzel et al., 2010) were used to derive potential temperature-sensitive mutants. The original large-scale screen was performed by transposon-mediated insertion of 15 bp into the VEEV genome (FIG. 1A). Subsequently, a large number of 15-bp-insertion VEEV mutants that were able to proliferate at 30° C. or 40° C. were isolated. Although these data provided initial mutants for further research, it was not known whether these sequences exhibit temperature sensitivity, such as permissiveness at 32° C. or 33° C. and non-permissiveness at 37° C. Three mutant sequences—Mutant 1 (ts1, FIG. 1B), Mutant 2 (ts2, FIG. 1C), and Mutant 3 (ts3, FIG. 1D) were selected from a total of 7480 candidate mutant sequences (Data Set Si from Beitzel et al., 2010). These mutant DNA fragments (FIG. 2) were synthesized and cloned into the VEEV vector and named srRNA1ts1 (mutant1), srRNA1ts2 (mutant 2), srRNA1ts3 (mutant 3). A mutant 4 was designed, which includes the 5'-region of virus sequence (5'-UTR and a part of N-terminal protein sequence of RNA-dependent RNA polymerase known to include a 51-nt conserved sequence element (CSE)). In this case, nucleotides were systematically changed to less thermo-stable variants (e.g., G→A), while maintaining the amino acid sequences (FIG. 3). The sequence of this region in srRNA1ts2 was replaced to generate srRNA1ts4 (i.e., containing both mutant 4 and mutant 2). Synthetic RNAs were produced from these vectors according to Yoshioka et al., 2013.

Results
Assessing Temperature-Sensitivity of srRNA1ts2-GFP and srRNA1ts3-GFP at 30° C., 32° C., and 37° C.

Figure 4B:
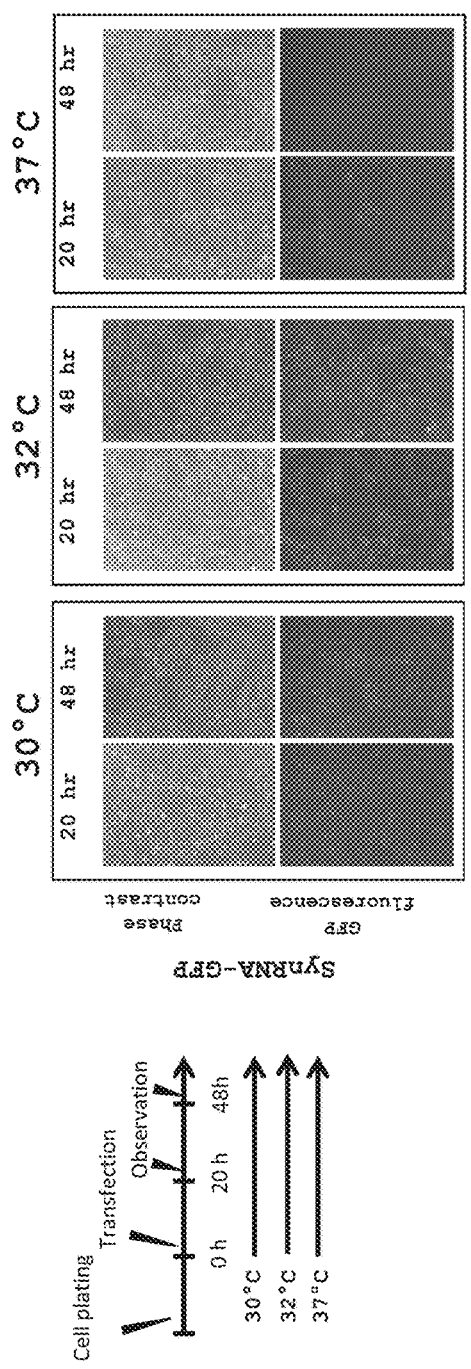

ADSC-iPSC cells were plated on a 24-well plate at a density of 80,000 cells/well. After 24 hours, cells were transfected with srRNA 1 wt-GFP, srRNA1ts2-GFP, or srRNA1ts3-GFP. For transfection, each well of a 24-well plate was treated with, 0.5 μg synthetic RNA (srRNA) mixed with 1 μl of JetMessenger (Polyplus) transfection reagent at a final volume of 50 μl. After adding the transfection complex to the cells, 450 μl of culture media was added. The cells were incubated at either 30° C., 32° C., or 37° C. At 6 hours after transfection, the medium was changed to remove the transfection complex. The phase-contrast and fluorescent images were taken at 20 hours and 48 hours. FIG. 4A shows that wild type (srRNA1wt-GFP) strongly expressed GFP at 37° C., but only weakly expressed GFP at both 30° C. and 32° C. By contrast, mutant 2 (srRNA1ts2-GFP) expressed GFP at 30° C. and 32° C., but not at 37° C. Mutant 3 (srRNA1ts3-GFP) expressed GFP at 30° C. and 32° C., but also expressed GFP at 37° C. Based on these results, mutant 2 was selected for further development. As expected, srRNA showed much higher expression of GFP, compared to the GFP expression levels that were achieved by a single transfection of synthetic mRNA encoding the GFP (FIG. 4B).

Assessing Temperature-Sensitivity of srRNA1ts1-GFP and srRNA1Ts2-GFP at 32° C.

ADSC-iPSC cells were plated on a 24-well plate at the density of 50,000 cells/well. After 24 hours, cells were transfected with srRNA 1 wt-GFP, srRNA1ts2-GFP, or srRNA1ts1-GFP. For transfection, each well of a 24-well plate was treated with, 0.5 μg synthetic RNA (srRNA) mixed with 1 μl of JetMessenger (Polyplus) transfection reagent at a final volume of 50 µl. After adding the transfection complex to the cells, 450 µl of culture media was added. The cells were incubated at 32° C. At 6 hours after transfection, the medium was changed to remove the transfection complex. The phase-contrast and fluorescent images were taken at 24, 48, 72, 96, 120, 144, 168, 192, 240, and 288 hours.

Figure 5:
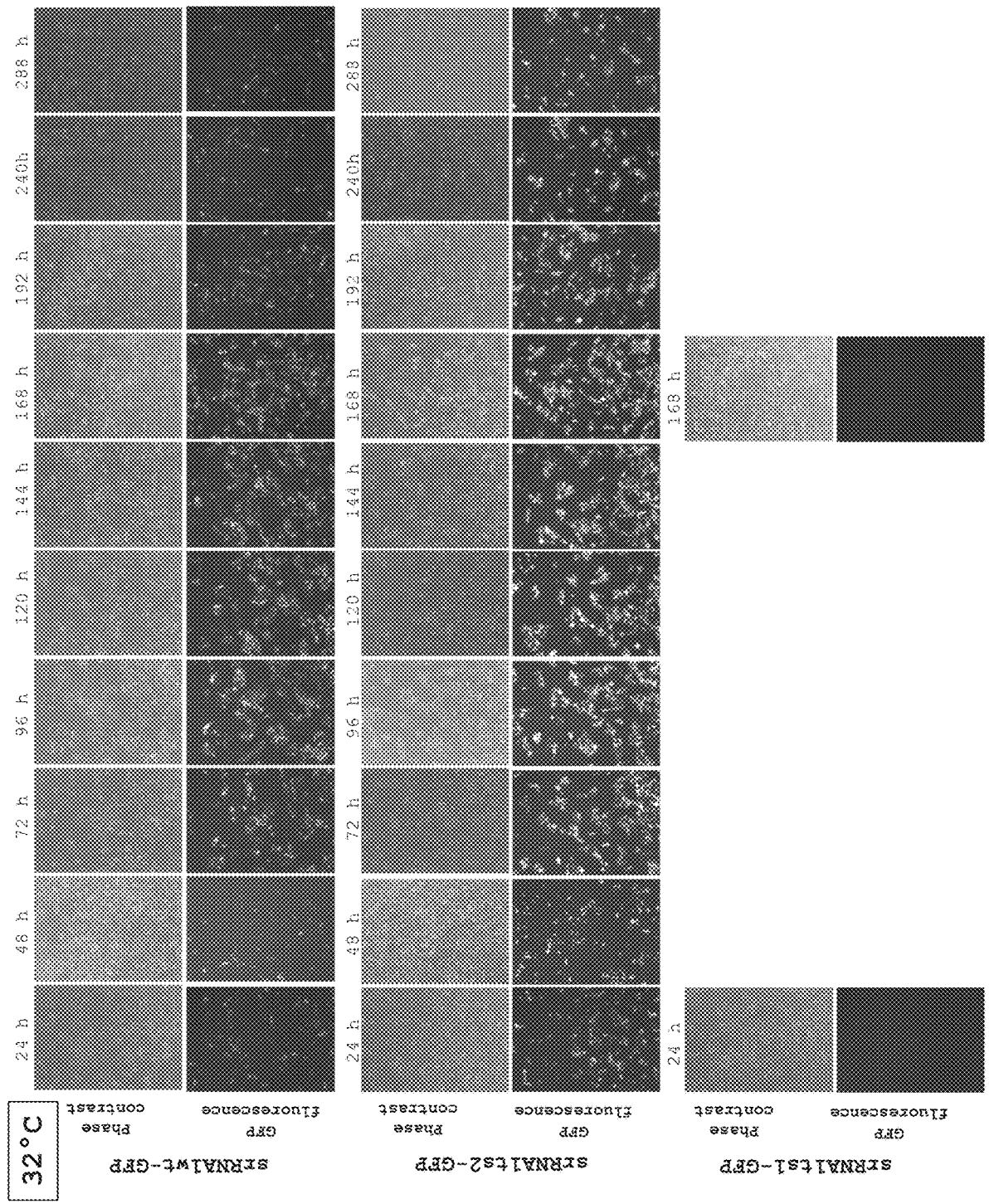
FIG. 5 depicts testing temperature-sensitivity of srRNA1ts1 and srRNA1ts2 at 32° C. Wild type (srRNA1 wt-GFP) and mutant (srRNA1ts2-GFP and srRNA1ts1-GFP) self-replicating RNA (srRNA) vectors were generated. RNAs produced by in vitro transcription were transfected into human induced pluripotent stem cells (ADSC-iPSC line). Cells were cultured in CO$_2$ incubators maintained at 32° C. Pictures of cells were obtained at 24, 48, 72, 96, 120, 144, 168, 192, 240, 288 hours. For the srRNA1ts1-GFP, only pictures of 24 hours and 168 hours were taken. The upper panels show phase-contrast images and the lower panels show fluorescence images detecting expression of GFP.

FIG. 5 shows the results. The GFP expression from wild type (srRNA1 wt-GFP) started at 24 hours and continued until the end of the observation period (at 288 hours), but was very weak throughout the time course. By contrast, the GFP expression from a mutant 2 (srRNA1ts2-GFP) was very strong throughout the time course. Mutant 1 (srRNA1ts1-GFP) did not express GFP at all (based on observation at 24 hours and 168 hours). Based on these results, mutant 2 was selected for further development.

Assessing Temperature-Sensitivity of srRNA1ts2-GFP and srRNA1ts4-GFP at 32° C., 33° C., and 37° C.

ADSC-iPSC cells were plated on a 24-well plate at the density of 50,000 cells/well. After 24 hours, cells were transfected with srRNA 1ts2-GFP, or srRNA1ts4-GFP. For transfection, each well of a 24-well plate was treated with, 0.5 µg synthetic RNA (srRNA) mixed with 1 µl of JetMessenger (Polyplus) transfection reagent at a final volume of 50 µl. After adding the transfection complex to the cells, 450 µl of culture media was added. The cells were incubated at either 32° C., 33° C., or 37° C. At 6 hours after transfection, the medium was changed to remove the transfection complex. The phase-contrast and fluorescent images were taken at 20, 48, and 96 hours.

Figure 6:
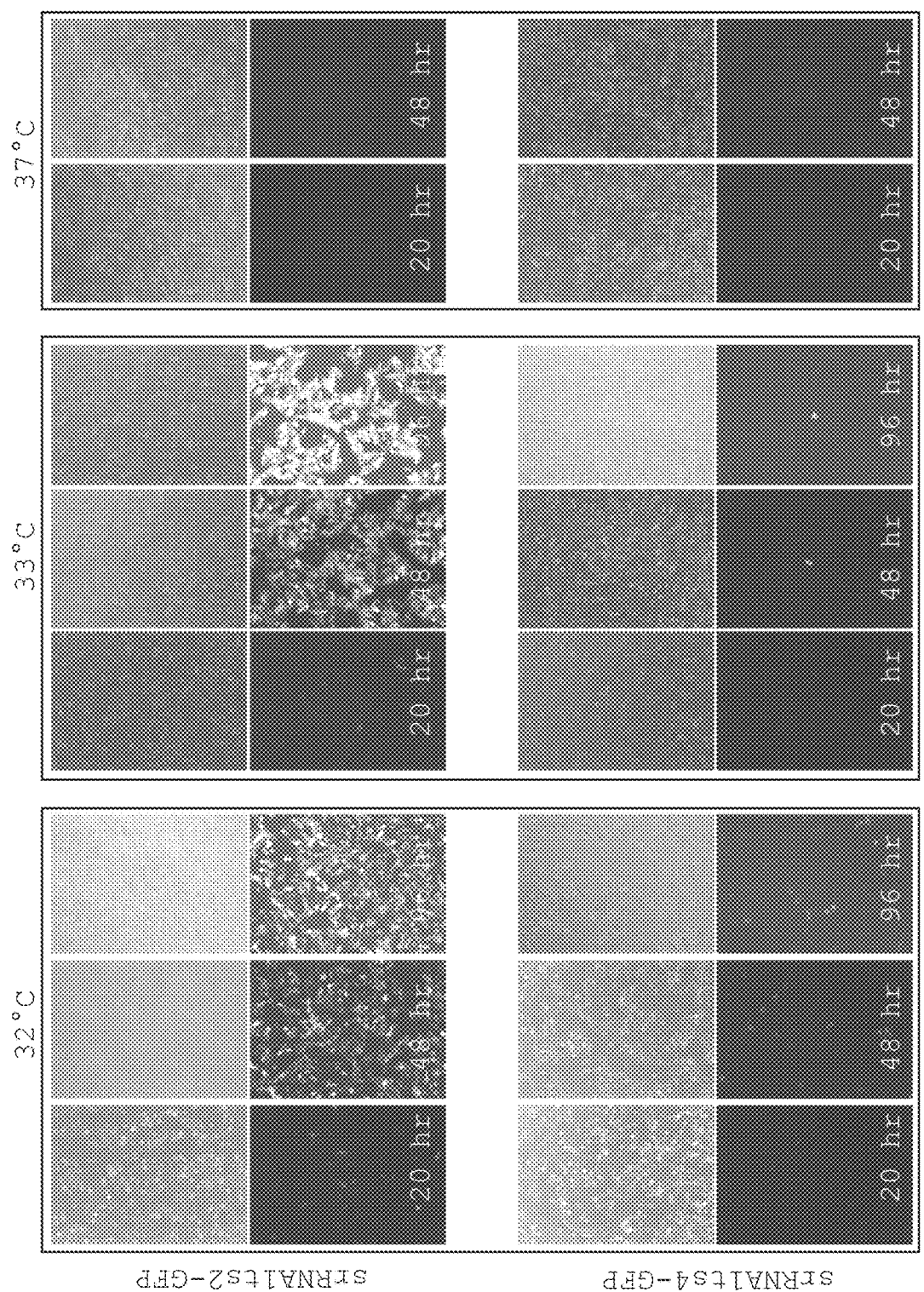
FIG. 6 depicts testing temperature-sensitivity of srRNA1ts2 and srRNA1ts4 at 32° C., 33° C., 37° C. Mutant (srRNA1ts2-GFP and srRNA 1ts4-GFP) self-replicating RNA (srRNA) vectors were generated. RNAs produced by in vitro transcription were transfected into human induced pluripotent stem cells (ADSC-iPSC line). Cells were cultured in CO$_2$ incubators maintained at 32° C., 33° C., 37° C., respectively. Pictures of cells were obtained at 20, 48, 96 hours. The upper panels show phase-contrast images and the lower panels show fluorescence images detecting expression of GFP.

FIG. 6 shows the results. At 32° C. and 33° C., the GFP expression from mutant 2 (srRNA1ts2-GFP) started as early as 20 hours, but significantly increased at 48 hours, and further increased at 96 hours. The expression of GFP was stronger at 33° C. than at 32° C. Consistent with the experiments above, GFP was not expressed at all at 37° C. The srRNA1ts4-GFP (containing both a mutant 2 and mutant 4) showed a similar temperature profile to srRNA1ts2-GFP, but the GFP expression was much weaker overall. Based on these results, mutant 2 was selected for further development.

Assessing Temperature-Sensitivity of srRNA1ts2-GFP at 32° C.

ADSC-iPSC cells were plated on a 24-well plate at the density of 80,000 cells/well. After 24 hours, cells were transfected with srRNA 1ts2-GFP. For transfection, each well of a 24-well plate was treated with, 0.5 µg synthetic RNA (srRNA) mixed with 1 µl of JetMessenger (Polyplus) transfection reagent at a final volume of 50 µl. After adding the transfection complex to the cells, 450 µl of culture media was added. The cells were incubated at 32° C. At 6 hours after transfection, the medium was changed to remove the transfection complex. The medium was changed every day. The srRNA1ts2-GFP vector contains a puromycin N-acetyltransferase (pac) selection gene inserted after the "IRES" sequence, and thus, can be selected using puromycin. The experiments were done in the absence (upper panel) or presence (lower panel) of 1 µg/ml of puromycin. For the cells with puromycin selection, puromycin was added at 48 hours and 72 hours. The phase-contrast and fluorescent images were taken at 24, 48, 72, 96, 144, 168, 192 hours.

Figure 7:
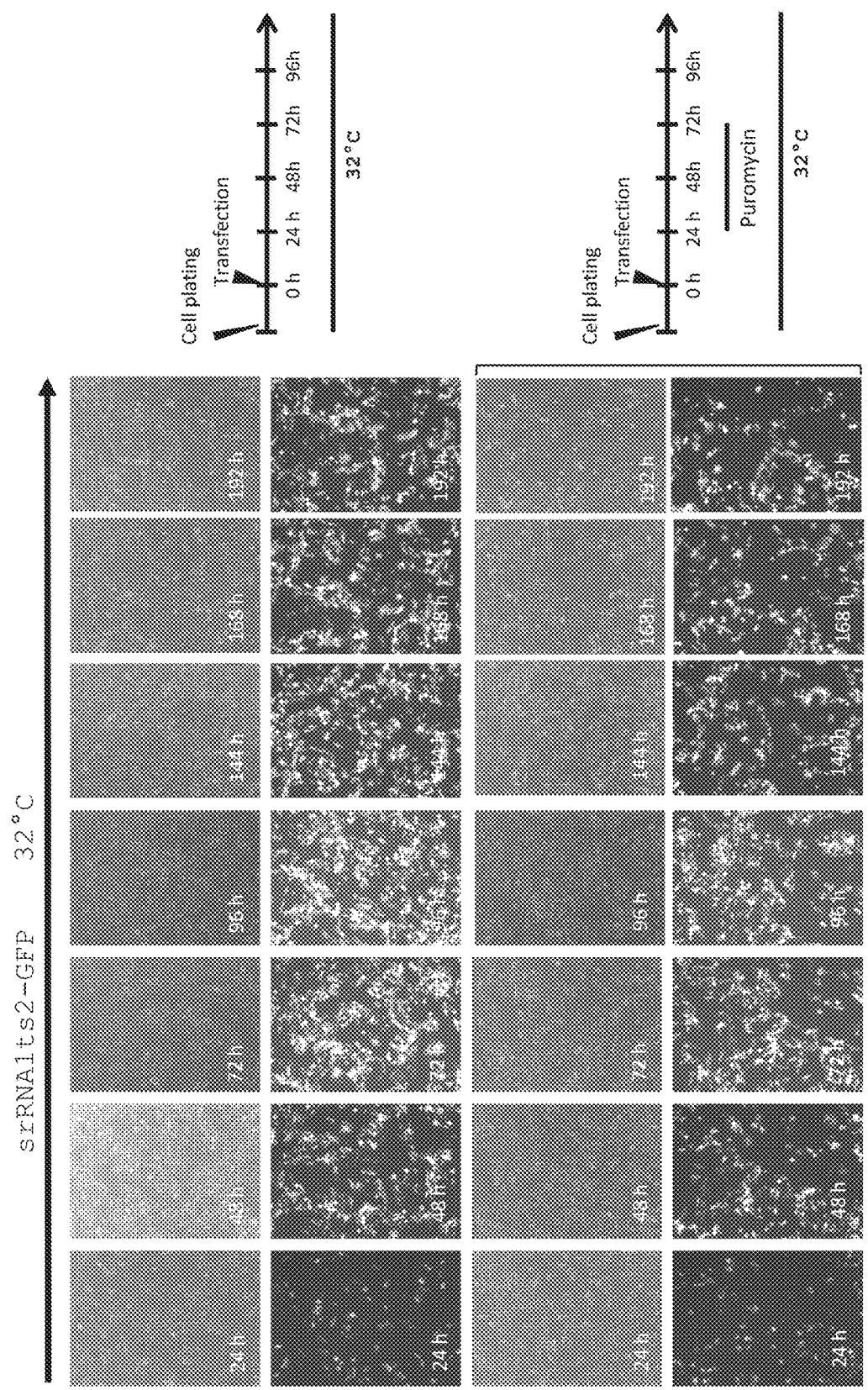
FIG. 7 depicts testing temperature-sensitivity of mutant srRNA1ts2-GFP maintained at 32° C. RNAs produced by in vitro transcription of a mutant vector (srRNA1ts2-GFP) were transfected into human induced pluripotent stem cells (ADSC-iPSC line). Cells were cultured in CO$_2$ incubators maintained at 32° C. The srRNA1ts2-GFP vector contains a puromycin N-acetyltransferase (pac) selection gene inserted after the "IRES" sequence, and thus, transfected cells can be selected using puromycin. The experiments were done in the absence (upper panel) or presence (lower panel) of 1 µg/ml of puromycin. Pictures of cells were obtained at 24, 48, 96, 144, 168, 192 hours. The upper panels show phase-contrast images and the lower panels show fluorescence images detecting expression of GFP.

FIG. 7 shows the results. At 32° C., the GFP expression from srRNA1ts2-GFP started as early as 24 hours, but significantly increased at 48 hours, and peaked at 72 hours and 96 hours. The expression of GFP continued until the end of observation period (at 192 hours). The expression pattern of GFP did not seem to be altered by the addition of puromycin.

Assessing Temperature-Sensitivity of srRNA1ts2-GFP Switched from 32° C. to 37° C. after 24 Hours.

ADSC-iPSC cells were plated on a 24-well plate at the density of 80,000 cells/well. After 24 hours, cells were transfected with srRNA 1ts2-GFP. For transfection, each well of a 24-well plate was treated with, 0.5 µg synthetic RNA (srRNA) mixed with 1 µl of JetMessenger (Polyplus) transfection reagent at a final volume of 50 µl. After adding the transfection complex to the cells, 450 µl of culture media was added. The cells were incubated at 32° C. At 6 hours after transfection, the medium was changed to remove the transfection complex. The medium was changed every day. The srRNA1ts2-GFP vector contains a puromycin N-acetyltransferase (pac) selection gene inserted after the "IRES" sequence, and thus, can be selected using puromycin. The experiments were done in the absence (upper panel) or presence (lower panel) of 1 µg/ml of puromycin. For the cells with puromycin selection, puromycin was added at 48 hours and 72 hours. To test the effects of temperature shift, the cell cultures were transferred to a $CO_2$ incubator maintained at 37° C. at 24 hours (24 hours after the transfection). The phase-contrast and fluorescent images were taken at 24, 48, 72, 96, 144, 168, 192 hours.

Figure 8:
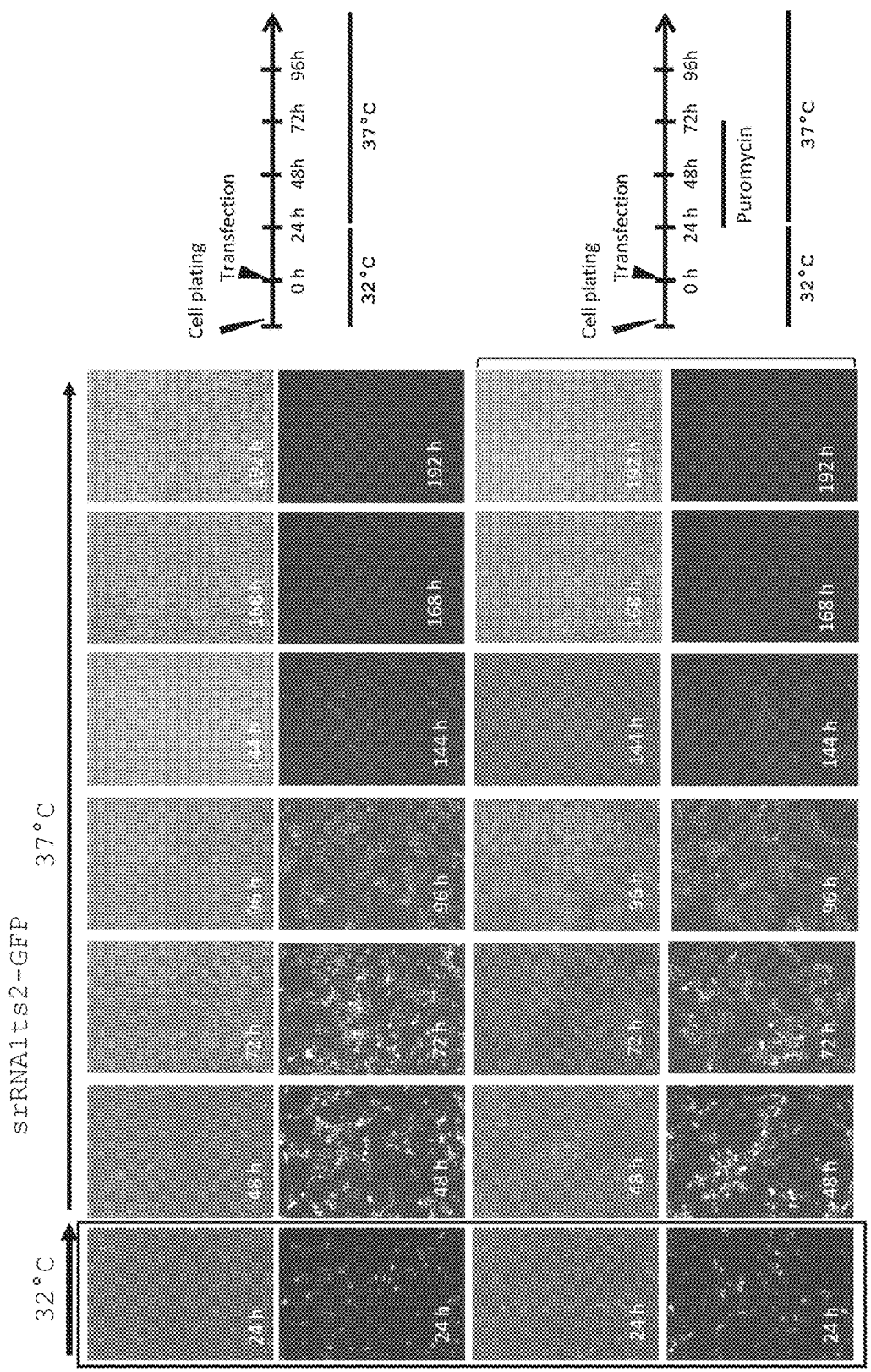
FIG. 8 depicts testing temperature-sensitivity of mutant srRNA1ts2-GFP with a temperature switch from 32° C. to 37° C. at 24 hours. RNAs produced by in vitro transcription of a mutant vector (srRNA1ts2-GFP) were transfected into human induced pluripotent stem cells (ADSC-iPSC line). Cells were cultured in $CO_2$ incubators maintained at 32° C. At 24 hours, cells were transferred to a $CO_2$ incubator maintained at 37° C. The srRNA1ts2-GFP vector contains a puromycin N-acetyltransferase (pac) selection gene inserted after the "IRES" sequence, and thus, transfected cells can be selected using puromycin. The experiments were done in the absence (upper panel) or presence (lower panel) of 1 µg/ml of puromycin. Pictures of cells were obtained at 24, 48, 96, 144, 168, 192 hours. The upper panels show phase-contrast images and the lower panels show fluorescence images detecting expression of GFP.

FIG. 8 shows the results. At 32° C., the GFP expression from srRNA1ts2-GFP started as early as 24 hours, but continued to increase even after the switching of temperature to 37° C. at 24 hours. The expression of GFP peaked at 48, and then, started to decrease. By 96 hours, the GFP expression became very weak and by 144 hours the GFP expression could not be detected any more. Subsequently, there was no GFP expression until the end of observation period at 192 hours. Thus, the expression of the GOI (represented here by GFP) was rapidly turned off, when the temperature shifted from 33° C. (a permissive temperature) to 37° C. (a non-permissive temperature). The expression pattern of GFP did not seem to be altered by the addition of puromycin.

Assessing Temperature-Sensitivity of srRNA1ts2-GFP Switched from 32° C. to 37° C. after 48 Hours.

ADSC-iPSC cells were plated on a 24-well plate at the density of 80,000 cells/well. After 24 hours, cells were transfected with srRNA 1ts2-GFP. For transfection, each well of a 24-well plate was treated with, 0.5 µg synthetic RNA (srRNA) mixed with 1 µl of JetMessenger (Polyplus) transfection reagent at a final volume of 50 µl. After adding the transfection complex to the cells, 450 µl of culture media was added. The cells were incubated at 32° C. At 6 hours after transfection, the medium was changed to remove the transfection complex. The medium was changed every day. The srRNA1ts2-GFP vector contains a puromycin N-acetyltransferase (pac) selection gene inserted after the "IRES" sequence, and thus, can be selected using puromycin. The experiments were done in the absence (upper panel) or presence (lower panel) of 1 µg/ml of puromycin. For the cells with puromycin selection, puromycin was added at 48 hours and 72 hours. To test the effects of temperature shift, the cell cultures were transferred to a $CO_2$ incubator maintained at 37° C. at 48 hours (48 hours after the transfection). The phase-contrast and fluorescent images were taken at 24, 48, 72, 96, 144, 168, 192 hours.

Figure 9:
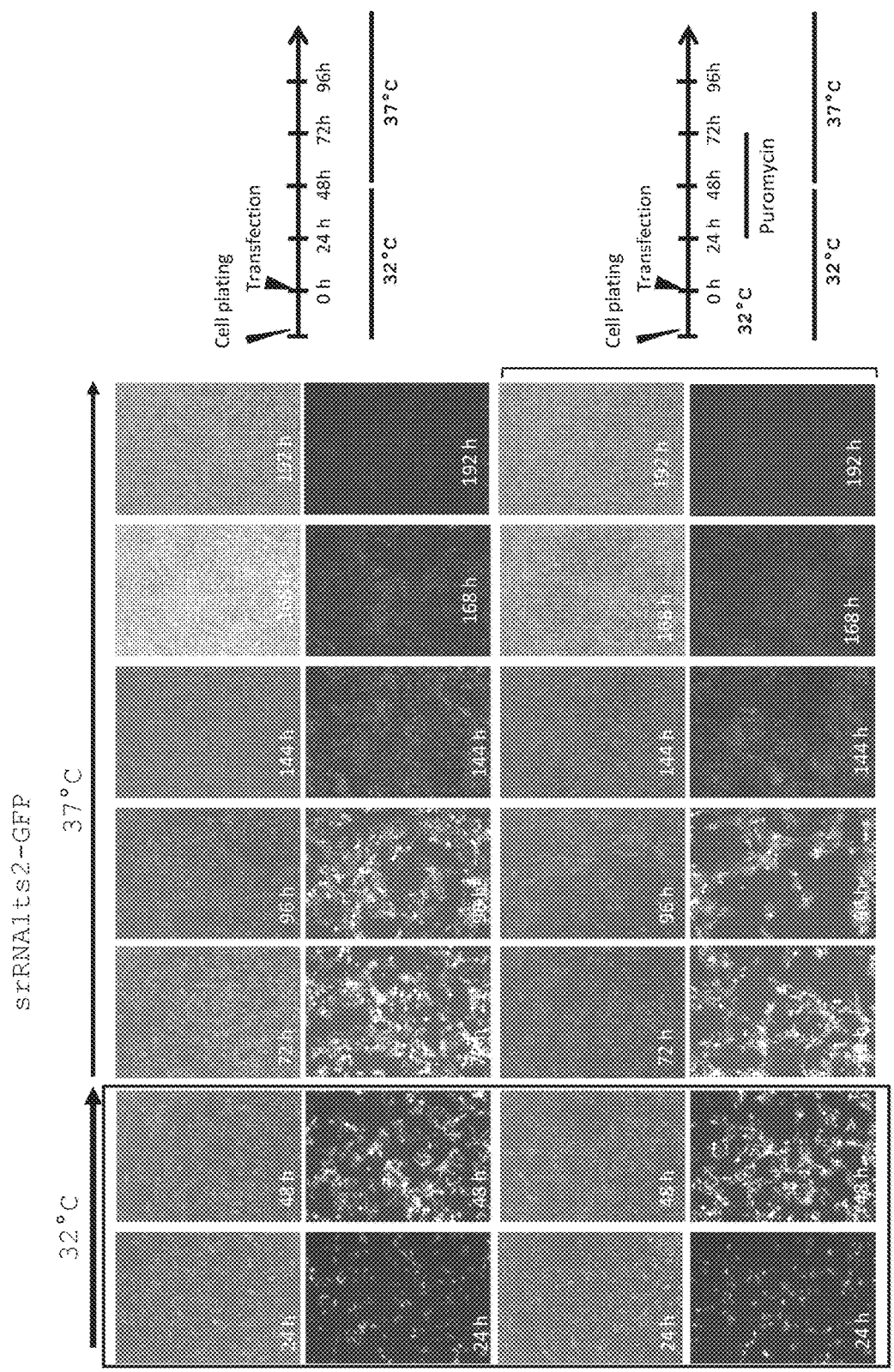
FIG. 9 depicts testing temperature-sensitivity of mutant srRNA1ts2-GFP with a temperature switch from 32° C. to 37° C. at 48 hours. RNAs produced by in vitro transcription of a mutant vector (srRNA1ts2-GFP) were transfected into human induced pluripotent stem cells (ADSC-iPSC line). Cells were cultured in $CO_2$ incubators maintained at 32° C. At 48 hours, cells were transferred to $CO_2$ incubator maintained at 37° C. The srRNA1ts2-GFP vector contains a puromycin N-acetyltransferase (pac) selection gene inserted after the "IRES" sequence, and thus, transfected cells can be selected using puromycin. The experiments were done in the absence (upper panel) or presence (lower panel) of 1 µg/ml of puromycin. Pictures of cells were obtained at 24, 48, 96, 144, 168, 192 hours. The upper panels show phase-contrast images and the lower panels show fluorescence images detecting expression of GFP.

FIG. 9 shows the results. At 32° C., the GFP expression from srRNA1ts2-GFP started as early as 24 hours and further increased at 48 hours. The expression of GFP continued until 96 hours even after the switching of temperature to 37° C. at 48 hours. But the GFP expression started to decrease from 72 hours and by 96 hours the GFP expression became very weak. By 144 hours the GFP expression was barely detected and completely turned off by 192 hours. Thus, the expression of the GOI (represented here by GFP) was rapidly turned off, when the temperature shifted from 33° C. (a permissive temperature) to 37° C. (a non-permissive temperature). The expression pattern of GFP did not seem to be altered by the addition of puromycin.

Assessing Temperature-Sensitivity of srRNA1ts2-GFP Switched from 32° C. to 37° C. after 72 Hours.

ADSC-iPSC cells were plated on a 24-well plate at the density of 80,000 cells/well. After 24 hours, cells were transfected with srRNA 1ts2-GFP. For transfection, each well of a 24-well plate was treated with, 0.5 μg synthetic RNA (srRNA) mixed with 1 μl of JetMessenger (Polyplus) transfection reagent at a final volume of 50 μl. After adding the transfection complex to the cells, 450 μl of culture media was added. The cells were incubated at 32° C. At 6 hours after transfection, the medium was changed to remove the transfection complex. The medium was changed every day. The srRNA1ts2-GFP vector contains a puromycin N-acetyl-transferase (pac) selection gene inserted after the "IRES" sequence, and thus, can be selected using puromycin. The experiments were done in the absence (upper panel) or presence (lower panel) of 1 μg/ml of puromycin. For the cells with puromycin selection, puromycin was added at 48 hours and 72 hours. To test the effects of temperature shift, the cell cultures were transferred to a $CO_2$ incubator maintained at 37° C. at 72 hours (72 hours after the transfection). The phase-contrast and fluorescent images were taken at 24, 48, 72, 96, 144, 168, 192 hours.

Figure 10:
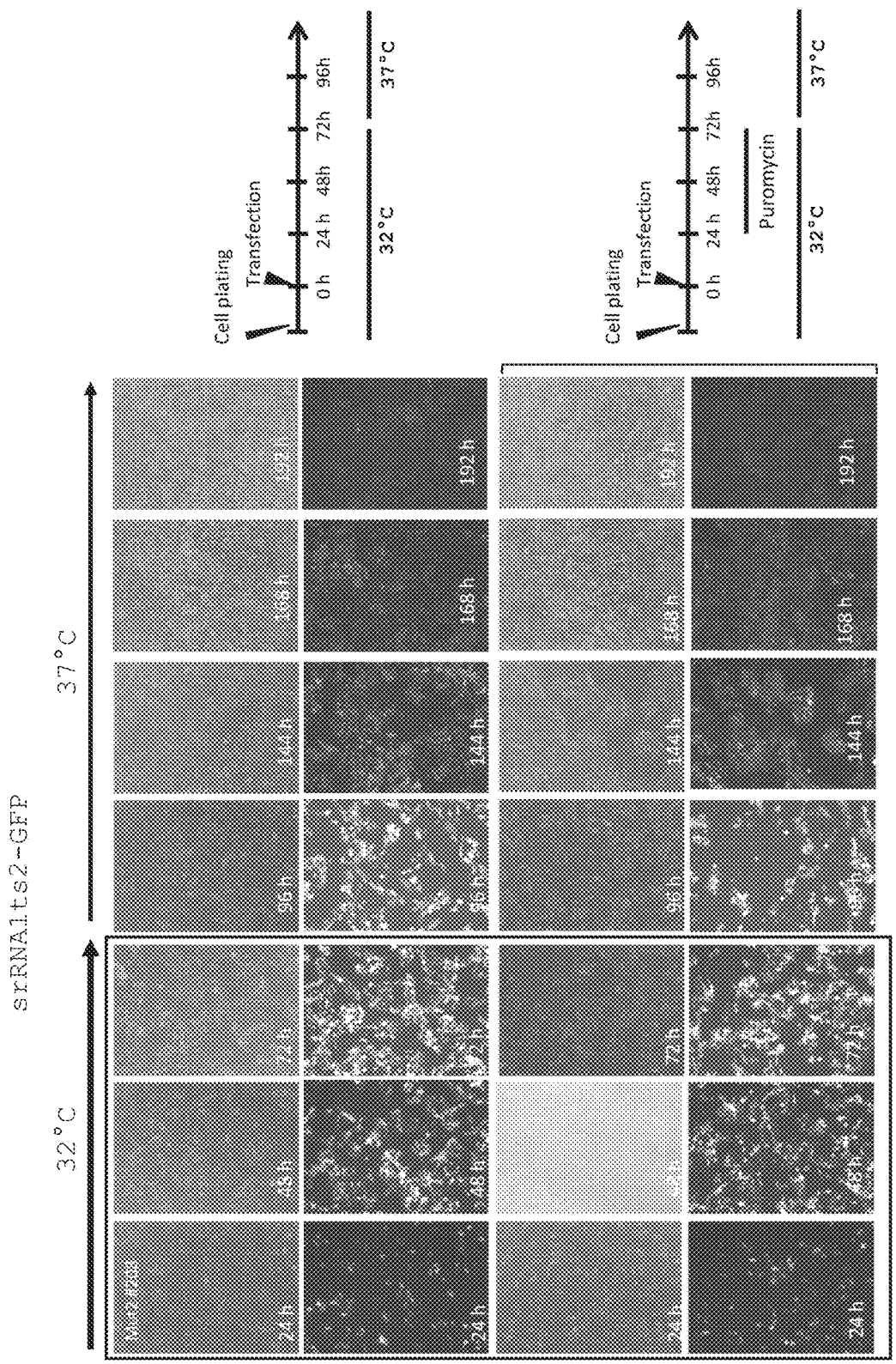
FIG. 10 depicts testing temperature-sensitivity of mutant srRNA1ts2-GFP with a temperature switch from 32° C. to 37° C. at 72 hours. RNAs produced by in vitro transcription of a mutant vector (srRNA1ts2-GFP) were transfected into human induced pluripotent stem cells (ADSC-iPSC line). Cells were cultured in $CO_2$ incubators maintained at 32° C. At 72 hours, cells were transferred to a $CO_2$ incubator maintained at 37° C. The srRNA1ts2-GFP vector contains a puromycin N-acetyltransferase (pac) selection gene inserted after the "IRES" sequence, and thus, transfected cells can be selected using puromycin. The experiments were done in the absence (upper panel) or presence (lower panel) of 1 µg/ml of puromycin. Pictures of cells were obtained at 24, 48, 96, 144, 168, 192 hours. The upper panels show phase-contrast images and the lower panels show fluorescence images detecting expression of GFP.
Figure 11C:
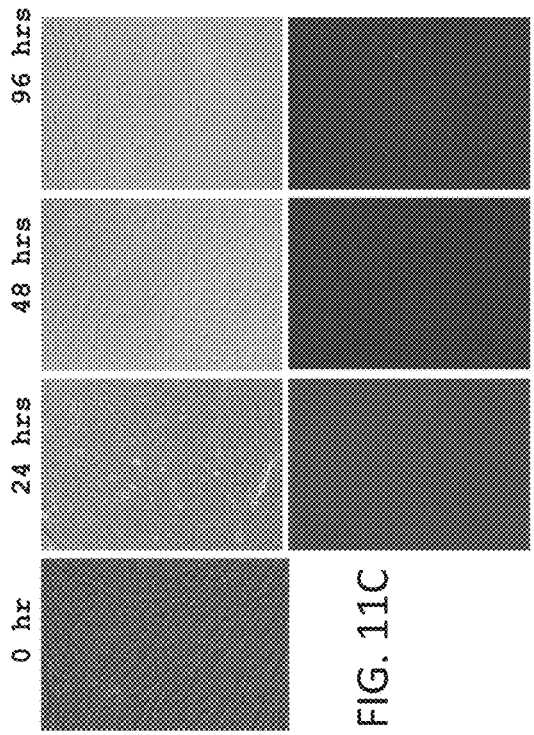
FIGS. 11A-11D depict testing temperature-sensitivity of mutant srRNA1ts2-GFP in fibroblast cells. RNAs produced by in vitro transcription of a mutant vector (srRNA1ts2-GFP) were transfected into human newborn dermal fibroblast cells (HDFn line). Cells were cultured in $CO_2$ incubators maintained at 32° C. Pictures of cells were obtained at 24, 48, and 96 hours. The upper panels show phase-contrast images and the lower panels show fluorescence images detecting expression of GFP.
Figure 11D:
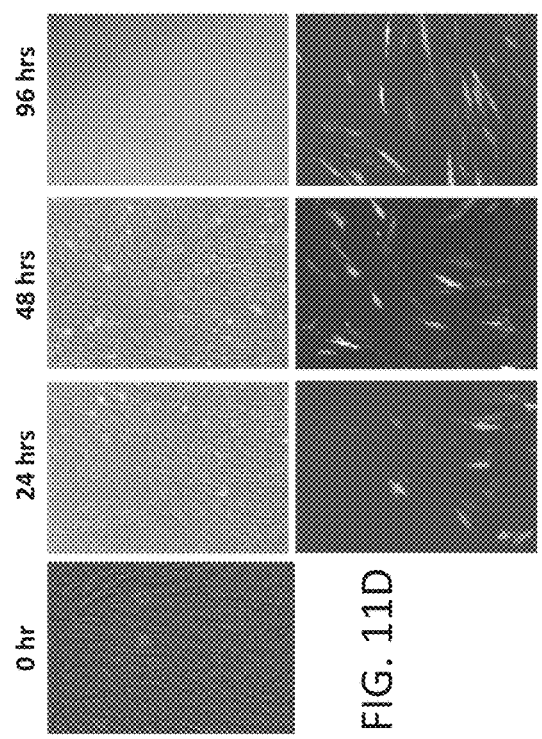
Figure 11A:
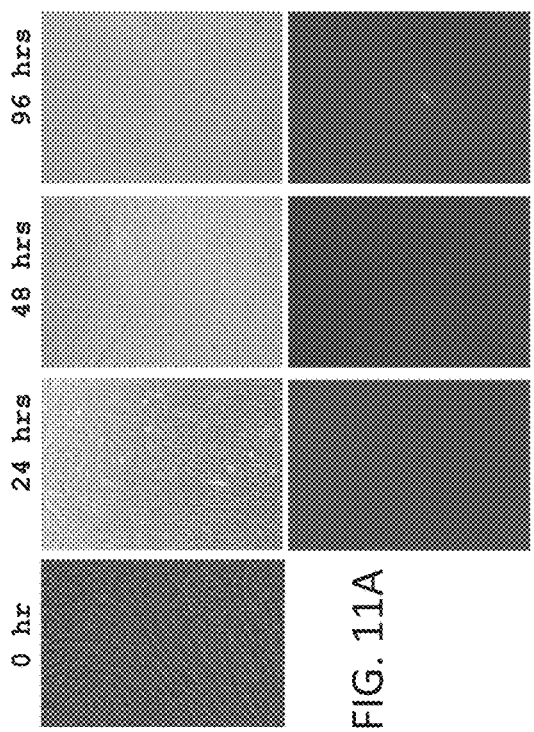
Figure 11B:
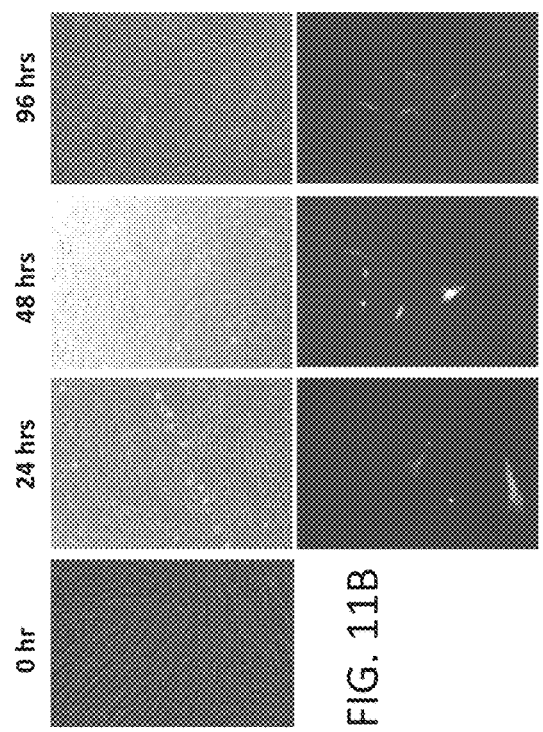

FIG. 10 shows the results. At 32° C., the GFP expression from srRNA1ts2-GFP started as early as 24 hours and further increased at 48 hours. The expression of GFP continued until 96 hours even after the switching of temperature to 37° C. at 48 hours. But the GFP expression started to decrease from 72 hours and by 144 hours the GFP expression became very weak. By 168 hours the GFP expression was barely detected and completely turned off by 192 hours. Thus, the expression of the GOI (represented here by GFP) was rapidly turned off, when the temperature shifted from 33° C. (a permissive temperature) to 37° C. (a non-permissive temperature). The expression pattern of GFP did not seem to be altered by the addition of puromycin.

Assessing Temperature-Sensitivity of srRNA1ts2-GFP in Fibroblast Cells

Human newborn dermal fibroblast cells (HDFn at passage 20) were plated on a 24-well plate at the density of 10,000 cells/well. After 24 hours, cells were transfected with srRNA1wt-GFP. Transfection of srRNA1wt-GFP (0.5 μg synthetic RNA) was carried out by using either JetMessenger (Polyplus) transfection reagent or Lipofectamine MessengerMax (Thermo-Fisher). The cells were incubated at 37° C. To see the effect of B18R, which is known to repress interferon responses, the transfection and cell culture were carried out in the absence (upper panel) or presence (lower panel) of 200 ng/ml B18R. The medium was changed every day. The phase-contrast and fluorescent images were taken at 0, 24, 48, and 96 hours.

FIG. 11 shows the results. In the absence of B18R, almost no expression of GFP was detected. By contrast, in the presence of B18R, the GFP expression from srRNA1 wt-GFP started as early as 24 hours and continued until 48 hours and 72 hours. The expression of GFP was strong in the GFP+ cells, but the frequency of GFP+ cells was not high. This was most likely due to the low transfection efficiency of srRNA1 wt-GFP on human primary fibroblast cells.

Aligning Amino Acid Sequences of Alphavirus Family Corresponding to Mutant 2 (Ts2)

As shown in FIG. 12, the structure of nsP2 proteins of Alphavirus, even at the amino acid level, is well conserved among family members. Based on the 3D structural model (Russo et al., 2006), the protein region, where the 5 amino acids SEQ ID NO:39 (TGAAA) are inserted in the mutant 2, is a turning point between two beta-sheet structures, which is also well conserved among Alphavirus family members. Therefore, it is highly likely that the temperature-sensitivity of mutant 2 is transferable to other Alphavirus family members, including Aura (Aura virus), WEEV (Western equine encephalitis virus), BFV (Barmah Forest virus), ONNV (O'nyong-nyong virus), RRV (Ross River virus), SFV (Semliki Forest virus), and SINV (Sindbis virus). Suitable locations for insertions in nsP2 of various Alphaviruses for conferring temperature-sensitivity are listed in Table 3-1.

TABLE 3-1

Alphavirus nsP2 Sequences and Insertion Sites

| Alphavirus | NCBI Accession No. | Insertion Site (:) amino acids positions |
|---|---|---|
| Venezuelan equine encephalitis virus | NP_740697 | 586:587 |
| Aura virus | NP_819011 | 596:597 |
| Western equine encephalitis virus | CAA52868 | 683:684 |
| Barmah Forest virus | NP_818996 | 588:589 |
| Onyong-nyong virus | AAC97204 | 1123:1124 |
| Ross River virus | NP_740679 | 587:588 |
| Semliki Forest virus | NP_463457 | 1125:1126 |
| Sindbis virus | AF492770_1 | 1137:1138 |

Example 4: Temperature-Sensitive Antibodies

This example describes temperature-sensitive antibodies. An antibody that functions at a permissive temperature (e.g., 32° C.) and does not function or shows reduced function at a non-permissive temperature (e.g., 37° C.) is engineered by insertion or substitution of amino acid sequences. A temperature-sensitive antibody can be produced by inserting a linker oligonucleotide encoding the temperature-sensitive helix-coil transition peptide (-Glu-Ala-Ala-Ala-Lys-, set forth as SEQ ID NO:37), as described (Kamihara and Iijima, 2000; Merutka and Stellwagen, 1990). In this way, an engineered antibody can be produced, which functions at a permissive temperature (e.g. 32° C.), but does not function at a non-permissive temperature (e.g., 37° C.). Alternatively, the antibody DNA sequence of animals naturally living in a low temperature environment (e.g., Atlantic salmon and shrimp) can be used, as these antibodies are optimally functioning at a permissive temperature (at low temperature), but show reduced functionality at a non-permissive temperature (e.g., 37° C.).

Example 5: Temperature-Sensitive Proteins

This example describes temperature-sensitive proteins. Such proteins function at a permissive temperature (e.g., 32° C.) and do not function or show low function at a non-permissive temperature (e.g., 37° C.). Temperature-sensitive proteins are engineered by substituting amino acid sequences. Alternatively, temperature-sensitive proteins obtained from animals naturally living in a low temperature environment (e.g., Atlantic salmon and shrimp) can be used, as these proteins are optimally functioning at a permissive temperature (at low temperature), but show reduced functionality at a non-permissive temperature (e.g., 37° C.) (e.g., shrimp alkaline phosphatase).

Example 6: Temperature-Sensitive RNAs

This example describes temperature-sensitive RNA molecules. RNA molecules include, but are not limited to, mRNA, a precursor of mRNA, non-coding RNA, siRNA, and shRNA. Temperature-sensitive RNAs function at a permissive temperature (e.g., 32° C.) and do not function or show low function at a non-permissive temperature (e.g., 37° C.). Temperature-sensitive RNAs are engineered by systematically changing the nucleotides of RNA molecules to less thermo-stable variants (e.g., G→A), while ensuring that the functional properties of the RNAs are maintained. Further, the difference in thermostability of the nucleotide pairs, induced by a shift in temperature, changes the secondary structure of the RNAs.

Example 7: Ex Vivo Treatment of Cells with Temperature-Sensitive Agents

Figure 13:
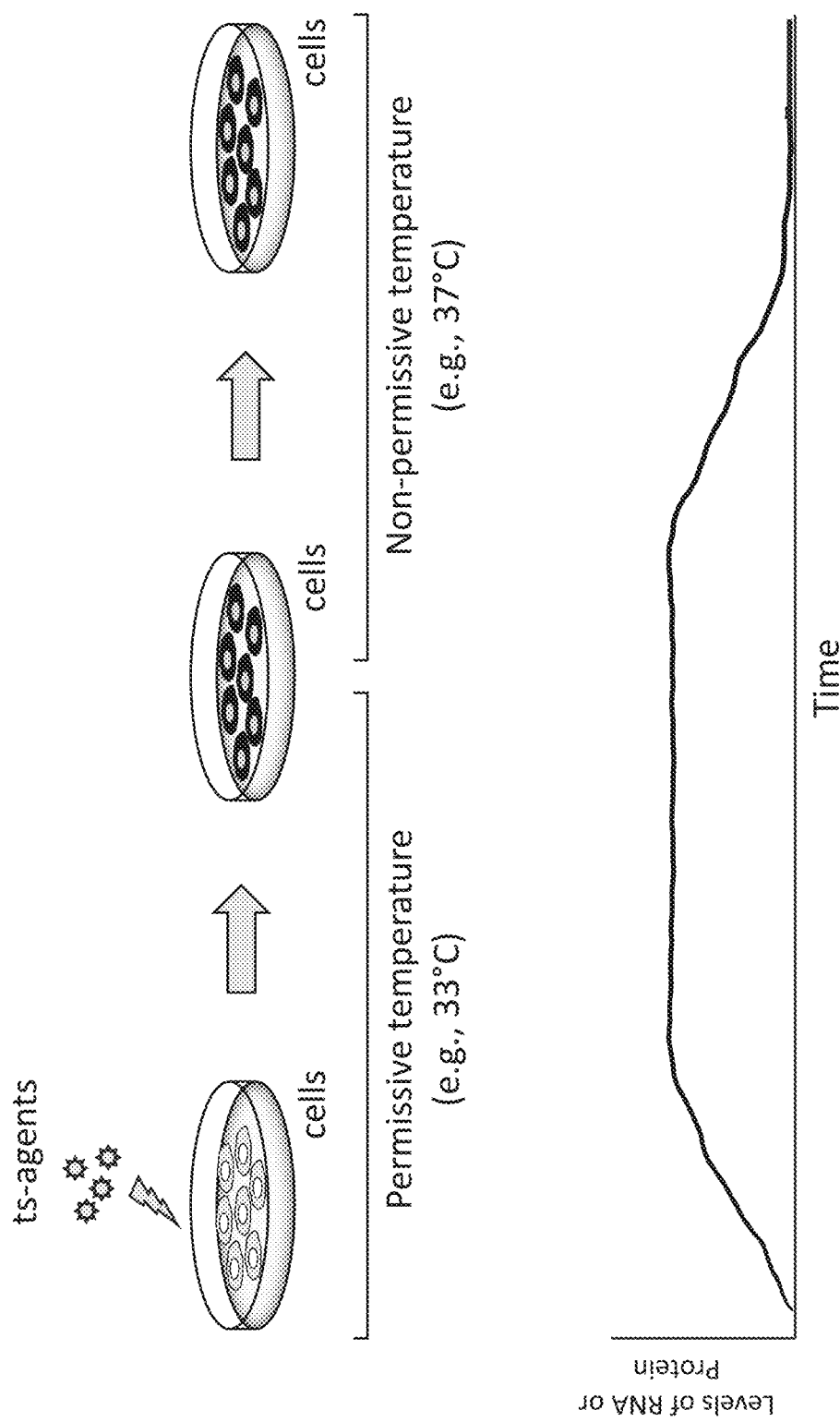
FIG. 13 depicts a schematic diagram showing a typical ex vivo treatment of cells with temperature-sensitive agents (ts-agents). Ts-agents such as srRNAs or Sendai virus vectors, are functional at a permissive temperature (e.g., 33° C.), but non-functional at a non-permissive temperature (e.g., 37° C.). Target cells treated with the ts-agent are cultured at a permissive temperature for a certain duration (e.g., 3 days), and then continue to be cultured at a non-permissive temperature for a certain duration (e.g., 10 days). Expected levels of RNA (or protein translated from the RNA) of a gene of interest (GOI) increase at a permissive temperature and reach a high level. After switching to a non-permissive temperature, expected levels of RNA (or proteins) gradually decrease as transcription and translation cease.

This example demonstrates a method for transiently delivering an RNA or protein to cells ex vivo (FIG. 13). A temperature-sensitive therapeutic agent can be any of the temperature-sensitive therapeutic agents disclosed herein. Ts-agents such as srRNAs or Sendai virus vector are functional at a permissive temperature (e.g., 33° C.), but non-functional at a non-permissive temperature (e.g., 37° C.). Target cells treated with the ts-agent are cultured ex vivo at a permissive temperature for a certain duration (e.g., 3 days), and then are cultured at a non-permissive temperature for a certain duration (e.g., 10 days). Levels of RNAs (or proteins translated from the RNAs) of a GOI increase at a permissive temperature and reach a high level. After switching to a non-permissive temperature, expected levels of RNAs gradually decrease and subsequently reach to a non-expression level (FIG. 13).

Example 8: Ex Vivo Therapeutic Use of Temperature-Sensitive Agents

Figure 14:
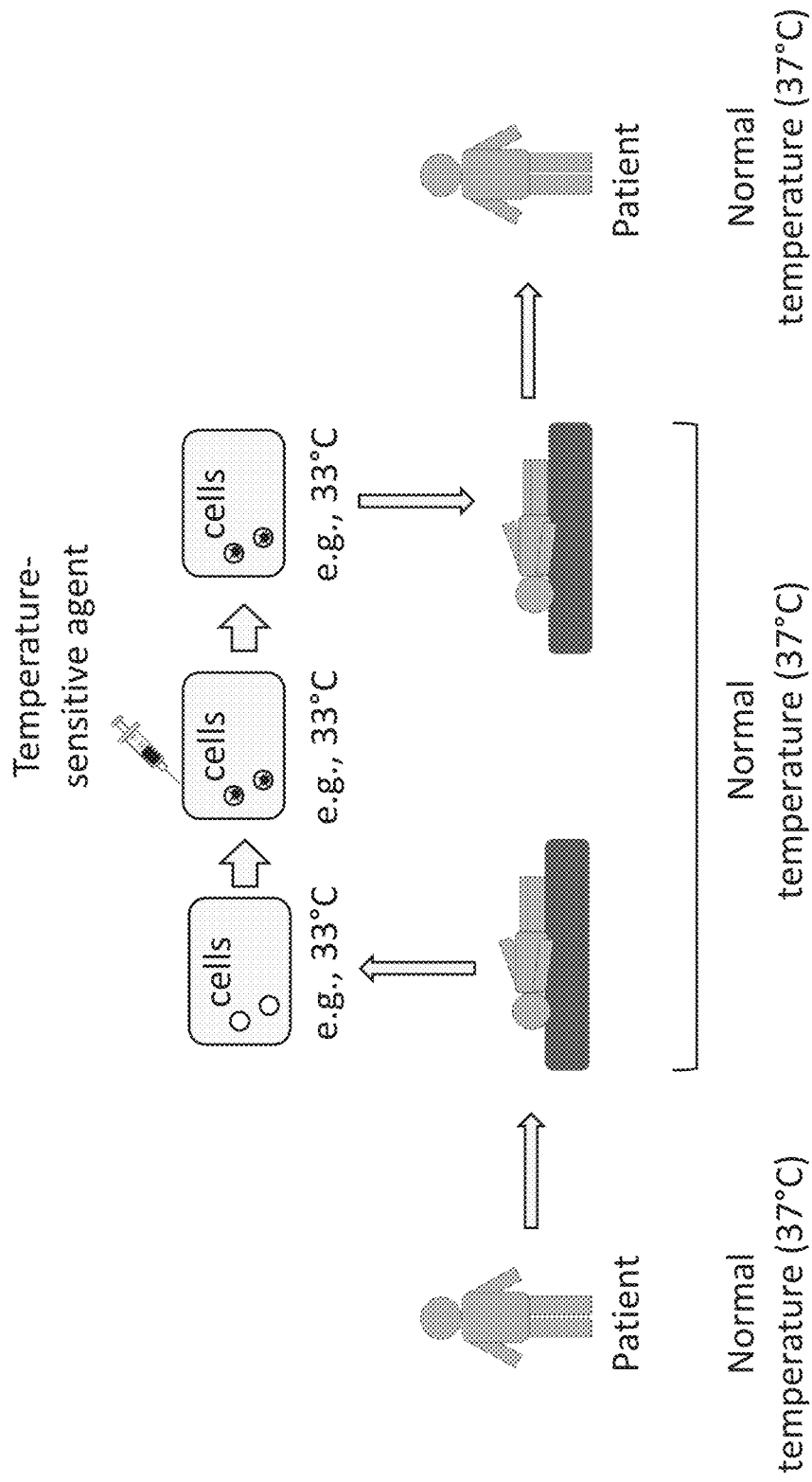
FIG. 14 depicts a schematic diagram showing an exemplary ex vivo therapeutic procedure. Temperature-sensitive agents (ts-agents) such as srRNAs or Sendai virus vectors, are functional at a permissive temperature (e.g., 33° C.), but non-functional at a non-permissive temperature (e.g., 37° C.). Target cells are taken from a patient's body (autograft) and are incubated with the ts-agent ex vivo at a permissive temperature, e.g., at 33° C., for a certain duration, e.g., 24 hours. Then, the target cells with ts-agents are transplanted in the patient. At a non-permissive temperature of 37° C., the ts-agent does not function inside the patient's body.
Figure 15:
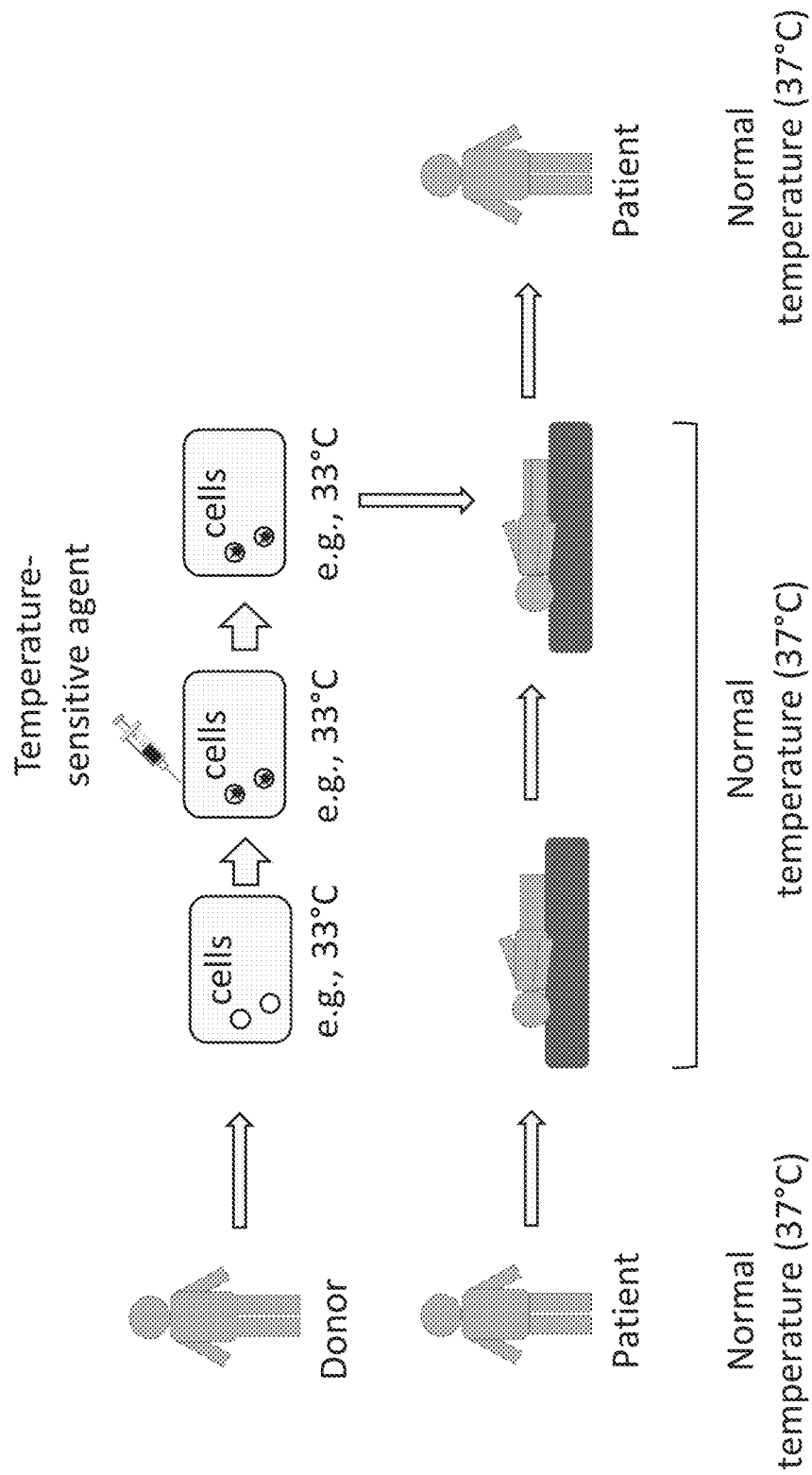
FIG. 15 depicts a schematic diagram showing another exemplary ex vivo therapeutic procedure. Temperature-sensitive agents (ts-agents) such as srRNAs or Sendai virus vectors, are functional at a permissive temperature (e.g., 33° C.), but non-functional at a non-permissive temperature (e.g., 37° C.). Target cells are taken from a donor's body (allograft) and are incubated with the ts-agent ex vivo at a permissive temperature, e.g., at 33° C., for a certain duration, e.g., 24 hours. Then, the target cells with ts-agents are transplanted in a patient. At a non-permissive temperature of 37° C., the ts-agent does not function inside the patient's body.

This example demonstrates a method for transiently delivering an RNA or protein to cells ex vivo (FIG. 14 and FIG. 15). Ts-agents such as srRNAs or Sendai virus vector are functional at a permissive temperature (e.g., 33° C.), but non-functional at a non-permissive temperature (e.g., 37° C.: a human body temperature). Typically, target cells are taken from a patient (autologous cell transplants; FIG. 14), but it is also possible to use target cells isolated from a donor (allogenic cell transplant; FIG. 15). For instance, the target cells may be isolated by using antibody-conjugated magnetic beads. Target cells are incubated with the ts-agent ex vivo at a permissive temperature, e.g., at 33° C. for a certain duration, e.g., 24 hours. Levels of RNAs (or proteins translated from the RNAs) of a GOI increase at a permissive temperature reach a high level. After the therapeutic effect is induced, the cells are transplanted back to the patient in order to treat the patient. The activity of the temperature-sensitive therapeutic agent is not induced at the subject's normal body temperature (i.e. normal body temperature is a non-permissive temperature). The degradation of the temperature-sensitive therapeutic agent begins after the therapeutic effect is induced, and eventually the temperature-sensitive therapeutic agent is completely degraded. The body temperature is maintained at or above 37° C. for the lifetime of the patient, and thus, the ts-agent is not reactivated and cells other than the target cells will not be treated with the ts-agent.

Mobilized Human Peripheral Blood Cells

Human blood cells isolated from a patient's, or donor's, bone marrow or peripheral blood are treated with ts-agents ex vivo at a permissive temperature. After injection of G-CSF or other mobilizing agents, human white blood cells are collected from peripheral blood by an apheresis machine (e.g., COBE Spectra). The white blood cells collected after mobilization from bone marrow contain granulocytes, monocytes, lymphocytes, dendritic cells, mesenchymal stem cells (MSCs), vascular endothelial cells (VECs), and CD34+ hematopoietic/progenitor cells. The treatment of these cells with ts-agents is conducted ex vivo, ideally, using a functionally closed system such as Miltenyi's CliniMacs Prodigy, at a functional temperature (e.g., 33° C.) for a certain duration (a few hours to a few weeks). Subsequently, the treated cells are infused into patients at a non-permissive temperature (37° C.). The ts-agents, cells containing the ts-agents, or the product of ts-agents do not function in the patient's body.

Human CD34+ Hematopoietic Stem/Progenitor Cells

Human CD34+ hematopoietic stem/progenitor cells are isolated from the mobilized human peripheral blood cells or bone marrow cells by antibody (against CD34)-conjugated magnetic beads and used as target cells are treated with ts-agents ex vivo at a permissive temperature. After treatment with a ts-agent, human CD34+ cells are infused into a patient's body and engraft in the patient's bone marrow. These cells will eventually produce all the blood cells in the patient's body, and thus, are a suitable target for a variety of diseases.

Any Human Cells Including Tissue Stem Cells

Any human cells isolated from patient or donor and used as target cells are treated with ts-agents ex vivo at a permissive temperature. Such cells include but are not limited to skin fibroblast cells, follicular cells, skeletal muscle cells, hepatocytes, and neural tissues. Such cells also include a variety of tissue stem cells such as mesenchymal stem cells, neural stem cells, muscle stem cells, skin stem cells, and intestinal stem cells.

Example 9: Semi In Vivo Therapeutic Use of Temperature-Sensitive Agents

Figure 16:
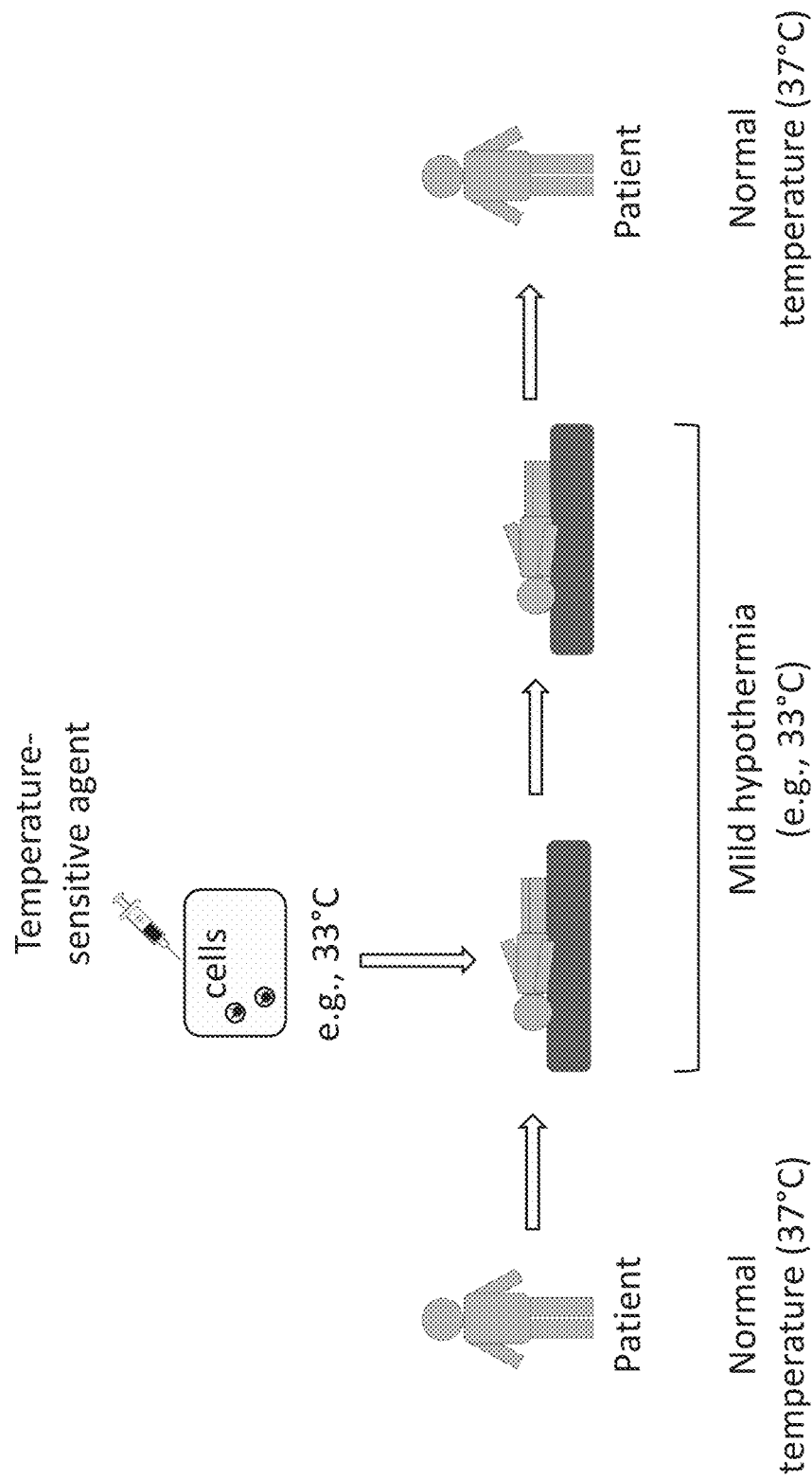
FIG. 16 depicts a schematic diagram showing an exemplary semi in vivo therapeutic procedure. Temperature-sensitive agents (ts-agents) such as srRNAs or Sendai virus vectors, are functional at a permissive temperature (e.g., 33° C.), but non-functional at a non-permissive temperature (e.g., 37° C.). A patient undergoes a procedure for therapeutic hypothermia and the patient's core body temperature is maintained at a reduced temperature (e.g., 33° C.), which is lower than normal body temperature (e.g., 37° C.). Target cells (either autologous or allogenic) are treated with the ts-agent ex vivo and immediately infused into the patient's circulation or injected into an organ of the patient. While the patient is maintained at the reduced temperature (e.g., 33°

This example describes a semi in vivo method for transiently delivering an RNA or protein to cells (FIG. 16). A temperature-sensitive therapeutic agent can be any of the temperature-sensitive therapeutic agents disclosed herein. A ts-agent is functional at a permissive temperature (e.g., 33° C.), but non-functional at a non-permissive temperature (e.g., 37° C.).

A patient undergoes a procedure for therapeutic hypothermia: the patient's core body temperature is maintained at a temperature lower than normal body temperature (e.g., 33° C.). Target cells (any cells—autologous or allogenic) are treated by the ts-agent ex vivo and immediately infused into the patient's circulation or injected into the patient's organs.

While the patient is maintained at the targeted temperature, e.g., 33° C. for some time, e.g., 24 hours, the ts-agent exhibits their expected functions. Levels of RNAs (or proteins translated from the RNAs) of a GOI increase at a permissive temperature reach a high level. Subsequently, the patient's body temperature is returned to normal temperature at 37° C. The ts-agent no longer functions at the non-permissive condition, 37° C. inside the patient's body. The body temperature is maintained at or above 37° C. for the lifetime of the patient, and thus, the ts-agent is not reactivated and cells other than the target cells will not be treated with the ts-agent. Notably, this therapeutic procedure can be applied to any cell type including those described above.

Example 10: In Vivo Therapeutic Use of Temperature-Sensitive Agents

This example demonstrates how a temperature-sensitive viral vector is administered to a subject and transiently activated when mild hypothermia is induced in the subject (FIG. 17). A temperature-sensitive therapeutic agent can be any of the temperature-sensitive therapeutic agents disclosed herein. Temperature-sensitive therapeutic agents are functional at a permissive temperature (e.g., 33° C.), but non-functional at a non-permissive temperature (e.g., 37° C.: a human body temperature).

The subject's body temperature is lowered using a target-temperature management (TTM) procedure, which has been used in the clinic for patients with heart and brain trauma (Callaway et al., 2015). A TTM procedure is designed to achieve and maintain a specific body temperature in a subject for a duration of time. Such procedures have previously been used therapeutically to reduce the negative effects resulting from various acute health issues such as heart attacks and strokes. Equipment and general methods of using a TTM procedure are known in the art and can be used with the methods described herein. The TTM procedure can be carried out using a number of methods, including cooling catheters, cooling blankets, and application of ice around the body. A variety of instruments have been used for such purposes. For example, the ArcticSun™ is an instrument that can be used to decrease or increase a patient's body temperature to between 32° C.-38.5° C. (Pittl et al., 2013). The procedure can be performed safely and it has been reported that there are no major adverse effects that are caused by this instrument.

A patient is placed under hypothermic conditions using the TTM procedure, and the target body temperature is one sufficient to induce an activity of the temperature-sensitive therapeutic agent. The temperature-sensitive therapeutic agent is delivered directly to the patient through either the systemic route (e.g., intravenously) or through direct injection into organs/tissues (e.g., catheter, or percutaneous needle injection) (FIG. 17).

The patient's temperature is kept at the permissive temperature for a time sufficient to allow induction of a desired activity of the temperature-sensitive therapeutic agent. The desired activity of the temperature-sensitive agent leads to a therapeutic effect in the cells containing or exposed to the temperature-sensitive therapeutic agent.

After the desired therapeutic effect is achieved, the patient's body temperature is then returned to a normal body temperature (i.e., a non-permissive temperature) causing the activity of the temperature-sensitive therapeutic agent to cease. This is followed by degradation of temperature-sensitive therapeutic agent.

Systemic Delivery Through Circulation

A patient is placed under hypothermic conditions (e.g., at 33° C.). Once the patient's core body temperature is maintained at the target temperature stably, a ts-agent is delivered directly to the patient intravenously. The ts-agent is delivered to many organs and tissues through this systemic route. The core body temperature of the patient is maintained at the functional temperature for a desired duration (e.g., 24 hours). While the patient's body temperature is kept at a permissive temperature for the agent (e.g., at 33° C.), the agent is functioning. When the patient's body temperature is returned to normal at 37° C., which is a non-permissive temperature of the agent, the agent stops working.

The ts-agent may be a naked RNA (i.e., a synthetic RNA). Systemic delivery through circulation delivers a naked RNA to many organs with or without the target organ specificity. Alternatively, the ts-agent is an RNA (i.e., a synthetic RNA) encapsulated by nanoparticles, which are engineered to target specific cell types, tissues, organs, cancers, tumors, or abnormal cells. Thus, systemic delivery through circulation delivers a nanoparticle-encapsulated RNA to specific cell types, tissues, organs, cancers, tumors, or abnormal cells. Alternatively, the ts-agent is an RNA packaged into a viral particle. Depending on the envelope types and other features, a virus particle targets specific cell types, tissues, organs, cancers, tumors, or abnormal cells. Thus, systemic delivery through circulation delivers an RNA packaged into a viral particle to specific cell types, tissues, organs, cancers, tumors, or abnormal cells. Alternatively, ts-agent is a temperature-sensitive virus vector. Depending on the envelope types and other features, a virus particle targets specific cell types, tissues, organs, cancers, tumors, or abnormal cells. Thus, systemic delivery through circulation delivers a temperature-sensitive virus vector to specific cell types, tissues, organs, cancers, tumors, or abnormal cells.

Targeting Delivery to the Brain and Spinal Cord Through Cerebrospinal Fluid

A patient is placed under hypothermic conditions (e.g., at 33° C.). Once the patient's core body temperature is maintained at the target temperature stably, a ts-agent is delivered directly to the patient's cerebrospinal fluids by an epidural injection. The ts-agent is delivered to the brain and spinal cord. The core body temperature of the patient continues to be maintained at the permissive temperature for the desired duration (e.g., 24 hours). While the patient's body temperature is kept at a permissive temperature for the agent (e.g., at 33° C.), the agent is functioning. When the patient's body temperature is returned to normal at 37° C., which is a non-permissive temperature of the agent, the agent stops working.

Targeting Delivery to Liver, Kidney, Skeletal Muscles, Cardiac Muscles, Pancreas, Bone Marrow, and Other Organs Through Percutaneous Injection A patient is placed under hypothermic conditions (e.g., at 33° C.). Once the patient's core body temperature is maintained at the target temperature stably, a ts-agent is injected through the skin (percutaneously) into organs such as the liver, kidney, skeletal muscles, cardiac muscles, pancreas, or other organs using a very thin needle with the visual guidance of ultrasound or CT. The core body temperature of the patient is maintained at the permissive temperature for the desired duration (e.g., 24 hours). While the patient's body temperature is kept at the permissive temperature for the agent (e.g., at 33° C.), the agent is functioning. When the patient's body temperature is returned to normal at 37° C., which is a non-permissive temperature of the agent, the agent stops working.

Targeting Delivery to Liver, Kidney, Skeletal Muscles, Cardiac Muscles, Pancreas, Bone Marrow, and Other Organs Through Endoscopy with Injection Needle Catheter A patient is placed under hypothermic conditions (e.g., at 33° C.). Once the patient's core body temperature is maintained at the target temperature stably, then a ts-agent is delivered directly to specific organs and tissues through endoscopic injection needle catheter. The core body temperature of the patient is maintained at the permissive temperature for the desired duration (e.g., 24 hours). While the patient's body temperature is kept at a permissive temperature for the agent (e.g., at 33° C.), the agent is functioning. When the patient's body temperature is returned to normal at 37° C., which is a non-permissive temperature of the agent, the agent stops working.

Targeting Delivery to Liver, Kidney, Skeletal Muscles, Cardiac Muscles, Pancreas, Bone Marrow, and Other Organs Through Angiocatheter A patient is placed under hypothermic conditions (e.g., at 33° C.). Once the patient's core body temperature is maintained at the target temperature stably, then a ts-agent is delivered directly to specific organs and tissues through angiocatheter. The core body temperature of the patient is maintained at a permissive temperature for the desired duration (e.g., 24 hours). While the patient's body temperature is kept at a permissive temperature for the agent (e.g., at 33° C.), the agent is functioning. When the patient's body temperature is returned to normal at 37° C., which is a non-functional temperature of the agent, the agent stops working.

Targeting Delivery to Lung and Other Organs Through Inhalation

A patient is placed under hypothermic conditions (e.g., at 33° C.). Once the patient's core body temperature is maintained at the target temperature stably, then a ts-agent is delivered directly to the patient by inhalation. The ts-agent is delivered to lungs and other organs through via inhalation through the lungs. The core body temperature of the patient is maintained at a permissive temperature for the desired duration (e.g., 24 hours). While the patient's temperature is kept at a permissive temperature for the agent (e.g., at 33° C.), the agent is functioning. When the patient's body temperature is returned to normal at 37° C., which is a non-permissive temperature of the agent, the agent stops working.

Targeting Delivery to Bone Marrow Cells Mobilized to Spleen

A patient will receive an injection of G-CSF, plerixafor or other cytokines to mobilize bone marrow cells (including, without limitation, CD34+ cells, hematopoietic stem cells, mesenchymal stem cells, and endothelial stem cells) to the spleen of the subject. The patient is placed under hypothermic conditions (e.g., at 33° C.). Once the patient's core body temperature is maintained at the target temperature stably, then a ts-agent is delivered to the spleen via the methods described above. Subsequently, the ts-agent is delivered to bone marrow cells mobilized to the spleen. The core body temperature of the patient is maintained at a permissive temperature for the desired duration (e.g., 24 hours). While the patient's temperature is kept at a permissive temperature for the agent (e.g., at 33° C.), the agent is functioning. When the patient's body temperature is returned to normal temperature at 37° C., which is a non-permissive temperature for the agent, the agent stops working. For instance, the methods may include administering a therapeutically effective amount of a temperature-sensitive agent (e.g., a temperature-sensitive therapeutic agent) to one or more bone marrow cells (including, without limitation, CD34+ cells, hematopoietic stem cells, mesenchymal stem cells, endothelial stem cells) in the spleen.

Example 11: Differentiation of Human ES and iPS Cells into Desired Cell Types by Self-Replicating RNAs as Temperature-Sensitive Agents This example describes the finding that a temperature-sensitive self-replicating RNA expressing human transcription factors can differentiate hPSCs into a variety of differentiated cells. The finding presented in this example may be applied to the "ex vivo treatment of cells with ts-agents." Differentiated cells generated by this method have many useful applications, such as in vitro modeling of human diseases by using patients-derived iPS cells and drug screening. The findings presented in this example may be applied to "ex vivo therapeutic use of ts-agents." Differentiated cells generated in this method can be transplanted to repair defective organs and tissues in patients. For example, neurons (more specifically dopaminergic neurons) generated ex vivo by this method are transplanted to patient's substantia nigra (a part of brain) to treat Parkinson's disease. The findings presented in this example may be applied to "semi in vivo therapeutic use of ts-agents." Cells treated with ts-agents that induce neurons are transplanted into a patient who undergoes therapeutic hypothermia so that the ts-induced cell differentiation occurs in patient's body. Once the differentiated cells appear, ts-agents are turned off by returning patient's body temperature to non-permissive temperature (i.e., 37°). The findings presented in this example may be applied to "in vivo therapeutic use of ts-agents." For example, ts-agents expressing a set of transcription factor are directly injected into a pancreas of Diabetes patient who undergoes therapeutic hypothermia (at a permissive temperature) so that the patient's pancreatic duct cells are converted to insulin-secreting beta-cells in vivo. Once the desired cells appear, ts-agents are turned off by returning patient's body temperature to non-permissive temperature (i.e., 37°).

Materials and Methods

Cell Culture

A human adipose stem cell-derived iPS cell line (ADSC-iPS cells) was purchased from System Biosciences (Palo Alto, Calif.). Cells were routinely maintained as undifferentiated pluripotent cells according to the standard hPSC culture method. Briefly, cells were cultured in StemFit basic02 (Ajinomoto, Japan) supplemented with 100 ng/ml FGF2. Further, cells were cultured on cell culture dishes coated with a laminin-511 substrate (iMatrix-511, Nippi, Japan).

Temperature-Sensitive Self-Replicating RNAs (srRNA1-ts2)

An open reading frame of a gene of interest (GOI) was cloned into srRNA1ts2 vector so that the expression of GOI is controlled in a temperature sensitive manner. Synthetic RNAs were produced by in vitro transcription from the vectors according to Yoshioka et al., 2013 and used for transfection. The following GOI was cloned into the srRNA1ts2 vectors:

srRNA1ts2-NGN3: human neurogenin 3 (NGN3) [NCBI GeneID: 50674]; and srRNA1ts2-ETV2: human ETS Variant 2 (ETV2) [NCBI GeneID: 2116].

Results

Generation of Neurons

ADSC-iPSC cells were plated on a 24-well plate at the density of $1.2 \times 10^5$ cells/well. Before plating the cells, cells were pretreated with Rock inhibitor for 1 hour. 24 hours after the plating, cells were transfected with srRNA 1ts2-NGN3. For transfection, each well of a 24-well plate was treated with, 0.5 µg synthetic RNA (srRNA) mixed with 1 µl of JetMessenger (Polyplus) transfection reagent at a final volume of 50 µl. After adding the transfection complex to the cells, 450 µl of culture media was added. The cells were incubated at 33° C. for 72 hours. The cells were then passaged and cultured on ornithine/laminin-coated glass coverslips. Cells were then cultured at 37° C. The medium was changed every day. The srRNA1ts2-NGN3 vector contains a puromycin N-acetyltransferase (pac) selection gene inserted after the "IRES" sequence, and thus, can be selected using puromycin. After passaging, cells were cultured in the presence of 1 μg/ml of puromycin for 24 hours. The phase-contrast images were taken on day 0, 1, 2, 3, 4, 5 and 6 (FIG. 18). To show the formed neurites more clearly, a magnified picture of the day 6 image is also shown. On day 9, cells were fixed and stained with an antibody against tubulin beta III (TUBB3)—a neural marker. Fluorescence microscopy images of two different magnifications (10×, 40×) are shown (FIG. 18). The results show that the srRNA1ts2-NGN3 can differentiate human iPS cells into neurons rapidly and efficiently.

Generation of Vascular Endothelial Cells

ADSC-iPSC cells were plated on a 24-well plate at the density of 1.2×10=cells/well. Before plating the cells, cells were pretreated with Rock inhibitor for 1 hour. 24 hours after the plating, cells were transfected with srRNA1ts2-ETV2. For transfection, each well of a 24-well plate was treated with, 0.5 μg synthetic RNA (srRNA) mixed with 1 μl of JetMessenger (Polyplus) transfection reagent at a final volume of 50 μl. After adding the transfection complex to the cells, 450 μl of culture media was added. The cells were incubated at 32° C. for 3 days, and then further cultured at 37° C. for 5 more days (8 days total). The medium was changed every day. The srRNA1ts2-ETV2 vector contains a puromycin N-acetyltransferase (pac) selection gene inserted after the "IRES" sequence, and thus, can be selected using puromycin. 1 μg/ml of puromycin was added to the culture at the time of temperature switch from 33° C. to 37° C. The next day, the medium was replaced with media containing 1 μg/ml of puromycin. Therefore, cells were cultured for 2 days in the presence of 1 μg/ml of puromycin. The phase-contrast images were taken on day 1, 2, 3, 4, 5, 6, 7 and 8 (FIG. 19). On day 8, cells were fixed and stained with an antibody against CD31 (a marker for vascular endothelial cells). Fluorescence microscopy images of two different magnifications (10×, 20×) are shown (FIG. 19). The results show that the srRNA1ts2-ETV2 can differentiate human iPS cells into vascular endothelial cells rapidly and efficiently.

Example 12: Genome Editing

Genome editing is a genetic engineering method to alter an organism's genome by replacing, deleting, or adding nucleotide sequences. It has been proposed that genome editing can be used for correcting genome mutations for gene therapy. As a first step, genomic DNA must be cleaved at specific locations by DNA nucleases such as zinc finger nucleases (ZFNs), transcription activator-like effector-based nucleases (TALENs), or the clustered regularly interspaced short palindromic repeat (CRISPR)-CAS9 system. The introduction of these nucleases must be carefully controlled, because the double-stranded DNA breaks introduced by these enzymes are highly deleterious to cells. The targeted expression of these nucleases requires precise control of timing and duration. It has been reported that both guide RNA and CAS9 can be encoded on a single Sendai virus vector, which makes it possible to deliver these components for genome editing of human cells at a high efficiency (Park et al., Molecular Therapy 2016). However, continuous expression of CAS9 could cause introduction of uncontrollable DNA breaks and mutations in human cells. Thus, to use the gene editing system therapeutically, it is desirable to have CAS9 expressed for a short time, on the order of hours, not days. To this end, temperature-sensitive agents can be used as a delivery vehicle of these components, especially the nucleases.

First, the Sendai Virus Vector used for the reported CRISPR/CAS9 system (Park et al., 2016) is replaced by a temperature-sensitive Sendai Viral Vector (SeVts-CAS9-guideRNA). In one embodiment, an SeVts is an SeV18/TS15ΔF (Ban et al., PNAS 2011). Human primary fibroblast cells are infected with the temperature-sensitive Sendai Viral Vector at MOI 25 at 33° C., and are maintained at 33° C. in a $CO_2$ incubator for 24-48 hours. Subsequently, the temperature of the cell culture is shifted to 37° C. for the rest of the cell culture. Viral replication and increased CAS9 expression only occur when the cell culture is maintained at 33° C., and thus, the exposure of the cells to CAS9 nuclease is limited to this short time. While the cells are cultured at 37° C., the temperature-sensitive Sendai Viral Vector is eventually lost from the cells, and thus, there will be no concern about the reactivation of CAS9 expression in vitro and in vivo. Similarly, a temperature-sensitive self-replicating RNA such as srRNA1ts2 (srRNA1ts2-CAS9-guideRNA) could be used in lieu of the SeVts-CAS9-guideRNA.

Example 13: CAR T Cell Therapy

CAR T cell therapy uses a transfer of vector encoding chimeric antigen receptor (CARs) into a patient's own T cells and stably express CARs in cytotoxic T cells (Maus and June 2016). CAR T cell therapy aims to reprogram the patient's own T cells to attack malignant cells in the patient. For example, CAR T cells targeting CD19 have been applied successfully to B-cell malignancies. However, CD19 is also expressed in a normal B cells, and thus, the continuous expression of CARs could incur the side effects, and is not desirable. Therefore, recent clinical trials transfer synthetic mRNAs encoding CARs into a patient's own T cells so that the expression of CARs is transient (ClinicalTrials.gov Identifier: NCT02624258). However, a short turnover time (<12 hours) and a relatively low protein expression levels by synthetic mRNAs present a problem in achieving sufficient expression levels of CARs. To address this issue, ts-agents are used as a delivery vehicle of CARs to T cells.

Ex Vivo Therapeutic Use of Temperature-Sensitive Agents to Deliver CARs to T Cells T cells are collected from peripheral blood using an apheresis machine (COBE Spectra) and a magnetic bead-based enrichment method (Miltenyi's CliniMacs Prodigy). Then, T cells are transfected with srRNA1ts2-CARs and cultured ex vivo at a permissive temperature (33° C.) for 24 hours (or longer). Ideally, this procedure is performed in a functionally closed system such as Miltenyi's CliniMacs Prodigy. Subsequently, the treated cells are infused back into the patient. In the patient's body at a non-permissive temperature (37° C.), srRNA1ts2-CARs stop producing CARs, but sufficient quantities of CARs are already present on the surface of T cells, which exert the expected functions of CARs. Alternatively, a temperature-sensitive Sendai Virus Vector encoding CARs (SeVts-CARs) is used in lieu of the srRNA1ts2-CAR. For instance, the SeVts may be a SeV18/TS15ΔF (Ban et al., PNAS 2011).

Semi In Vivo Therapeutic Use of Temperature-Sensitive Agents to Deliver CARs to T Cells T cells treated with srRNA1ts2-CARs are immediately infused into a patient who is maintained at a permissive temperature (e.g., 33° C.) by therapeutic hypothermia. While maintained a permissive temperature, srRNA1ts2-CARs is functional. However, when the temperature of the patient is switched to a normal temperature (37° C.), srRNA1ts2-CARs stop producing CARs. Alternatively, a temperature-sensitive Sendai Viral Vector encoding CARS (SeVts-CARs) could be used. For instance, the SeVts may be a SeV18/TS15ΔF (Ban et al., PNAS 2011).

In Vivo Therapeutic Use of Temperature-Sensitive Agents to Deliver CARs to T Cells srRNA1ts2-CARs are targeted directly to T cells through in vivo delivery to a patient's body maintained at a permissive temperature (33° C.). While maintained at a permissive temperature, srRNA1ts2-CARs is functional. However, when the temperature of the patient is switched to a normal temperature (37° C.), srRNA1ts2-CARs stop producing CARs. Alternatively, a temperature-sensitive Sendai Viral Vector encoding CARS (SeVts-CARs) could be used. For instance, the SeVts may be an SeV18/TS15ΔF (Ban et al., PNAS 2011).

Example 14: Dominant-Negative Mutants of PD1 and CTLA4

Programmed death-1 (PD1) and cytotoxic T-lymphocyte antigen-4 (CTLA4) are known to function as immune checkpoints. Systemic delivery of antibodies (e.g., nivolumab and pembrolizumab) against PD1 and CTLA4 has been used for cancer therapy. However, up to 20% of patients who receive these therapies experienced adverse events, such as autoimmunity (Roberts et al., 2017). Because the immune checkpoints naturally function to restrict the activation of immune functions to prevent autoimmunity, systemically blocking the function of these molecules by the administration of antibodies is considered to activate immunity against not only cancers, but also patient's own normal cells. To address this issue, dominant negative mutants of PD1 and CTLA1 are expressed specifically in T cells, and thereby block the function of PD1 and CTLA4 only in T cells (Shin et al., 2016). For PD1, it has been shown that a mutant that contains an extracellular domain and transmembrane domain, but lacks cytoplasmic domain, functions as a dominant negative mutant (PD1 decoy or PD1Δ) (Shin et al., 2016). Although a retrovirus vector was used to deliver the PD1 decoy to isolated T cells in a mouse study, the integration of a retrovirus vector into the host genome and the persistent expression of the PD1 decoy is not desirable for humans, considering potential adverse effects of long-term blocking the immune checkpoints. Ideally, the expression of a PD1 decoy in T cells (or other immune cells) should be permanently turned off after exerting its beneficial functions. To this end, ts-agents are used as a delivery vehicle of the dominant-negative mutants of PD1 and CTLA4. Ex Vivo Therapeutic Use of Temperature-Sensitive Agents to Deliver a Dominant-Negative PD1 Mutant Target cells (e.g., T cells) are collected from peripheral blood using an apheresis machine (COBE Spectra) and a magnetic bead-based enrichment method (Miltenyi's CliniMacs Prodigy). Then, the target cells are transfected with srRNA1ts2-PD1Δ and cultured at a permissive temperature (e.g., 33° C.) for a desired amount of time (e.g., 24 hours or 1 week). Subsequently, the treated cells are infused into patients. In the patient's body at non-permissive temperature (37° C.), srRNA1ts2-PD1Δ will eventually stop producing PD1Δ. However, as long as the PD1Δ protein exists in the target cells, PD1 functions are blocked. Alternatively, a temperature-sensitive Sendai Virus Vector encoding PD1Δ could be used in lieu of srRNA1ts2-PD1Δ. For instance, the SeVts may be an SeV18/TS15ΔF (Ban et al., PNAS 2011).

Semi In Vivo Therapeutic Use of Temperature-Sensitive Agents to Deliver a Dominant-Negative PD1 Mutant T cells treated with srRNA1ts2-PD1Δ are immediately infused into a patient who is maintained at a permissive temperature (e.g., 33° C.) by therapeutic hypothermia. While maintained at a permissive temperature, srRNA1ts2-PD1Δ is functional. However, when the temperature of the patient is switched to a normal temperature (37° C.), srRNA1ts2-PD1Δ stop producing PD1Δ. Alternatively, a temperature-sensitive Sendai Virus Vector encoding PD1Δ could be used in lieu of srRNA1ts2-PD1Δ. For instance, the SeVts may be an SeV18/TS15ΔF (Ban et al., PNAS 2011).

In Vivo Therapeutic Use of Temperature-Sensitive Agents to Deliver a Dominant-Negative PD1 Mutant srRNA1ts2-PD1Δ are targeted directly to T cells through in vivo delivery into a patient's body maintained at a permissive temperature (33° C.). While maintaining a permissive temperature, srRNA1ts2-PD1Δ is functional. However, when the temperature of the patient is switched to a normal temperature (37° C.), srRNA1ts2-PD1Δ stop producing PD1Δ. Alternatively, a temperature-sensitive Sendai Virus Vector encoding PD1Δ could be used in lieu of srRNA1ts2-PD1Δ. For instance, the SeVts may be an SeV18/TS15ΔF (Ban et al., PNAS 2011).

Example 15: Combination Therapy of CAR T Cell and Dominant-Negative Mutants of PD1 and CTLA4

Systemic administration of PD1-blocking antibodies enhances the eradication of tumors by CAR T cells (John et al., 2013). Ts-agents, particularly srRNA1ts2, provide a delivery vehicle for both PD1-blocking function and CARs to the same T cells, because srRNA1ts2 has a large cargo capacity and can accommodate multiple genes in the same vector. Ex Vivo Therapeutic Use of Temperature-Sensitive Agents to Deliver CARs and Dominant-Negative PD1 to T Cells The coding regions of PD1Δ and CARs are fused with the insertion of P2A peptide (self-cleaving peptide) between them. This fusion protein-coding sequence is now inserted in srRNA1ts2 vector as GOI. Synthetic RNAs (srRNA1ts2-PD1Δ-CARs) are generated from the srRNA1ts2-PD1Δ-CARs vector. T cells are collected from peripheral blood using an apheresis machine (COBE Spectra) and a magnetic bead-based enrichment method (Miltenyi's CliniMacs Prodigy). Then, T cells are transfected with srRNA1ts2-PD1Δ-CARs and cultured at a permissive temperature (33° C.) for 24 hours (or longer). Subsequently, the treated cells are infused back into the patient. In the patient's body, at a non-permissive temperature (37° C.), srRNA1ts2-PD1Δ-CARs stop producing PD1Δ and CARs. However, a sufficient quantity of PD1Δ and CARs are already present on the surface of the T cells. Alternatively, a temperature-sensitive Sendai Virus Vector encoding PD1Δ-CARs can be used in lieu of srRNA1ts2-PD1Δ-CARs. For instance, the SeVts may be an SeV18/TS15ΔF (Ban et al., PNAS 2011).

Semi In Vivo Therapeutic Use of Temperature-Sensitive Agents to Deliver CARs and Dominant-Negative PD1 to T Cells T cells treated with srRNA1ts2-PD1Δ-CARs are immediately infused into a patient maintained at permissive temperature (e.g., 33° C.) by therapeutic hypothermia. While maintained at a permissive temperature, srRNA1ts2-PD1Δ-CARs is functional. However, when the temperature of the patient is switched to a normal temperature (37° C.), srRNA1ts2-PD1Δ-CARs stop producing CARs and PD1Δ.

Alternatively, a temperature-sensitive Sendai Virus Vector encoding PD1Δ-CARs can be used in lieu of srRNA1ts2-PD1Δ-CARs. For instance, the SeVts may be an SeV18/TS15ΔF (Ban et al., PNAS 2011).

In Vivo Therapeutic Use of Temperature-Sensitive Agents to Deliver CARs and Dominant-Negative PD1 to T Cells srRNA1ts2-PD1Δ-CARs are targeted directly to T cells through in vivo delivery into a patient's body maintained at a permissive temperature (33° C.). While maintained at a permissive temperature, srRNA1ts2-PD1Δ-CARs is functional. However, when the temperature of the patient is switched to a normal temperature (37° C.), srRNA1ts2-PD1Δ-CARs stop producing CARs and PD1Δ. Alternatively, a temperature-sensitive Sendai Virus Vector encoding PD1Δ-CARs can be used in lieu of srRNA1ts2-PD1Δ-CARs. For instance, the SeVts may be an SeV18/TS15ΔF (Ban et al., PNAS 2011).

Example 16: Ribonucleoproteins

Ribonucleoproteins function by forming a complex with RNA. Therapeutic application of ribonucleoproteins is challenging because it is difficult to express both a protein and RNA from the same vector. For example, major components of telomerase are human telomerase reverse transcriptase (TERT) and telomerase RNA (TERC). Abnormal shortening of telomeres causes diseases. Thus, delivery of telomerase (TERT+TERC) to extend telomeres is a desirable therapeutic intervention. However, the persistent presence of telomerase could cause adverse events such as tumor formation. Therefore, it is desirable to have a time-limited delivery of both TERT and TERC. To this end, ts-agents can be used as a delivery vehicle of TERT and TERC.

Ex Vivo Therapeutic Use of Temperature-Sensitive Agents to Deliver TERT and TERC srRNA1ts2 vector is constructed to express a protein TERT in a temperature-sensitive manner. The vector also contains TERC, RNA component sandwiched by self-cleaving ribozymes (e.g., Hammerhead ribozyme). The resulting vector is used to generate synthetic RNA (srRNA1ts2-TERT-TERC). Target cells (e.g., hematopoietic stem cells) are transfected with srRNA1ts2-TERT-TERC. At a permissive temperature (e.g., 33° C.), srRNA1ts2-TERT-TERC replicates and produces TERT (proteins). At the same time, some of the RNA molecules (srRNA1ts2-TERT-TERC) is self-cleaved by ribozymes and becomes TERC (RNAs). Then, the TERT and TERC form a telomerase complex and extend telomeres. The target cells (e.g., hematopoietic stem cells) are then infused into a patient's circulation. At 37° C., a non-permissive temperature, srRNA1ts2-TERT-TERC stops working. Alternatively, a temperature-sensitive Sendai Virus Vector encoding TERT-TERC can be used in lieu of srRNA1ts2-TERT-TERC. For instance, the SeVts may be an SeV18/TS15ΔF (Ban et al., PNAS 2011).

Semi In Vivo Therapeutic Use of Temperature-Sensitive Agents to Deliver TERT and TERC Target cells treated with srRNA1ts2-TERT-TERC are immediately transplanted to a patient maintained at a permissive temperature (e.g., 33° C.) by therapeutic hypothermia. While maintained at a permissive temperature, srRNA1ts2-TERT-TERC is functional. However, when the temperature of the patient is switched to a normal temperature (37° C.), srRNA1ts2-TERT-TERC stops producing TERT and TERC. Alternatively, a temperature-sensitive Sendai Virus Vector encoding TERT-TERC can be used in lieu of srRNA1ts2-TERT-TERC. For instance, the SeVts may be an SeV18/TS15ΔF (Ban et al., PNAS 2011).

In Vivo Therapeutic Use of Temperature-Sensitive Agents to Deliver TERT and TERC srRNA1ts2-TERT-TERC is targeted directly to cells through in vivo delivery into a patient's body maintained at a permissive temperature (33° C.). While maintained at a permissive temperature, srRNA1ts2-TERT-TERC is functional. However, when the temperature of the patient is switched to a normal temperature (37° C.), srRNA1ts2-TERT-TERC stops producing TERT and TERC. Alternatively, a temperature-sensitive Sendai Virus Vector encoding TERT-TERC can be used in lieu of srRNA1ts2-TERT-TERC. For instance, the SeVts may be an SeV18/TS15ΔF (Ban et al., PNAS 2011).

Example 17: Gene Knockdown or Silencing

RNAi, including microRNA, siRNA, and shRNA has become an attractive choice for knocking down the function of specific genes for therapeutic purposes (Kaczmarek et al., 2017). However, a drawback of RNAi technology is its very short-time action, which requires repeated dosing of a large quantity of siRNAs. On the other hand, although plasmids and viruses can provide a strong expression of shRNA from PolIII promoter, it is difficult to stop expression when required. Further, a DNA-based shRNA expression system may be integrated into an organisms' genome and cause mutations. In this sense, a temperature-sensitive srRNA or Sendai virus vector may provide an ideal solution, as they provide footprint-free (no integration into an organism's genome) controllable and prolonged expression of RNAi.

shRNA. An shRNA is incorporated in srRNAts or SeVts as a GOI flanked by a self-cleaving ribozyme, in a manner similar to a guide RNA flanked by a self-cleaving ribozyme shown in Park et al., 2016. An srRNA1ts2-shRNA is delivered to target cells, where a target gene is silenced when the target cells are maintained at a permissive temperature. However, when the temperature is shifted to non-permissive temperature, the production of shRNA stops, and the target gene is unsilenced. Alternatively, a temperature-sensitive Sendai Virus Vector encoding shRNA can be used in lieu of srRNA1ts2-shRNA. For instance, the SeVts may be an SeV18/TS15ΔF (Ban et al., PNAS 2011).

dsRNA. An expression unit of a long double-stranded RNA (dsRNA) is made by connecting a long sense-strand and its antisense-strand of a target RNA (i.e., to be knocked down) by a short linker RNA sequence. This expression unit of dsRNA is inserted in a srRNA1ts2 vector as a GOI flanked by a self-cleaving ribozyme, in a manner similar to a guide RNA flanked by a self-cleaving ribozyme (Park et al., 2016 and Shinagawa T1, Ishii S. 2003). To facilitate the formation of siRNAs from the dsRNA, the srRNA1ts2 vector also expresses human DICER1 (NCBI Reference Sequence: NG_016311.1). An srRNA1ts2-dsRNA or srRNA1ts2-DICER1-dsRNA is delivered to target cells, where a target gene is silenced when the target cells are maintained at a permissive temperature. However, when the temperature is shifted to non-permissive temperature, the production of dsRNA (and DICER1, if present) stops, and the target gene is unsilenced. Alternatively, a temperature-sensitive Sendai Virus Vector encoding dsRNA or dsRNA-DICER1 can be used in lieu of srRNA1ts2-dsRNA or srRNA1ts2-dsRNA-DICER1. For instance, the SeVts may be an SeV18/TS15ΔF (Ban et al., PNAS 2011).

asRNA. An antisense-strand of a target RNA (asRNA) (i.e., to be knocked down) is inserted in a srRNA1ts2 vector as a GOI flanked by a self-cleaving ribozyme, in a manner similar to a guide RNA flanked by a self-cleaving ribozyme shown in Park et al., 2016 and Shinagawa T1, Ishii S. 2003. To facilitate the formation of siRNAs from the dsRNA, srRNA1ts2 vector also expresses human DICER1 (NCBI Reference Sequence: NG_016311.1). An srRNA1ts2-asRNA or srRNA1ts2-DICER1-asRNA is delivered to target cells, where a target gene is silenced when the target cells are maintained at a permissive temperature. However, when the temperature is shifted to non-permissive temperature, the production of a sRNA (and DICER1, if present) stops, and the target gene is unsilenced. Alternatively, a temperature-sensitive Sendai Virus Vector encoding asRNA or asRNA-DICER1 can be used in lieu of srRNA1ts2-asRNA or srRNA1ts2-asRNA-DICER1. For instance, the SeVts may be an SeV18/TS15ΔF (Ban et al., PNAS 2011).

The gene knockdown or gene silencing method detailed above is applied to any of the "ex vivo treatment of cells with ts-agents," "ex vivo therapeutic use of ts-agents", "semi in vivo therapeutic use of ts-agents", or "in vivo therapeutic use of ts-agents."

Example 18: Cell Fusion Therapy

One of the strategies in the field of regenerative medicine is to differentiate human pluripotent stem cells such as embryonic stem (ES) cells and induced pluripotent stem (iPS) cells into desired cell types such as neurons and muscles, and then transplant these differentiated cells into patients. Often, it is desirable to use iPS cells that are made from the patient's own cells such as blood cells or fibroblast cells. For example, to treat a patient with muscular dystrophy, skeletal muscle cells that are differentiated ex vivo from ES cells or iPS cells can be transplanted to patient's skeletal muscles. One of the technical challenges is to ensure the proper engraftment of exogenous muscle cells and the replacement or supplementation of patient's defective muscle functions. To address this issue, RNAs that encode fusogenic proteins can be delivered into the exogenous muscle cells, which facilitates the cell-to-cell fusion among the exogenous muscle cells and a patient's own muscle cells.

Semi In Vivo Therapeutic Use of Temperature-Sensitive Agents to Deliver Fusogenic Proteins srRNA1ts2 vector is constructed to express fusogenic proteins such as Sendai Virus F and HN proteins. F and HN are fused into a single protein via P2A self-cleaving peptide. The srRNA1ts2-F-HN vector is used to generate synthetic RNA (srRNA1ts2-F-HN). It has been well established that the presence of F and HN proteins on the cell surface can induce cell fusion (Rawling et al., 2008). Alternatively, human respiratory syncytial virus F protein, which alone can induce cell-to-cell fusions (Rawling et al., 2008), is cloned into srRNA vectors to generate synthetic RNA (srRNA1ts2-RSVF). Another example of fusogenic proteins are Myomaker (Mymk) and Myomixer (Mymx) (also known as Myomerger) (Bi et al., 2017). Myomaker and myomixer are fused into a single protein via P2A self-cleaving peptide. The srRNA1ts2-Mymk-Mymx vector is used to generate synthetic RNA (srRNA1ts2-Mymk-Mymx). The presence of both Myomaker and Myomixer induces the cell-to-cell fusion, not only muscles, but in fibroblast cells as well (Bi et al., 2017). Human iPS cells are differentiated into skeletal muscles using the method described above. Skeletal muscles are then transfected with srRNA1ts2-HN-F or srRNA1ts2-SRVF or srRNA1ts2-Mymk-Mymx, then immediately injected into the skeletal muscles of a patient, whose body temperature is already lowered to 33° C. by a procedure for therapeutic hypothermia (FIG. 15). While the patient is maintained at the targeted temperature (33° C.) for 24 hours, the fusogenic proteins are expressed in the transplanted skeletal muscle cells, which are then fused to a patient's own defective skeletal muscle cells. Subsequently, the patient's body temperature is returned to normal temperature at 37° C. The ts-agent and fusogenic proteins no longer function in this non-functional condition at 37° C. inside patient's body.

Tissues that can be treated with this semi in vivo use of ts-agents are not limited to skeletal muscles. Cardiomyocytes and hepatocytes are usually polyploidy, and therefore, heart tissues and livers are suitable targets for this therapy. Cardiomyocytes and hepatocytes are tissues that can be easily generated from human ES/iPS cells. Furthermore, semi in vivo use of ts-agents can be used to treat neurological diseases such as spinal cord injury and neurodegenerative diseases such as Parkinson's diseases. Alternatively, a temperature-sensitive Sendai Virus Vector can be used in lieu of srRNA1ts. For instance, the SeVts may be an SeV18/TS15ΔF (Ban et al., PNAS 2011).

The gene knockdown or gene silencing method detailed above may be applied to any of the "ex vivo treatment of cells with ts-agents," "ex vivo therapeutic use of ts-agents", "semi in vivo therapeutic use of ts-agents", or "in vivo therapeutic use of ts-agents."

Example 19: Vaccines

Temperature-sensitive agents (ts-agents) such as srRNAs or Sendai virus vectors, are functional at a permissive temperature (e.g., about 31-34° C.), but non-functional at a non-permissive temperature (e.g., ≥37° C.). While the core body temperature of a human subject is about 37° C., the surface body temperature of a human subject is about 31-34° C. Thus, ts-agents administered to cells at or near the surface of a body of a human patient (e.g., intradermally, subcutaneously, or intramuscularly) are functional without lowering the core body temperature of the human patient (FIG. 20). No further action is required.

Similarly, the temperature of the nasal cavity and upper trachea of a human subject is about 32° C., and the temperature of the subsegmental bronchi of a human subject is about 35° C. (McFadden et al., 1985). As such, ts-agents administered intranasally to cells of the upper respiratory tract (nasal cavity, pharnyx, and/or larnyx) and/or upper trachea of a human patient are functional without lowering the core body temperature of the human patient (FIG. 22). Intranasal administration may be done by insufflation, inhalation or instillation. No further action is required.

Alternatively, the ts-agent administered to cells at or near the surface of a body of a human patient (e.g., intradermally, subcutaneously, or intramuscularly) can subsequently be rendered non-functional by raising the surface body temperature of the human patient, for instance by application of a heat patch or heating pad to the treated area of the patient's skin, soaking in a warm bath, or sitting in a hot sauna. This therapeutic procedure is very safe in that the ts-agent is only functional in the intended area and is non-functional in other areas of a patient's body. Similarly, the ts-agent administered intranasally to cells of the upper respiratory tract (nasal cavity, pharnyx, and/or larnyx) and/or upper trachea of a human patient can be rendered non-functional by placing the human patient in an environment with a non-permissive temperature (e.g., ≥37° C.).

Immunogenic compositions and vaccines employing srRNA1ts2 as a vector are suitable for inducing an immune response against all types of pathogens. For instance, recombinant srRNA1ts2 vectors can be constructed relatively quickly once a coding region of an antigen of a pathogen is known. Additionally, RNA of a srRNA1ts2 vector can be transcribed in vitro without the use of materials of animal or human origin. In this way, vaccines employing srRNA1ts2 vectors are easily adapted to production using current good manufacturing practice. Alternatively, a temperature-sensitive Sendai virus vector encoding an antigen of a pathogen can be employed (e.g., SeV18/TS15ΔF).

The construction of srRNA1ts2 is described above in Example 3. In brief, srRNA1ts2 comprises a Venezuelan equine encephalitis virus (VEEV) replicon lacking a VEEV structural protein coding region. The VEEV replicon comprises a VEEV nonstructural protein coding region with an insertion of 15-18 nucleotides resulting in expression of a nonstructural Protein 2 (nsP2=helicase proteinase) comprising 5 or 6 additional amino acids (SEQ ID NO:39=TGAAA) between beta sheet 5 and beta sheet 6 of the nsP2. The additional amino acids result in temperature-sensitivity of the self-replicating RNA.

The genomes of exemplary srRNA1ts2 vectors encoding the spike protein (or a portion thereof) of severe acute respiratory syndrome coronavirus-2 (SARS-CoV-2, also known as 2019-nCoV) are shown in FIG. 21. The spike protein and the receptor-binding domain (RBD) of the spike protein of a related coronavirus were previously identified as targets for vaccine and drug development (Du et al., Nat Rev Microbiol, 7:226-236, 2009). The sequence of the RNA genome of 2019-nCoV is set forth in NCBI Accession No.: NC_045512. Three distinct temperature-sensitive srRNA1ts2 vectors were constructed. srRNA1ts2-2019-nCoV-Spike encodes the full length spike protein. srRNA1ts2-2019-nCoV-RBD1 encodes a CD5 signal peptide fused to the RBD of the spike protein. srRNA1ts2-2019-nCoV-RBD2 encodes a signal peptide of the spike protein fused to the RBD, transmembrane domain, and cytoplasmic tail of the spike protein. Expression of the spike protein or fragment thereof is driven by the 26S promoter of the VEEV replicon.

The entire RNAs are transcribed in vitro using T7 RNA polymerase. Then, the RNAs are transfected into cells of a subject's dermal tissue. A suitable method for transfection is by patch electroporation of naked RNAs. Alternatively, a microneedle is used to transfect RNAs intradermally. For instance, a dissolvable microneedle made with hyaluronic acid or a chitosan-hyaluronic acid complex is used to transfect RNAs intradermally In some embodiments, a regular Mantoux procedure can be used. Alternatively, a special injection device designed to facilitate the intradermal injection can be used.

The amino acid sequence of the spike protein of srRNA1ts2-2019-nCoV-Spike is set forth as SEQ ID NO:41: MFVFLVLLPLVSSQCVNLTTRTQLPPAYTNSFTRGV YY PDKVFRSSVLHSTQDLFLPFFS NVTWFHAIHV SGTNGTKRFDNPVLPFNDGVYFASTEKSNIIRG-WIFGTTLDSKTQSLLIV NNATNVVIKVCEFQFCNDP-FLGVYYHKNNKSWMESEFRVYSSANNCTFEYVSQP-FLMDLE GKQGNFKNLREFVFKNIDGYFKI YSKHTPI NLVRDLPQGFSALEPLVDLPIGINITRFQT LLALHRSY LTPGDSSSGWTAGAAAYYVGYLQPRTFLLKYNENG TITDAVDCALDPLSETK CTLKSFTVEKGIYQTSNFR VQPTESIVRFPNITNLCPFGEVFNATRFASVYAWNRK RISN CVADYSVLYNSASFSTFKCYGVSPTKLNDL CF TN VYADSFVIRGDEVRQIAPGQTGKIAD YNYKLPDD FTGCVIAWNSNNLDSKVGGNYNYLRLFRKSNLK-PFERDISTEIYQAGSTPC NGVEGFNCYFPLQSYGF-QPTNGVGYQPYRVVVLSFELLHAPATVCGPKKST-NLVKNKCVN FNFNGLTGTGVLTESNKKFLPFQQFG-RDIADTTDAVRDPQTLEILDITPCSFGGVSVITP GTNTSNQVAVLYQDVNCTEVPVAIHADQLTPTWRV-YSTGSNVFQTRAGCLIGAEHVNNSY ECDIPIGAG-ICASYQTQTNSPRRARSVASQSIIAYTMSLGAENS-VAYSNNSIAIPTNFTI SVTTEILPVSMTKTSVDCTMY-ICGDSTECSNLLLQYGSFCTQLNRALTGIAVEQ-DKNTQE VFAQVKQIYKTPPIKDFGGFNFSQILPDPSK-PSKRSFIEDLLFNKVTLADAGFIKQYGDC LGDIAA-RDLICAQKFNGLTVLPPLLTDEMIAQYTSALLAGT-ITSGWTFGAGAALQIPFAM QMAYRFNGIGVTQN-VLYENQKLIANQFNSAIGKIQDSLSSTASALGKLQD-VVNQNAQALN TLVKQLSSNFGAISSVLNDILSRL-DKVEAEVQIDRLITGRLQSLQTYVTQQLIRAAEIRA SANLAATKMSECVLGQSKRVDFCGKGYHLMSFPQ-SAPHGVVFLHVTYVPAQEKNFTTAPA ICHDGKAHF-PREGVFVSNGTHWFVTQRNFYEPQIITTDNTFVSG-NCDVVIGIVNNTVYDP LQPELDSFKEELDKYFKNHT-SPDVDLGDISGINASVVNIQKEIDRLNEVAKNLNESL-IDL QELGKYEQYIKWPWYIWLGFIAGLIAIVMVTIM-LCCMTSCCSCLKGCCSCGSCCKFDEDD SEPVLK-GVKLHYT. The signal peptide extends from residues 1-15, the extracellular region extends from residues 16-1213, the transmembrane domain extends from residues 1214-1236, and the cytoplasmic domain extends from residues 1237-1273.

The amino acid sequence of the spike protein fragment of srRNA1ts2-2019-nCoV-RBD1 is set forth as SEQ ID NO:42: MPMGSLQPLATLYLLGMLVASCLGPNITN-LCPFGEVFNATRFASVYAWNRKRISNCVADY SVLYN-SASFSTFKCYGVSPTKLNDLCFTNVYADSFVIRGDE-VRQIAPGQTGKIADYNYKLPDDFTGCVIAWNSN-NLDSKVGGNYNYLYRLFRKSNLKPFERDISTEIYQA-GSTPCNGVEGFNCYFPLQSYGFQPTNGVGYQPYR-VVVLSFELLHAP. The CD5 signal peptide extends from residues 1-24 and the RBD extends from residues 25-192.

The amino acid sequence of the spike protein fragment of srRNA1ts2-2019-nCoV-RBD2 is set forth as SEQ ID NO:43: MFVFLVLLPLVSSQCPNITNLCPFGEVFNATR-FASVYAWNRKRISNCVADYSVLYNSASF STFKCY-GVSPTKLNDLCFTNVYADSFVIRGDEVRQIAPGQTG-KIADYNYKLPDDFTGCVI AWNSNNLDSKVGGNYNY-LYRLFRKSNLKPFERDISTEIYQAGSTPCNGVEGFN-CYFPLQS YGFQPTNGVGYQPYRVVVLSFELLHA-PWYIWLGFIAGLIAIVMVTIMLCCMTSCCSCLKG CCSCGSCCKFDEDDSEPVLKGVKLHYT. The signal peptide extends from residues 1-15, the RBD extends from residues 16-207, the transmembrane domain extends from residues 208-230, and the cytoplasmic domain extends from residues 231-267.

The amino acid sequence of the RBD is set forth as SEQ ID NO:44:

PNITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFTG

CVIAWNSNNLDSKVGGNYNYLYRLFRKSNLKPFERDISTEIYQAGSTPCNG

VEGFNCYFPLQSYGFQPTNGVGYQPYRVVVLSFELLHAP.

Example 20: In Vivo Expression of GOI after Injection of Temperature Sensitive-srRNA As described in Example 19 and shown in FIG. 20, temperature-sensitive agents (ts-agents), such as srRNAs or Sendai virus vectors, which are functional at a permissive temperature (e.g., about 31-34° C.), but non-functional at a non-permissive temperature (e.g., 37° C.), can be delivered to the surface of a human body (e.g., skin) for controlled expression of a gene of interest (GOI). Thus, ts-agents encoding a GOI have an inherent safety feature in that expression of the GOI is limited to the local area (permissive temperature) to which the ts-agent is delivered. That is, unintended expression of a GOI by a ts-agent does not occur in areas of a subject's body that naturally have a temperature above or below the permissive temperature. This example demonstrates that this safety feature works in vivo in a model mammalian subject, namely mice. The skin temperature of mice is similar to that of humans (Mortola 2013) and thus intradermal delivery of ts-agents to mice is expected to mimic intradermal delivery of ts-agents to humans.

RNAs were formulated as naked RNAs, without lipid nanoparticles or any other transfection reagents, in lactated Ringer's solution. RNA (5 μg) encoding luciferase (LUC) was injected intradermally into a single site on the right hind limb of CD-1 outbred mice. Luciferase activity was visualized and quantitated by using a bioluminescent Imaging system, AMI HTX (Spectral Instruments Imaging, Tucson, Ariz.).

FIG. 23 shows the time-course of in vivo luciferase activity from Day 0 (injection day) through Day 26 in recipients of: a control synRNA-LUC from TriLink (San Diego, Calif.); or a temperature-sensitive srRNA (srRNA1ts2-LUC). Luciferase imagining showed that intradermal injection of naked RNA encoding luciferase resulted in expression of luciferase in vivo. Strikingly, the in vivo expression of luciferase driven by srRNA1ts2-LUC, due to its self-replicating feature, continued for nearly a month. In contrast, the in vivo expression of luciferase driven by synRNA-LUC continued for only a little over a week. Furthermore, the expression level of luciferase in recipients of srRNA1ts2-LUC, due to its self-replicating feature, was 10- to 100-fold higher than the expression level of luciferase in recipients of synRNA-LUC. Importantly, luciferase expression was not observed in uninjected areas of the recipients' skin, or within internal organs of the recipients. This observation indicates that the temperature-sensitive srRNA1ts2-LUC did not replicate and express luciferase under non-permissive conditions.

Example 21: Cellular Immunity Elicited by Temperature-Sensitive srRNA Vaccine

In this example, cytokine-secreting splenocytes elicited by intradermal administration of temperature-sensitive srRNA expressing the receptor binding domain (RBD) of the spike protein of SARS CoV-2 were measured. RNAs were formulated as naked RNAs, without any lipid nanoparticles or any other transfection reagents, in lactated Ringer's solution. To assess cellular immunity, the enzyme-linked immunospot (ELISpot) assay, which quantitates the number of cytokine secreting cells, was performed on splenocytes obtained from CD-1 outbred mice that received a single dose of a placebo (buffer only) or 5 μg, 25 μg, or 100 μg of srRNA1ts2-2019-CoV-RBD1 RNA (described in Example 19). Splenocytes isolated 12 days post injection were stimulated for 24 hours with a pool of 53 peptides (15mers with 11 amino acid overlaps) that cover SARS-CoV-2 RBD (PepMix SARS-CoV-2 [S-RBD], JPT Peptide Technologies GmbH, Berlin, Germany).

As shown in FIG. 24A, srRNA1ts2-2019-nCoV-RBD1 administered by intradermal injection induced cellular immunity against SARS-CoV-2 RBD in a dose-dependent manner. IFN-γ-secreting cells (FIG. 24A), which are characteristic of type 1 CD4+T helper cells (Th1 cells) and CD8+ cytotoxic T cells, were preferentially expanded by the temperature-sensitive SARS-CoV-2 RBD srRNA vaccine. In contrast, IL4-secreting cells (FIG. 24B), which are characteristic of type 2 CD4+T helper cells (Th2 cells), were not expanded by the temperature-sensitive SARS-CoV-2 RBD srRNA vaccine. In conclusion, the results showed that intradermal administration of srRNA1ts2-2019-nCoV-RBD1 elicited a Th1 dominant (Th1>Th2) cellular immune response against SARS-CoV-2 RBD, which is a desirable feature of a vaccine directed against a viral pathogen.

Example 22: Humoral Immunity Elicited by Temperature-Sensitive srRNA Vaccine

In this example, antibodies elicited by intradermal administration of temperature-sensitive srRNA expressing the receptor binding domain (RBD) of the spike protein of SARS CoV-2 were measured. RNAs were formulated as naked RNAs, without any lipid nanoparticles or any other transfection reagents, in lactated Ringer's solution. Groups of CD-1 outbred mice (N=10) received one of three formulations by intradermal injection on Day 0 and Day 14 (black triangles): a placebo (buffer only) (FIG. 25A), 5 μg of temperature-sensitive srRNA1ts2-2019-CoV-RBD1 RNA (FIG. 25B), or 5 μg of temperature-sensitive srRNA1ts2-2019-CoV-RBD1 RNA in combination with a RNase inhibitor (3 units of RNasin Plus) (Promega, Madison, Wis.) (FIG. 25C). All mice received a recombinant RBD protein (Ala319-Phe541, with a C-terminal 6-His tag, Accession #YP_009724390.1: R&D Systems, Minneapolis, Minn.) by intradermal injection on Day 49 (open triangles). To assess humoral immunity, an enzyme-linked immunosorbent assay (ELISA), which quantitates the amount of immunoglobulin G (IgG) specific to a recombinant RBD protein (represented by the measurement at OD450), was performed on serum obtained from injected mice on Day −3, Day 14, Day 28, Day 46, Day 56, and Day 63. Amount of IgG in serum is shown as OD450.

As shown in FIGS. 25A-25C, an increase in RBD-specific IgG was not observed in any group after only the prime and first booster. However, when mice received a second booster comprising a recombinant RBD protein, the groups that received a prime and first booster comprising srRNA1ts2-2019-CoV-RBD1 quickly responded with an increase in RBD-specific IgG (FIGS. 25B-C), whereas the placebo group did not show an appreciably increase in RBD-specific IgG (FIG. 25A). The rapid increase in RBD-specific IgG upon the injection of a recombinant RBD protein indicates that the mice that received a prime and first booster comprising srRNA1ts2-2019-CoV-RBD1, maintained immune memory, and exhibited a secondary humoral response to a recombinant RBD.

What is claimed:

1. A composition for stimulating an immune response against an antigen in a mammalian subject, comprising an excipient and a temperature-sensitive agent (ts-agent) encoding the antigen, wherein the ts-agent is
 a temperature-sensitive Sendai viral vector,
 and
 wherein the ts-agent is capable of expressing the antigen at a permissive temperature but not at a non-permissive temperature, and the antigen is a spike protein or fragment thereof of a coronavirus.

2. The composition of claim 1, wherein the coronavirus is 2019-nCoV and the antigen comprises a receptor-binding domain (RBD) of the 2019-nCoV.

3. The composition of claim 1, wherein the permissive temperature is from 31° C. to 35° C., and the non-permissive temperature is 37° C.±0.5° C.

4. A composition for stimulating an immune response against an antigen in a mammalian subject, comprising an excipient and a temperature-sensitive agent (ts-agent) encoding the antigen, wherein the ts-agent is a temperature-sensitive self-replicating RNA comprising an Alphavirus replicon lacking a viral structural protein coding region, and wherein the ts-agent is capable of expressing the antigen at a permissive temperature but not at a non-permissive temperature, and the antigen is a spike protein or fragment thereof of a coronavirus.

5. The composition of claim 4, wherein the Alphavirus is selected from the group consisting of a Venezuelan equine encephalitis virus, a Sindbis virus, and a Semliki Forrest virus.

6. The composition of claim 4, wherein the Alphavirus is a Venezuelan equine encephalitis virus.

7. The composition of claim 4, wherein the coronavirus is 2019-nCoV and the antigen comprises a receptor-binding domain (RBD) of the 2019-nCoV.

8. The composition of claim 4, wherein the permissive temperature is from 31° C. to 35° C., and the non-permissive temperature is 37° C.±0.5° C.

9. A temperature-sensitive agent (ts-agent), wherein the is-agent is
 a temperature-sensitive self-replicating RNA comprising an Alphavirus replicon lacking a viral structural protein coding region, and
 wherein the ts-agent comprises a nonstructural protein coding region with an insertion of 12-18 nucleotides resulting in expression of a nonstructural Protein 2 (nsP2) comprising from 4 to 6 additional amino acids between beta sheet 5 and beta sheet 6 of the nsP2.

10. The temperature-sensitive agent of claim 9, wherein the additional amino acids comprise one sequence selected from the group consisting of SEQ ID NO:38 (GCGRT), SEQ ID NO:39 (TGAAA), and SEQ ID NO:40 (LRPHP).

11. The temperature-sensitive agent of claim 9, wherein the additional amino acids comprise the sequence of SEQ ID NO:39 (TGAAA).

12. The temperature-sensitive agent of claim 9, wherein the amino acid sequence of the nsP2 comprises one sequence selected from the group consisting of SEQ ID NOs:29-36.

13. The temperature-sensitive agent of claim 9, wherein the ts-agent encodes an antigen of a pathogen, and the ts-agent is capable of expressing the antigen at a permissive temperature but not at a non-permissive temperature.

14. The temperature-sensitive agent of claim 13, wherein the antigen is a viral antigen and the viral antigen is not an Alphavirus antigen.

15. The temperature-sensitive agent of claim 9, wherein the Alphavirus is selected from the group consisting of a Venezuelan equine encephalitis virus, a Sindbis virus, and a Semliki Forrest virus.

16. The temperature-sensitive agent of claim 9, wherein the Alphavirus is a Venezuelan equine encephalitis virus.

17. The temperature-sensitive agent of claim 9, wherein the ts-agent encodes a pharmaceutical agent, and wherein the ts-agent is capable of expressing the pharmaceutical agent at a permissive temperature but not at a non-permissive temperature.

18. The temperature-sensitive agent of claim 17, wherein the permissive temperature is from 31° C. to 35° C., and the non-permissive temperature is 37° C.±0.5° C.

19. The temperature-sensitive agent of claim 18, wherein the pharmaceutical agent comprises a protein.

20. The temperature-sensitive agent of claim 18, wherein the pharmaceutical agent is selected from the group consisting of a non-coding RNA, a siRNA, a shRNA, and an endonuclease editing system.

* * * * *

UNITED STATES PATENT AND TRADEMARK OFFICE
CERTIFICATE OF CORRECTION

PATENT NO. : 11,421,248 B2
APPLICATION NO. : 17/404901
DATED : August 23, 2022
INVENTOR(S) : Minoru S. H. Ko It is certified that error appears in the above-identified patent and that said Letters Patent is hereby corrected as shown below:

In the Claims

In Column 84, Claim 9, Line 55, delete "is-agent" and insert --ts-agent--.

Signed and Sealed this
Seventeenth Day of January, 2023

Katherine Kelly Vidal
*Director of the United States Patent and Trademark Office*